United States Patent
Mascitti et al.

(10) Patent No.: US 8,080,580 B2
(45) Date of Patent: Dec. 20, 2011

(54) DIOXA-BICYCLO[3.2.1]OCTANE-2,3,4-TRIOL DERIVATIVES

(75) Inventors: Vincent Mascitti, Groton, CT (US); Benjamin M. Collman, Ledyard, CT (US)

(73) Assignee: Pfizer Inc., New York, NY (US)

( * ) Notice: Subject to any disclaimer, the term of this patent is extended or adjusted under 35 U.S.C. 154(b) by 323 days.

(21) Appl. No.: 12/546,306

(22) Filed: Aug. 24, 2009

(65) Prior Publication Data

US 2010/0056618 A1 Mar. 4, 2010

Related U.S. Application Data

(60) Provisional application No. 61/092,470, filed on Aug. 28, 2008, provisional application No. 61/227,212, filed on Jul. 21, 2009.

(51) Int. Cl.
*A61K 31/352* (2006.01)
*C07D 493/08* (2006.01)
(52) U.S. Cl. ........................ 514/456; 549/397
(58) Field of Classification Search .................. 514/456; 549/397
See application file for complete search history.

(56) References Cited

U.S. PATENT DOCUMENTS

| | | | | |
|---|---|---|---|---|
| 5,047,518 A | 9/1991 | Furneaux et al. | ............... | 536/4.1 |
| 5,591,836 A | 1/1997 | Mazur et al. | ............... | 536/6.1 |
| 6,069,238 A | 5/2000 | Hitchcock et al. | ............... | 536/17.5 |
| 6,414,126 B1 | 7/2002 | Ellsworth et al. | ............... | 536/17.2 |
| 6,486,299 B1 | 11/2002 | Shimkets | ............... | 530/350 |
| 6,515,117 B2 | 2/2003 | Ellsworth et al. | ............... | 536/17.2 |
| 6,555,519 B2 | 4/2003 | Washburn | ............... | 514/3 |
| 6,627,611 B2 | 9/2003 | Tomiyama et al. | ............... | 514/23 |
| 6,683,056 B2 | 1/2004 | Washburn et al. | ............... | 514/25 |
| 6,774,112 B2 | 8/2004 | Gougoutas | ............... | 514/23 |
| 6,815,428 B2 | 11/2004 | Ohsumi et al. | ............... | 514/25 |
| 6,838,442 B2 | 1/2005 | Bussolari et al. | ............... | 514/25 |
| 6,872,706 B2 | 3/2005 | Fujikura et al. | ............... | 514/25 |
| 6,908,905 B2 | 6/2005 | Ohsumi et al. | ............... | 514/25 |
| 6,936,590 B2 | 8/2005 | Washburn et al. | ............... | 514/25 |
| 6,972,283 B2 | 12/2005 | Fujikura et al. | ............... | 514/27 |
| 7,045,665 B2 | 5/2006 | Fujikura et al. | ............... | 568/744 |
| 7,053,060 B2 | 5/2006 | Fujikura et al. | ............... | 514/25 |
| 7,056,892 B2 | 6/2006 | Fujikura et al. | ............... | 514/27 |
| 7,084,123 B2 | 8/2006 | Fujikura et al. | ............... | 514/27 |
| 7,087,579 B2 | 8/2006 | Nishimura et al. | ............... | 514/27 |
| 7,101,856 B2 | 9/2006 | Glombik et al. | ............... | 514/25 |
| 7,169,761 B2 | 1/2007 | Tomiyama et al. | ............... | 514/23 |
| 7,202,350 B2 | 4/2007 | Imamura et al. | ............... | 536/1.11 |
| 7,217,697 B2 | 5/2007 | Shiohara et al. | ............... | 514/25 |
| 7,247,705 B2 | 7/2007 | Iwamoto et al. | ............... | 530/350 |
| 7,250,522 B2 | 7/2007 | Sato et al. | ............... | 549/28 |
| 7,271,153 B2 | 9/2007 | Nishimura et al. | ............... | 514/27 |
| 7,288,528 B2 | 10/2007 | Frick et al. | ............... | 514/25 |
| 7,294,618 B2 | 11/2007 | Fushimi et al. | ............... | 514/25 |
| 7,371,730 B2 | 5/2008 | Iyobe et al. | ............... | 514/25 |
| 7,371,732 B2 | 5/2008 | Eickelmann et al. | ............... | 514/25 |
| 7,375,087 B2 | 5/2008 | Teranishi et al. | ............... | 514/25 |
| 7,375,090 B2 | 5/2008 | Himmelsbach et al. | ............... | 514/27 |
| 7,375,113 B2 | 5/2008 | Fushimi et al. | ............... | 514/303 |
| 7,375,213 B2 | 5/2008 | Deshpande et al. | ............... | 536/124 |
| 7,393,836 B2 | 7/2008 | Eckhardt et al. | ............... | 514/23 |
| 7,414,072 B2 | 8/2008 | Sato et al. | ............... | 514/432 |
| 7,417,032 B2 | 8/2008 | Eckhardt et al. | ............... | 514/23 |
| 7,419,959 B2 | 9/2008 | Eckhardt et al. | ............... | 514/23 |
| 7,439,232 B2 | 10/2008 | Kakinuma et al. | ............... | 514/24 |
| 7,541,341 B2 | 6/2009 | Fushimi et al. | ............... | 514/25 |
| 7,560,230 B2 | 7/2009 | Tidmarsh | ............... | 435/6 |
| 7,566,699 B2 | 7/2009 | Fushimi et al. | ............... | 514/27 |
| 7,576,064 B2 | 8/2009 | Kikuchi et al. | ............... | 514/27 |
| 7,579,449 B2 | 8/2009 | Eckhardt et al. | ............... | 536/1.11 |
| 7,589,193 B2 | 9/2009 | Washburn et al. | ............... | 536/122 |
| 7,635,684 B2 | 12/2009 | Fushimi et al. | ............... | 514/27 |
| 7,655,633 B2 | 2/2010 | Fujikura et al. | ............... | 514/35 |
| 7,687,469 B2 | 3/2010 | Eckhardt et al. | ............... | 514/23 |
| 2002/0034799 A1 | 3/2002 | Donoho et al. | ............... | 435/183 |
| 2002/0081678 A1 | 6/2002 | Merkulov et al. | ............... | 435/183 |
| 2002/0111315 A1 | 8/2002 | Washburn et al. | ............... | 514/25 |
| 2003/0022309 A1 | 1/2003 | Merkulov et al. | ............... | 435/69.1 |
| 2003/0045553 A1 | 3/2003 | Bussolari et al. | ............... | 514/340 |
| 2003/0054453 A1 | 3/2003 | Curtis et al. | ............... | 435/69.1 |
| 2003/0195235 A1 | 10/2003 | Bussolari et al. | ............... | 514/340 |
| 2003/0199557 A1 | 10/2003 | Bussolari et al. | ............... | 514/342 |

(Continued)

FOREIGN PATENT DOCUMENTS

CA 2572149 1/2006

(Continued)

OTHER PUBLICATIONS

Ehrenkranz, et al, *Diabetes Metab. Res. Rev.*, vol. 21(1), pp. 31-38 (2005).
Mancuso, et al., *Synthesis*, vol. 1981(3). pp. 165-185 (1981).
Meng, et al., *J. Med. Chem.*, vol. 51(6). pp. 1145-1149 (2006).
Fujimori, et al., *J. Pharmacol. Exp. Ther.*, vol. 327(1), pp. 268-278 (2008).
Lee, et al., *J. Biol. Chem.*, vol. 269(16), pp. 12032-12039 (1994).
Chasis, et al., *J. Clin. Invest.*, vol. 12(6), pp. 1063-1090 (1933).
Idris, et al., *Diabetes, Obesity and Metabolism*, vol. 11(2), pp. 79-88 (2009).

(Continued)

*Primary Examiner* — Bernard Dentz
(74) *Attorney, Agent, or Firm* — Lisa A. Samuels

(57) ABSTRACT

Compounds of Formula (I) are described herein and the uses thereof for the treatment of diseases, conditions and/or disorders mediated by sodium-glucose transporter inhibitors (in particular, SGLT2 inhibitors).

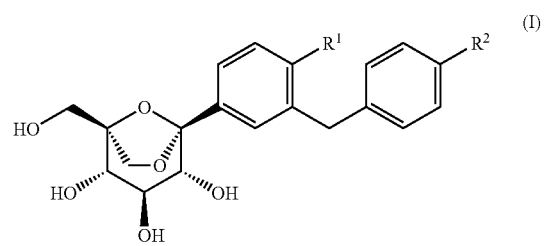

20 Claims, 9 Drawing Sheets

U.S. PATENT DOCUMENTS

| | | | |
|---|---|---|---|
| 2004/0063170 A1 | 4/2004 | Fujikura et al. | 435/41 |
| 2004/0259819 A1 | 12/2004 | Frick et al. | 514/43 |
| 2005/0089955 A1 | 4/2005 | Gong et al. | 435/69.1 |
| 2005/0186613 A1 | 8/2005 | Merkulov et al. | 435/6 |
| 2005/0233988 A1 | 10/2005 | Nomura et al. | 514/43 |
| 2006/0019948 A1 | 1/2006 | Eckhardt et al. | 514/231.5 |
| 2006/0035841 A1 | 2/2006 | Eckhardt et al. | 514/23 |
| 2006/0035844 A1 | 2/2006 | Ito et al. | 514/25 |
| 2006/0063711 A1 | 3/2006 | Iwamoto et al. | 514/12 |
| 2006/0121465 A1 | 6/2006 | Lang et al. | 435/6 |
| 2006/0122126 A1 | 6/2006 | Imamura et al. | 514/23 |
| 2006/0189548 A1 | 8/2006 | Himmelsbach et al. | 514/23 |
| 2007/0004648 A1 | 1/2007 | Himmelsbach et al. | 514/25 |
| 2007/0009615 A1 | 1/2007 | Zhong | 424/729 |
| 2007/0027092 A1 | 2/2007 | Himmelsbach et al. | 514/23 |
| 2007/0036874 A1 | 2/2007 | Zhong | 424/729 |
| 2007/0049537 A1 | 3/2007 | Eckhardt et al. | 514/23 |
| 2007/0054867 A1 | 3/2007 | Eckhardt et al. | 514/25 |
| 2007/0059356 A1 | 3/2007 | Almarsson et al. | 424/464 |
| 2007/0099237 A1 | 5/2007 | Rodriguez-Hornedo | 435/7.1 |
| 2007/0185197 A1 | 8/2007 | Fujikura et al. | 514/502 |
| 2007/0197449 A1 | 8/2007 | Fushimi et al. | 514/23 |
| 2007/0197450 A1 | 8/2007 | Fushimi et al. | 514/23 |
| 2007/0197623 A1 | 8/2007 | Brummerhop et al. | 514/403 |
| 2007/0259821 A1 | 11/2007 | Eckhardt et al. | 514/23 |
| 2007/0275907 A1 | 11/2007 | Chen et al. | 514/23 |
| 2007/0293690 A1 | 12/2007 | Tomiyama et al. | 549/417 |
| 2008/0045466 A1 | 2/2008 | Katsuno et al. | 514/25 |
| 2008/0096802 A1 | 4/2008 | Bussolari et al. | 514/4 |
| 2008/0132563 A1 | 6/2008 | Kakinuma et al. | 514/432 |
| 2008/0139484 A1 | 6/2008 | Teranishi et al. | 514/25 |
| 2008/0234367 A1 | 9/2008 | Washburn et al. | 514/460 |
| 2008/0318874 A1 | 12/2008 | Matsuoka et al. | 514/25 |
| 2008/0319047 A1 | 12/2008 | Matsuoka et al. | 514/443 |
| 2009/0030006 A1 | 1/2009 | Kobayashi et al. | 514/520 |
| 2009/0054356 A1 | 2/2009 | Fushimi et al. | 514/27 |
| 2009/0074738 A1 | 3/2009 | Yonekubo et al. | 424/94.1 |
| 2009/0075864 A1 | 3/2009 | Bussolari et al. | 514/4 |
| 2009/0137499 A1 | 5/2009 | Honda et al. | 514/27 |
| 2009/0143316 A1 | 6/2009 | Imamura et al. | 514/25 |
| 2009/0182039 A1 | 7/2009 | Imamura et al. | 514/460 |
| 2009/0214477 A1 | 8/2009 | Betz et al. | 424/93.2 |
| 2010/0004465 A1 | 1/2010 | Kakinuma et al. | 549/28 |
| 2010/0093744 A1 | 4/2010 | Sato | 514/250 |

FOREIGN PATENT DOCUMENTS

| | | |
|---|---|---|
| CA | 2655780 | 12/2007 |
| CA | 2666375 | 4/2008 |
| DE | 10006887 | 9/2001 |
| EP | 0341062 | 11/1989 |
| EP | 0850948 | 4/2002 |
| EP | 1609798 | 12/2005 |
| EP | 1609799 | 12/2005 |
| EP | 1852439 | 11/2007 |
| EP | 2048152 | 4/2009 |
| EP | 2048153 | 4/2009 |
| JP | 2003012686 | 1/2003 |
| JP | 2004196788 | 7/2004 |
| JP | 2004359630 | 12/2004 |
| JP | 2005247834 | 9/2005 |
| JP | 2006117651 | 5/2006 |
| JP | 2008050353 | 3/2008 |
| WO | WO9109537 | 7/1991 |
| WO | WO9307167 | 4/1993 |
| WO | WO98 41648 | 9/1998 |
| WO | WO01 57214 | 8/2001 |
| WO | WO03011880 | 2/2003 |
| WO | WO03020737 | 3/2003 |
| WO | WO 03055914 | 7/2003 |
| WO | WO03056005 | 7/2003 |
| WO | WO03056329 | 7/2003 |
| WO | WO2004019956 | 3/2004 |
| WO | WO2004099230 | 11/2004 |
| WO | WO2004106352 | 12/2004 |
| WO | WO2005011592 | 2/2005 |
| WO | WO2005012242 | 2/2005 |
| WO | WO2005012243 | 2/2005 |
| WO | WO2005012318 | 2/2005 |
| WO | WO2005012321 | 2/2005 |
| WO | WO2005012326 | 2/2005 |
| WO | WO2005095372 | 10/2005 |
| WO | WO2005095373 | 10/2005 |
| WO | WO2005100998 | 10/2005 |
| WO | WO2006062224 | 6/2006 |
| WO | WO2006080577 | 8/2006 |
| WO | WO2006108842 | 10/2006 |
| WO | WO2006115137 | 11/2006 |
| WO | WO2006117359 | 11/2006 |
| WO | WO2006117360 | 11/2006 |
| WO | WO2006120208 | 11/2006 |
| WO | WO2007014895 | 2/2007 |
| WO | WO2007031548 | 3/2007 |
| WO | WO2007126117 | 11/2007 |
| WO | WO2007128480 | 11/2007 |
| WO | WO2007129668 | 11/2007 |
| WO | WO2007136116 | 11/2007 |
| WO | WO2007140191 | 12/2007 |
| WO | WO2008002824 | 1/2008 |
| WO | WO2008013321 | 1/2008 |
| WO | WO2008013322 | 1/2008 |
| WO | WO2008020011 | 1/2008 |
| WO | WO2008034859 | 3/2008 |
| WO | WO2008042688 | 4/2008 |
| WO | WO2008049923 | 5/2008 |
| WO | WO2008055870 | 5/2008 |
| WO | WO2008055940 | 5/2008 |
| WO | WO2008019591 | 9/2008 |
| WO | WO2008115574 | 9/2008 |
| WO | WO2009014970 | 1/2009 |
| WO | WO2009022010 | 2/2009 |
| WO | WO2009026537 | 2/2009 |
| WO | WO2009091082 | 7/2009 |

OTHER PUBLICATIONS

Kanai, et al., *J. Cum Invest.*, vol. 93(1), pp. 397-404 (1994).
Takagaki, et al., *Chemistry Letters*, vol. 38(7), pp. 650-651 (2009).
Goodwin, et al., *J. Med. Chem.*, vol. 52(20), pp. 6201-6204 (2009).
Capon, *Chem. Rev.*, vol. 69(4), pp. 407-498 (1969).
Basha, et al., *Tetrahedron Letters*, vol. 18(48), pp. 4171-4172 (1977).
Witczak, et al., *Synlett*, vol 1996(1), p. 108-110 (1998).
Mazur, et al., *J. Org. Chem.*, vol, 62(13), 4471-4475 (1997).
Sebum, et al., *J. Molecular Catalysis B: Enzymatic*, vol. 41, pp. 141-145 (2006).
Angelin, et al., *Eur. J. Org. Chem.*, vol. 2006(19), pp. 4323-4326 (2006).
Deshpande, et al., *J. Org. Chem.*, vol. 72(25), pp. 9746-9749 (2007).
Czernecki, et al., *J. Org. Chem.*, vol. 56(22), pp. 6289-6292 (1991).
Barrett, et al., *J. Chem. Soc., Chem. Commun.*, vol. 11, pp. 1147-1148 (1995).
Xu, et al., *Bioorgenic & Medicinal Chemistry Letters*, vol. 19, pp. 5632-5635 (2009).
Borghese, et al., *Drug of the Future*, vol. 34(4), pp. 297-305 (2009).
Handlon, *Expert Opinion of Therapeutic Patents*, vol, 15, No. 11, pp, 1531-1540 (2005).
Asano, et al., *Drugs of the Future*, vol. 29(5), pp. 461-466 (2004).
Ellsworth, et al., *Bioorganic & Medicinal Chemistry Letters*, vol. 18(17), pp, 4770-4773 (2008).
Yamanoi, et al., *Synlett*, No. 19. pp. 2973-2977 (2005).
McGinnis, et al., *JAMA*, vol. 270(18), pp. 2207-2212 (1993).
Isaji, *Current Opinion Investigational Drug*, vol. 8(4), pp. 285-292 (2007).
Hanashima, et al., *Bioorganic & Medicinal Chemistry*, vol. 9, pp. 367-376 (2001).
Gent, et al., *Journal of the Chemical Society Perkin Transactions 1*, 1974, pp. 1835-1839.
Wessel, *Journal of Carbohydrate Chemistry*, vol. 7(1), pp. 263-269 (1988).
Yuasa, et al., *Organic Process Research & Development*, vol. 8, pp. 405-407 (2004).
Omura, et al., *Tetrahedron*, vol. 34(11), pp. 1651-1660 (1976).
Ozanne, et al., *Organic Letters*, vol. 5(16), pp. 2903-2906 (2003).
Schaffer, *Journal of the American Chemical Society*, vol. 81(20), pp. 5452-5454 (1959).

Amigues, et al., *Tetrahedron*, vol. 63(40), pp. 10042-10053 (2007).
Nahm, et al., *Tetrahedron Letters*, vol. 22(39), pp. 3815-3815 (1981).
Kornblum, et al., *Journal of the American Chemical Society*, vol. 81(15), pp. 4113-4114 (1959).
Zhang, et al., *Drug Discovery Today*, vol. 12(9-10), pp. 373-381 (2007).
Fabian, et al., *Crystal Growth & Design*, vol. 9(3), pp. 1436-1443 (2009).
Zhang, et al., *Journal of Pharmaceutical Sciences*, vol. 96(6), pp. 990-995 (2007).
Lv, et al., *Bioorganic & Medicinal Chemistry Letters*, vol. 19. pp. 6877-6861 (2009).
Washburn, *Expert Opin. Ther. Patents*, vol. 19(11), pp. 1485-1499 (2009).
Washburn, *J. Med. Chem*, vol. 52(7), pp. 1785-1794 (2009).
Derwent Abstract No. 2004-537322/52 (Re: Japanese Patent No. JP2004-196788).
Derwent Abstract No. 2005-643486/66 (Re: Japanese Patent No. JP2005-247634).
Derwent Abstract No. 2006-338277/35 (Re: Japanese Patent No. JP2006-117651).
Derwent Abstract No. 2003-486266/46 (Re: Japanese Patent No. JP2003-012686).
In Vitro Mammalian Cell Micronuleus Test (MNvit), Organization for Economic Co-Operation and Development (OECD) Draft Test Guideline (Draft TG) 487 (2007).
In vitro Mammalian chromosomal Aberration Test, OECD TG 473 (1997).
Bacterial Reverse Mutation Test. OECD TG 471 (1997).
Mammalian Erythrocyte Micronucleus Test, OECD TG 474 (1997).

DIOXA-BICYCLO[3.2.1]OCTANE-2,3,4-TRIOL DERIVATIVES

RELATED APPLICATIONS

This application claims the benefit of priority under 35 U.S.C. 119(e) of U.S. Provisional Application Ser. Nos. 61/092,470, filed Aug. 28, 2008, and 61/227,212, filed Jul. 21, 2009, both of which are incorporated herein by reference in their entireties for all purposes.

FIELD OF THE INVENTION

The present invention relates to dioxa-bicyclo[3.2.1]octane-2,3,4-triol derivatives, crystal structures, pharmaceutical compositions and the uses thereof as sodium-glucose co-transporter (SGLT) inhibitors.

BACKGROUND

Obesity is a significant health problem due to its serious medical complications that include co-morbidities such as hypertension, insulin resistance, diabetes, coronary artery disease and heart failure (collectively referred to as Metabolic Syndrome). Obesity and its related co-morbidities continue to cause rising health issues in the developed world and are beginning to affect the developing world as well. The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993). There is a need to identify and develop new medications that treat and/or prevent obesity and its associated co-morbidities, in particular type II (type 2) diabetes.

More recently, sodium-glucose co-transport (SGLT) inhibitors, particularly SGLT2 inhibitors, have been shown to block the reabsorption of glucose from the renal filtrate in the glomerulus thereby inducing glucose excretion in the urine. As excess glucose is excreted, there is a decrease in blood glucose level, decreased hepatic storage of glucose, decreased insulin secretion and, subsequently, decreased carbohydrate conversion to fat and, ultimately, reduced accumulated fat. Selective inhibition of SGLT2 is expected to normalize plasma glucose by enhancing glucose excretion. Consequently, SGLT2 inhibitors provide an attractive means for the improvement of diabetic conditions without increasing body weight or the risk of hypoglycemia. See, Isaji, M., *Current Opinion Investigational Drugs*, 8(4), 285-292 (2007). For a general review of SGLT as a therapeutic target, see also Asano, T., et al., *Drugs of the Future*, 29(5), 461-466 (2004).

Representative examples of glycosides that have been shown to be useful for the treatment of NIDDM and obesity can be found in the following disclosures: U.S. Pat. Nos. 6,515,117; 6,414,126; 7,101,856; 7,169,761; and 7,202,350; U.S. Publication Nos. US2002/0111315; US2002/0137903; US2004/0138439; US2005/0233988; US2006/0025349; US2006/0035841; and US2006/0632722; and PCT Publication Nos. WO01/027128; WO02/044192; WO02/088157; WO03/099836; WO04/087727; WO05/021566; WO05/085267; WO06/008038; WO06/002912; WO06/062224; WO07/000,445; WO07/093610; and WO08/002,824.

Certain glycosides are genotoxic and impact a cell's genetic material such that they may be potentially mutagenic or carcinogenic. Genotoxic materials may be detected using standard assays such as the In Vitro Mammalian Cell Micronucleus Test (MNvit), Organization for Economic Co-Operation and Development (OECD) Draft Test Guideline (Draft TG) 487 (2007); In vitro Mammalian Chromosomal Aberration Test, OECD TG 473 (1997); Bacterial Reverse Mutation Test, OECD TG 471 (1997); Mammalian Erythrocyte Micronucleus Test, OECD TG 474 (1997); or the like. Consequently, there still exists a need for a more effective and safe therapeutic treatment and/or prevention of obesity and its associated co-morbidities, in particular, Type 2 diabetes and related disorders.

SUMMARY

Compounds of Formula (A) and Formula (B) have been found to act as sodium-glucose cotransport (SGLT) inhibitors, in particular, SGLT2 inhibitors; therefore, may be used in the treatment of diseases mediated by such inhibition (e.g., diseases related to obesity, Type 2 diabetes, and obesity-related and diabetes-related co-morbidities). These compounds may be represented by Formulas (A) and (B) as shown below:

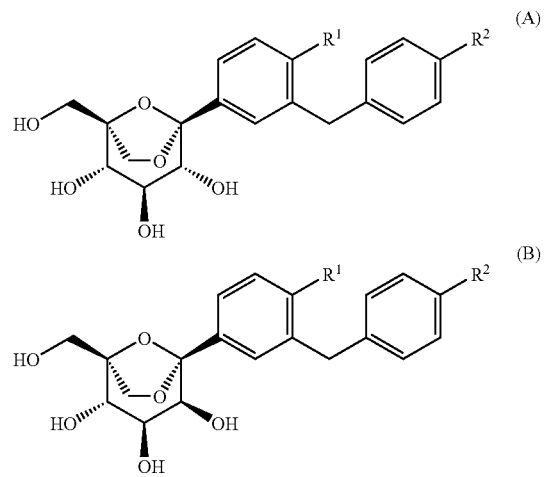

wherein $R^1$ is H, $(C_1-C_4)$alkyl, $(C_1-C_4)$alkoxy, Cl, F, cyano, fluoro-substituted $(C_1-C_2)$alkyl, $(C_1-C_4)$alkyl-$SO_2$—, or $(C_3-C_6)$cycloalkyl; and $R^2$ is $(C_1-C_4)$alkyl, $(C_1-C_4)$alkoxy, $(C_2-C_4)$alkynyl, 3-oxetanyloxy, 3-tetrahydrofuranyloxy, Cl, F, cyano, fluoro-substituted $(C_1-C_2)$alkyl, $(C_1-C_4)$alkyl-$SO_2$—, $(C_3-C_6)$cycloalkyl, or a $(C_5-C_6)$heterocycle having 1 or 2 heteroatoms each independently selected from N, O, or S.

It is generally understood by those skilled in the art that various substituents may be added to the compounds of Formula (A) or Formula (B) so long as the substituent(s) selected does not adversely affect the pharmacological characteristics of the compound or adversely interfere with the use of the medicament.

Specific compounds of Formula (A) include: (1S,2S,3S,4R,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4R,5S)-5-[3-(4-ethoxy-benzyl)-4-methyl-phenyl]-1-hydroxymethyl-6,8-dioxa-bicyclo[3.2.1]octane-2,3,4-triol; (1S,2S,3S,4R,5S)-5-[4-chloro-3-(4-methoxy-benzyl)-phenyl]-1-hydroxymethyl-6,8-dioxa-bicyclo[3.2.1]octane-2,3,4-triol; (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4R,5S)-5-[4-fluoro-3-(4-methoxy-benzyl)-phenyl]-1-hydroxymethyl-6,8-dioxa-bicyclo[3.2.1]

octane-2,3,4-triol; 2-(4-methoxybenzyl)-4-((1S,2S,3S,4R,5S)-2,3,4-trihydroxy-1-(hydroxymethyl)-6,8-dioxa-bicyclo[3,2,1]oct-5-yl)benzonitrile; 2-(4-ethoxybenzyl)-4-((1S,2S,3S,4R,5S)-2,3,4-trihydroxy-1-(hydroxymethyl)-6,8-dioxa-bicyclo[3,2,1]oct-5-yl)benzonitrile; (1S,2S,3S,4R,5S)-5-[3-(4-ethoxy-benzyl)-4-fluoro-phenyl]-1-hydroxymethyl-6,8-dioxa-bicyclo[3.2.1]octane-2,3,4-triol; (1S,2S,3S,4R,5S)-5-{4-fluoro-3-[4-(tetrahydro-furan-3-yloxy)-benzyl]-phenyl}-1-hydroxymethyl-6,8-dioxa-bicyclo[3.2.1]octane-2,3,4-triol; (1S,2S,3S,4R,5S)-5-[3-(4-chlorobenzyl)-4-fluorophenyl]-1-hydroxymethyl-6,8-dioxabicyclo[3.2.1]octane-2,3,4-triol; (1S,2S,3S,4R,5S)-5-{4-fluoro-3-[4-(oxetan-3-yloxy)-benzyl]-phenyl}-1-hydroxymethyl-6,8-dioxa-bicyclo[3.2.1]octane-2,3,4-triol; and (1S,2S,3S,4R,5S)-5-{4-chloro-3-[4-(oxetan-3-yloxy)-benzyl]-phenyl}-1-hydroxymethyl-6,8-dioxa-bicyclo[3.2.1]octane-2,3,4-triol.

Specific compounds of Formula (B) include: (1S,2S,3S,4S,5S)-1-hydroxymethyl-5-[3-(4-methoxy-benzyl)-4-methyl-phenyl]-6,8-dioxa-bicyclo[3.2.1]octane-2,3,4-triol; (1S,2S,3S,4S,5S)-5-[3-(4-ethoxy-benzyl)-4-methyl-phenyl]-1-hydroxymethyl-6,8-dioxa-bicyclo[3.2.1]octane-2,3,4-triol; (1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol; (1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol; (1S,2S,3S,4S,5S)-5-[4-fluoro-3-(4-methoxy-benzyl)-phenyl]-1-hydroxymethyl-6,8-dioxa-bicyclo[3.2.1]octane-2,3,4-triol; (1S,2S,3S,4S,5S)-5-[3-(4-ethoxy-benzyl)-4-fluoro-phenyl]-1-hydroxymethyl-6,8-dioxa-bicyclo[3.2.1]octane-2,3,4-triol; and (1S,2S,3S,4S,5S)-5-[3-(4-chlorobenzyl)-4-fluorophenyl]-1-hydroxymethyl-6,8-dioxabicyclo[3.2.1]octane-2,3,4-triol.

A further aspect of the present invention is a crystal comprising a compound having the formula (4A):

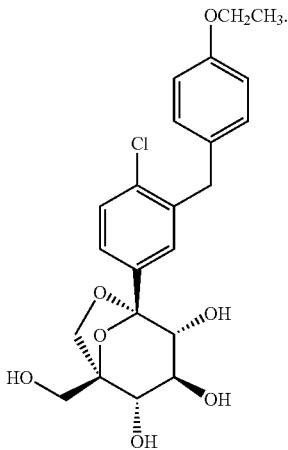

(4A)

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention, a method for treating a disease, disorder, or condition modulated by SGLT2 inhibition in animals is provided that includes the step of administering to an animal (preferably, a human) in need of such treatment a therapeutically effective amount of a compound of the present invention (or a pharmaceutical composition thereof). Diseases, conditions, and/or disorders modulated by SGLT2 inhibition include, e.g., Type II diabetes, diabetic nephropathy, insulin resistance syndrome, hyperglycemia, hyperinsulinemia, hyperlipidemia, impaired glucose tolerance, obesity (including weight control or weight maintenance), hypertension, and reducing the level of blood glucose.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

It is to be understood that both the foregoing general description and the following detailed description are exemplary and explanatory only and are not restrictive of the invention, as claimed.

DETAILED DESCRIPTION

Figure 1:
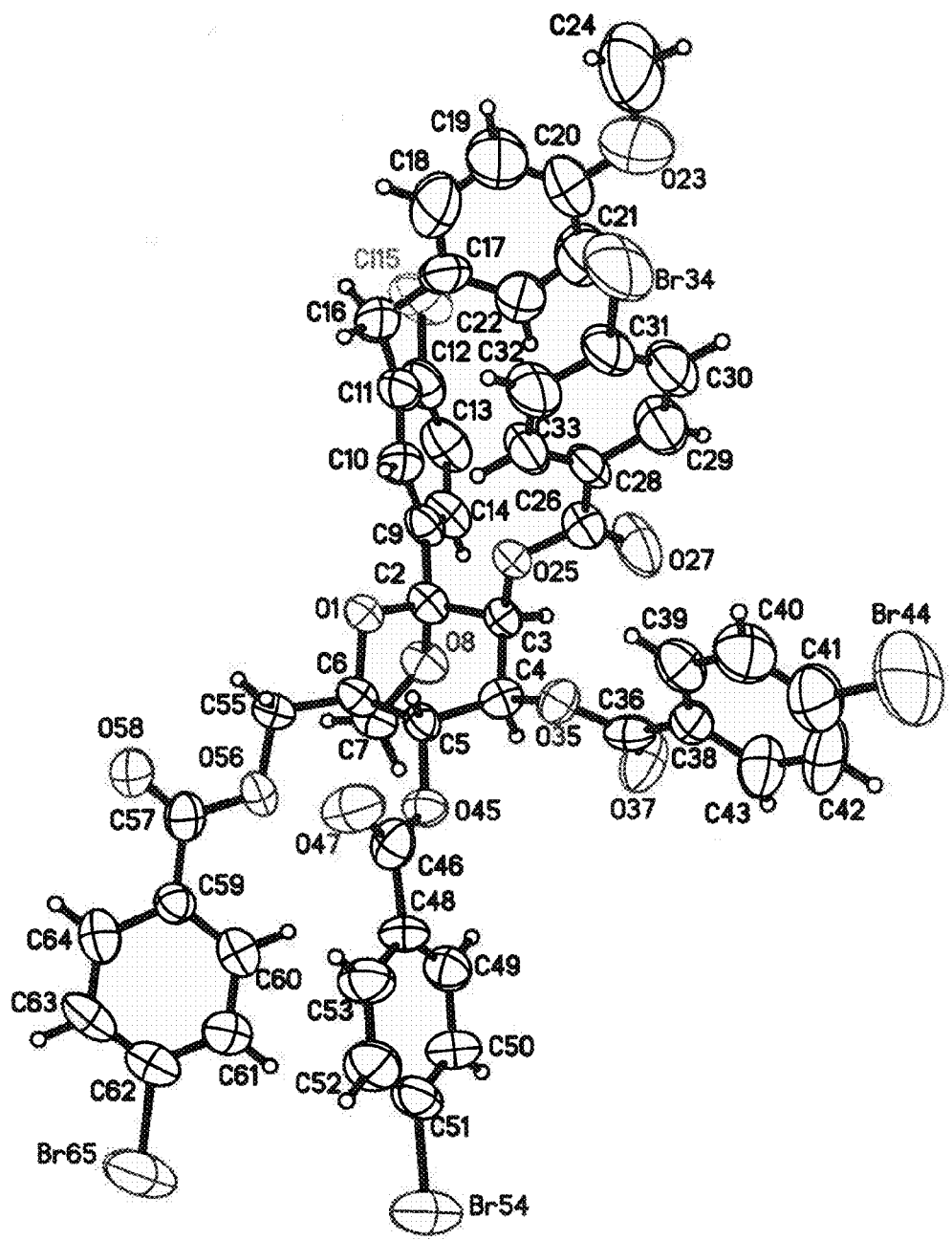
FIG. 1 represents the refined crystal structure for the Example 8A compound which was plotted using the SHELXTL plotting package.

The present invention may be understood even more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting. The plural and singular should be treated as interchangeable, other than the indication of number:

As used herein, the term "alkyl" refers to a hydrocarbon radical of the general formula $C_nH_{2n+1}$. The alkane radical may be straight or branched. For example, the term "$(C_1$-$C_6)$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, 1,1-difluoroethyl and the like).

The term "cycloalkyl" refers to nonaromatic rings that are fully hydrogenated and may exist as a single ring, bicyclic ring or a spiro ring. Unless specified otherwise, the carbocyclic ring is generally a 3- to 8-membered ring. For example, cycloalkyl include groups such as cyclopropyl, cyclobutyl, cyclopentyl, cyclohexyl, cyclohexenyl, norbornyl (bicyclo[2.2.1]heptyl), bicyclo[2.2.2]octyl, and the like.

The term "heterocycle" refers to nonaromatic rings that are fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholino, thiomorpholino, tetrahydrothienyl, tetrahydrothienyl 1,1-dioxide, and the like.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the sodium-glucose transporter (in particular, SGLT2) with compounds of the present invention thereby partially or fully preventing glucose transport across the transporter.

The term "compounds of the present invention" (unless specifically identified otherwise) refer to compounds of Formula (A), Formula (B) and all pure and mixed stereoisomers (including diastereoisomers and enantiomers), tautomers and isotopically labeled compounds. Hydrates and solvates of the compounds of the present invention are considered compositions of the present invention, wherein the compound is in association with water or solvent, respectively. The compounds may also exist in one or more crystalline states, i.e. as co-crystals, polymorphs, or they may exist as amorphous solids. All such forms are encompassed by the claims.

In one embodiment, $R^1$ is H, methyl, ethyl, propyl, isopropyl, methoxy, ethoxy, F, Cl, cyano, —$CF_3$, cyclopropyl, or cyclobutyl. In another embodiment, $R^1$ is H, methyl, ethyl, isopropyl, methoxy, ethoxy, F, Cl, cyano, —$CF_3$, or cyclopropyl. In a further embodiment, $R^1$ is H, methyl, ethyl, methoxy, ethoxy, F, Cl, cyano, —$CF_3$, or cyclopropyl. In yet a further embodiment, $R^1$ is methyl, ethyl, F, Cl, cyano, $CF_3$, or cyclopropyl.

In one embodiment, $R^2$ is methyl, ethyl, propyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In another embodiment, $R^2$ is methyl, ethyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl. In a further embodiment, $R^2$ is methyl, ethyl, methoxy, ethoxy, F, Cl, cyano, —$CF_3$, —$CF_2CH_3$, ethynyl, 3-oxetanyloxy, 3-tetrahydrofuranyloxy, or cyclopropyl. In yet a further embodiment, $R^2$ is methoxy or ethoxy.

In one embodiment, the crystal comprises the compound 4A and L-proline or L-pyroglutamic acid.

In a further embodiment, the crystal has one or more of the following:

a) space group of P2(1)2(1)2(1) and unit cell parameters substantially equal to the following:
    a=7.4907(10) Å α=90°.
    b=12.8626(15) Å β=90°.
    c=28.029(4) Å γ=900;

b) a powder x-ray diffraction pattern comprising 2-theta values of (CuKα radiation, wavelength of 1.54056 Å) 6.4±0.2, 16.7±0.2, 17.4±0.2 and 21.1±0.2;

c) a solid state 13C NMR spectrum having peak positions at 16.5±0.2, 131.1±0.2, 158.7±0.2, and 181.5±0.2 ppm as determined on a 500 MHz spectrometer relative to crystalline adamantine of 29.5 ppm; or d) a differential scanning calorimetry thermogram having an endotherm of about 142.5±2° C.

In a further embodiment, the crystal is a co-crystal comprising the compound of formula (4A) and L-pyroglutamic acid in a 1:1 stoichiometric ratio.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality of intermediates may be necessary. The need for such protection will vary depending on the nature of the remote functionality and the conditions of the preparation methods. A "hydroxy-protecting group" refers to a substituent of a hydroxy group that blocks or protects the hydroxy functionality. Suitable hydroxyl-protecting groups (O-Pg) include for example, allyl, acetyl (Ac), silyl (like trimethylsilyl (TMS) or tert-butyldimethylsilyl (TBS)), benzyl (Bn), para-methoxybenzyl (PMB), trityl (Tr), para-bromobenzoyl, para-nitrobenzoyl and the like (benzylidene for protection of 1,3-diols). The need for such protection is readily determined by one skilled in the art. For a general description of protecting groups and their use, see T. W. Greene, *Protective Groups in Organic Synthesis*, John Wiley & Sons, New York, 1991.

Scheme 1 outlines the general procedures one could use to provide compounds of the present invention.

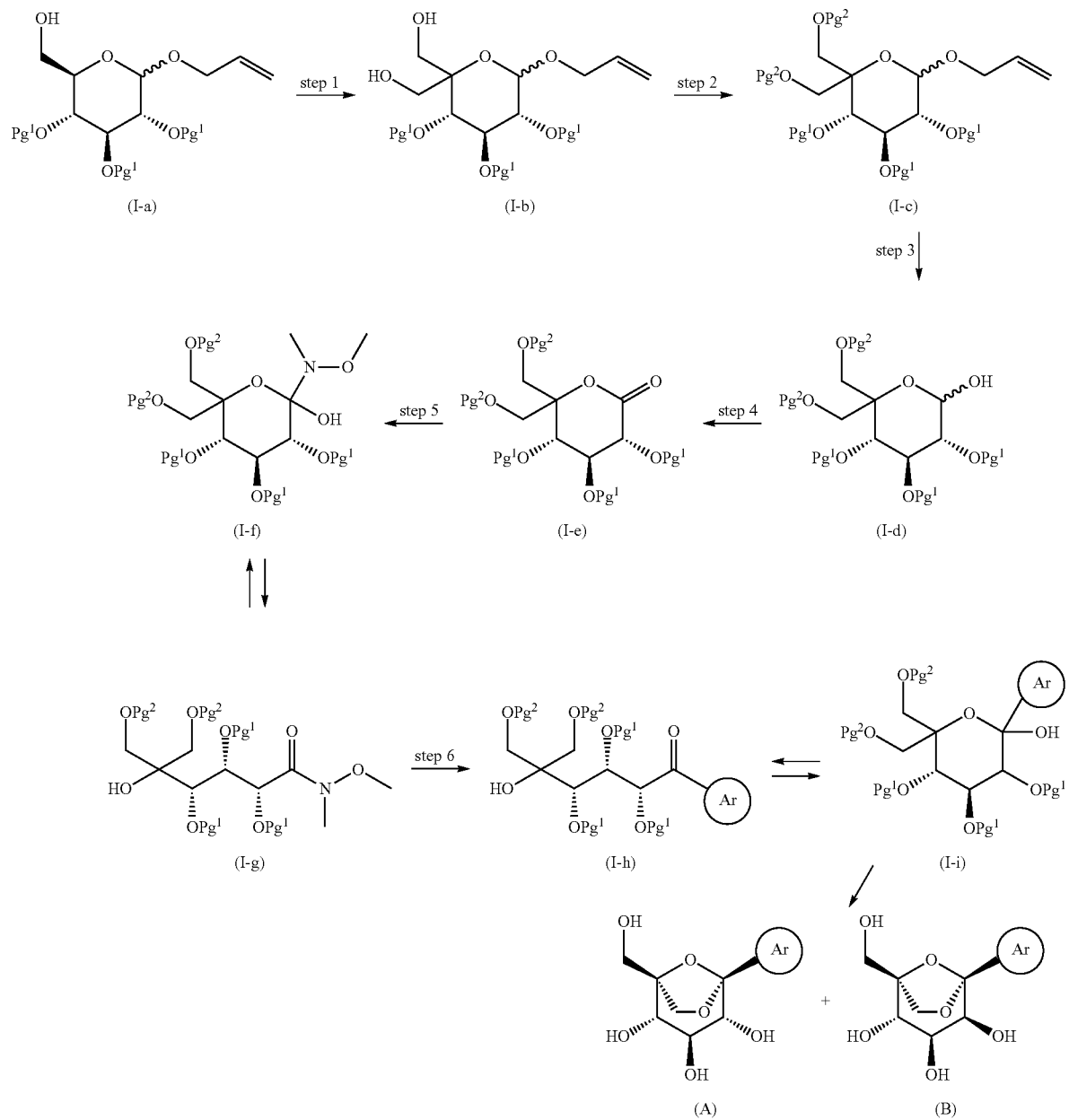

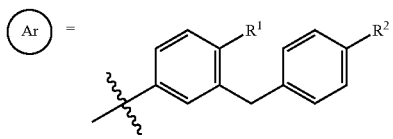

Allyl 2,3,4-tri-O-benzyl-D-glucopyranoside (I-a, where $Pg^1$ is a benzyl group) can be prepared by procedures described by Shinya Hanashima, et al., in *Bioorganic & Medicinal Chemistry*, 9, 367 (2001); Patricia A. Gent et al. in *Journal of the Chemical Society, Perkin* 1, 1835 (1974); Hans Peter Wessel in the *Journal of Carbohydrate Chemistry*, 7, 263, (1988); or Yoko Yuasa, et al., in *Organic Process Research & Development*, 8, 405-407 (2004). In step 1 of Scheme 1, the hydroxymethylene group can be introduced onto the glycoside by means of a Swern oxidation followed by treatment with formaldehyde in the presence of an alkali metal hydroxide (e.g., sodium hydroxide). This is referred to as an aldol-Cannizzaro reaction. The Swern oxidation is described by Kanji Omura and Daniel Swern in *Tetrahedron*, 34, 1651 (1978). Modifications of this process known to those of skill in the art may also be used. For example, other oxidants, like stabilized 2-iodoxybenzoic acid described by Ozanne, A. et al. in *Organic Letters*, 5, 2903 (2003), as well as other oxidants known by those skilled in the art can also be used. The aldol Cannizzaro sequence has been described by Robert Schaffer in the *Journal of The American Chemical Society*, 81, 5452 (1959) and Amigues, E. J., et al., in *Tetrahedron*, 63, 10042 (2007).

In step 2 of Scheme 1, protecting groups ($Pg^2$) can be added by treating intermediate (I-b) with the appropriate reagents and procedures for the particular protecting group desired. For example, p-methoxybenzyl (PMB) groups may be introduced by treatment of intermediate (I-b) with p-methoxybenzyl bromide or p-methoxybenzyl chloride in the presence of sodium hydride, potassium hydride, potassium tert-butoxide in a solvent like tetrahydrofuran, 1,2-dimethoxyethane or N,N-dimethylformamide (DMF). Conditions involving para-methoxybenzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used. Benzyl (Bn) groups may be introduced by treatment of intermediate (I-b) with benzyl bromide or benzyl chloride in the presence of sodium hydride, potassium hydride, potassium tert-butoxide in a solvent like tetrahydrofuran, 1,2-dimethoxyethane or N,N-dimethylformamide. Conditions involving benzyltrichloroacetimidate in presence of a catalytic amount of acid (e.g., trifluoromethanesulfonic acid, methanesulfonic acid, or camphorsulfonic acid) in a solvent such as dichloromethane, heptane or hexanes can also be used.

In step 3 of Scheme 1, the allyl protection group is removed (e.g., by treatment with palladium chloride in methanol; cosolvent like dichloromethane may also be used; other conditions known by those skilled in the art could also be used, see T. W. Greene, *Protective Groups in Organic Synthesis*, John Wiley & Sons, New York, 1991) to form the lactol (I-d).

In step 4 of Scheme 1, oxidation of the unprotected hydroxyl group to an oxo group (e.g., Swern oxidation) then forms the lactone (I-e).

In step 5 of Scheme 1, the lactone (I-e) is reacted with N,O-dimethyl hydroxylamine hydrochloride to form the corresponding Weinreb amide which may exist in equilibrium in a closed/opened form. (I-f/I-g). The "Weinreb amide" (I-g) can be made using procedures well known to those of skill in the art. See, Nahm, S., and S. M. Weinreb, *Tetrahedron Letters*, 22 (39), 3815-1818 (1981). For example, intermediate (1-f/1-a) can be prepared from the commercially available N,O-dimethylhydroxylamine hydrochloride and an activating agent (e.g., trimethylaluminum).

In step 6 of Scheme 1, the arylbenzyl group (Ar) is introduced using the desired organometallic reagent (e.g., organo lithium compound (ArLi) or organomagnesium compound (ArMgX)) in tetrahydrofuran (THF) at a temperature ranging from about −78° C. to about 20° C. followed by hydrolysis (upon standing in protic conditions) to the corresponding lactol (I-i) which may be in equilibrium with the corresponding ketone (I-h). The bridged ketal motif found in (A) and (B) can be prepared by removing the protecting groups ($Pg^2$) using the appropriate reagents for the protecting groups employed. For example, the PMB protecting groups may be removed by treatment with trifluoroacetic acid in the presence of anisole and dichloromethane (DCM) at about 0° C. to about 23° C. (room temperature). The remaining protecting groups ($Pg^1$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final products (A) and (B). When $R^1$ is CN, the use of a Lewis acid like boron trichloride at a temperature ranging from about −78° C. to about room temperature in a solvent like dichloromethane or 1,2-dichloroethane may also be used to remove benzyl protective and/or para-methoxybenzyl protective groups.

When $R^1$ is CN and $R^2$ is ($C_1$-$C_4$)alkoxy in intermediate (I-i) or in products (A) or (B), upon treatment with a Lewis acid such as boron trichloride or boron tribomide, partial to complete de-alkylation to the corresponding phenol may occur to lead to the corresponding compound (A) or (B) where $R^1$ is CN and $R^2$ is OH. If this occurs, the ($C_1$-$C_4$) alkoxy group may be re-introduced via selective alkylation using a ($C_1$-$C_4$) alkyl iodide under mildly basic conditions, for example, potassium carbonate in acetone at a temperature ranging from about room temperature to about 56 degrees Celsius.

When $R^1$ and/or $R^2$ is ($C_1$-$C_4$)alkyl-$SO_2$— it is understood by one skilled in the art that the organometallic addition step 6 (Scheme 1) will be carried out on the corresponding ($C_1$-$C_4$)alkyl-S— containing organometallic reagent. The thio-alkyl is then oxidized at a later stage to the corresponding sulfone using conventional methods known by those skilled in the art.

The compounds of the present invention may be prepared as co-crystals using any suitable method. A representative scheme for preparing such co-crystals is described in Scheme 2.

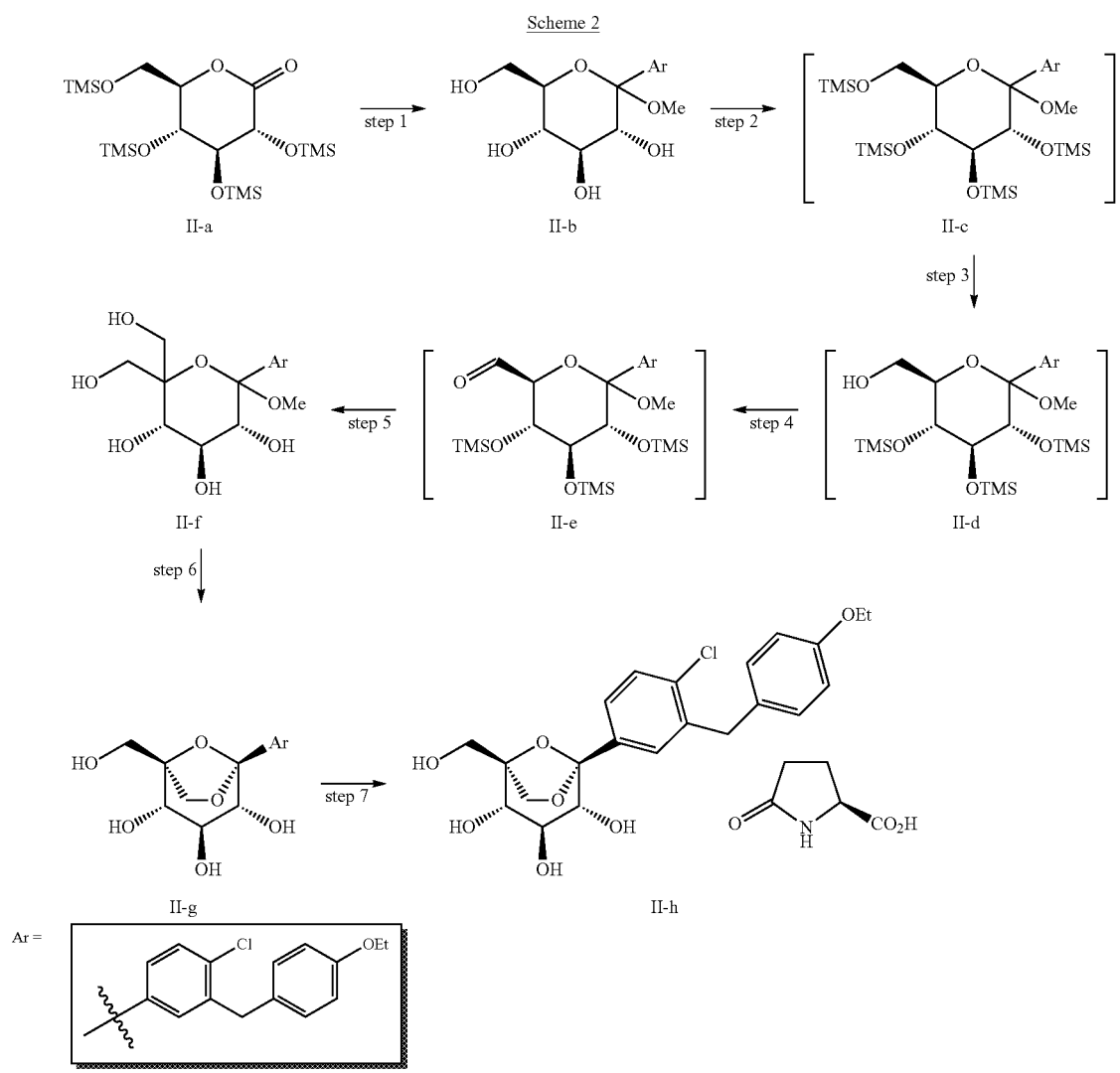

In Scheme 2, wherein Me is methyl and Et is ethyl, in step 1, 1-(5-bromo-2-chlorobenzyl)-4-ethoxybenzene is dissolved in 3:1, toluene: tetrahydrofuran followed by cooling the resulting solution to <−70° C. To this solution is added hexyllithium while maintaining the reaction at ≦−65° C. followed by stirring for 1 hour. (3R,4S,5R,6R)-3,4,5-tris(trimethylsilyloxy)-6-((trimethylsilyloxy)methyl)-tetrahydropyran-2-one (II-a) is dissolved in toluene and the resulting solution is cooled to −15° C. This solution is then added to the −70° C. aryllithium solution followed by stirring for 1 hour. A solution of methanesulfonic acid in methanol is then added followed by warming to room temperature and stirring for 16 to 24 hours. The reaction is deemed complete when the α-anomer level is ≦3%. The reaction is then basified by the addition of 5 M aqueous sodium hydroxide solution. The resulting salts are filtered off followed by concentration of the crude product solution. 2-methyltetrahydrofuran is added as a co-solvent and the organic phase is extracted twice with water. The organic phase is then concentrated to 4 volumes in toluene. This concentrate is then added to a 5:1, heptane: toluene solution causing precipitate to form. The solids are collected and dried under vacuum to afford a solid.

In step 2 of Scheme 2, to (II-b) in methylene chloride is added imidazole followed by cooling to 0° C. and then addition of trimethylsilylchloride to give the persilylated product. The reaction is warmed to room temperature and quenched by the addition of water, and the organic phase is washed with water. This crude methylene chloride solution of (II-c) is dried over sodium sulfate and then taken on crude into the next step.

In step 3 of Scheme 2, the crude solution of (II-c) in methylene chloride is concentrated to low volume and then the solvent is exchanged to methanol. The methanol solution of (II-c) is cooled to 0° C., then 1 mol % of potassium carbonate is added as a solution in methanol followed by stirring for 5 hours. The reaction is then quenched by addition of 1 mol % acetic acid in methanol, followed by warming to room temperature, solvent exchange to ethyl acetate, and then filtration of the minor amount of inorganic solids. The crude ethyl acetate solution of (II-d) is taken directly into the next step.

In step 4 of Scheme 2, the crude solution of (II-d) is concentrated to low volume, then diluted with methylene chloride and dimethylsulfoxide. Triethylamine is added followed by cooling to 10° C. and then sulfur trioxide pyridine complex is added in 3 portions as a solid at 10 minute intervals. The reaction is stirred an additional 3 hours at 10° C. before quenching with water and warming to room temperature. The phases are separated followed by washing the methylene chloride layer with aqueous ammonium chloride. The crude methylene chloride solution of (II-e) is taken directly into the next step.

In step 5 of Scheme 2, the crude solution of (II-e) is concentrated to low volume and then the solvent is exchanged to ethanol. Thirty equivalents of aqueous formaldehyde is added followed by warming to 55° C. An aqueous solution of 2 equivalents of potassium phosphate, tribasic is added followed by stirring for 24 hours at 55° C. The reaction temperature is then raised to 70° C. for an additional 12 hours. The reaction is cooled to room temperature, diluted with tert-butyl methyl ether and brine. The phases are separated followed by solvent exchange of the organic phase to ethyl acetate. The ethyl acetate phase is washed with brine and concentrated to low volume. The crude concentrate is then purified by silica gel flash chromatography eluting with 5% methanol, 95% toluene. Product containing fractions are combined and concentrated to low volume. Methanol is added followed by stirring until precipitation occurs. The suspension is cooled and the solids are collected and rinsed with heptane followed by drying. Product (II-f) is isolated as a solid.

In step 6 of Scheme 2, compound (II-f) is dissolved in 5 volumes of methylene chloride followed by the addition of 1 mol % SiliaBond® tosic acid and stirring for 18 hours at room temperature. The acid catalyst is filtered off and the methylene chloride solution of (II-g) is taken directly into the next step co-crystallization procedure.

In step 7 of Scheme 2, the methylene chloride solution of (II-g) is concentrated and then the solvent is exchanged to 2-propanol. Water is added followed by warming to 55° C. An aqueous solution of L-pyroglutamic acid is added followed by cooling the resulting solution to room temperature. The solution is then seeded and granulated for 18 hours. After cooling, the solids are collected and rinsed with heptane followed by drying. Product (II-h) is isolated as a solid.

An alternative synthesis route for compounds (A) of the present invention is depicted in Scheme 3 and described below.

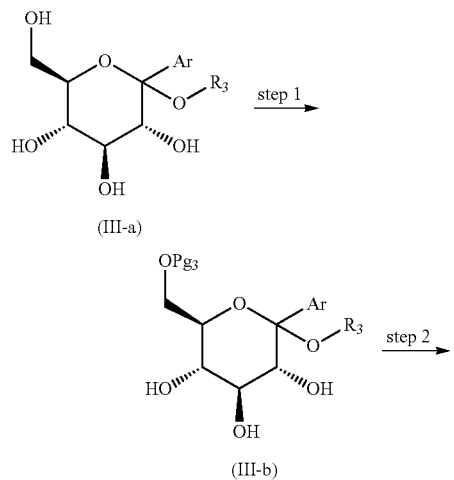

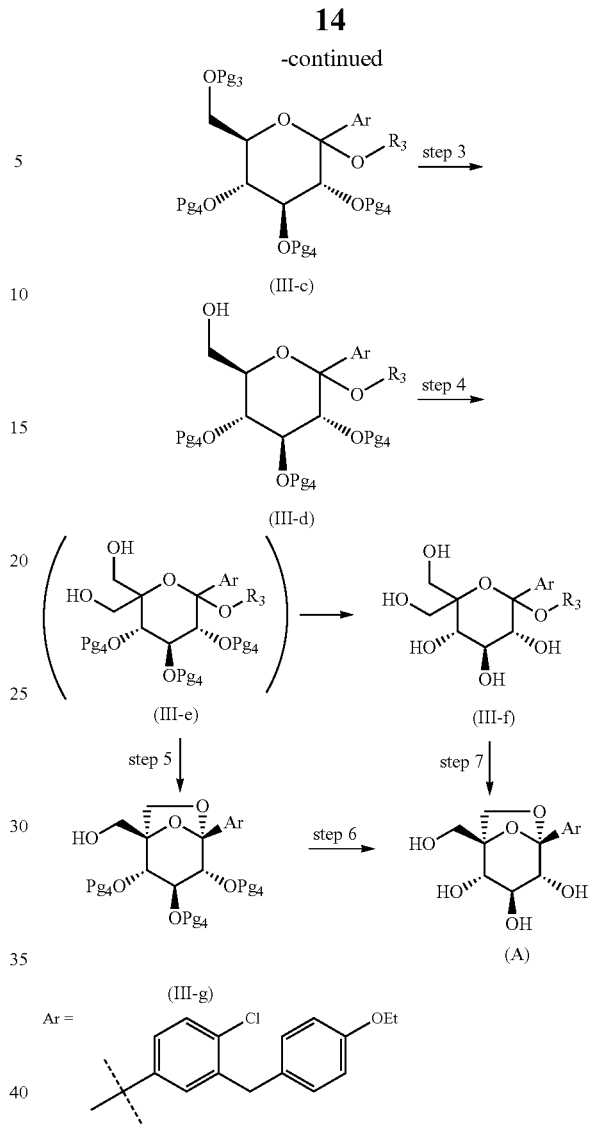

The synthesis of (III-a), where $R_3$ is an alkyl or fluoro substituted alkyl (except for the carbon adjacent to the oxygen atom) can be prepared in a similar way as described in step 1 of Scheme 2. In step 1 of Scheme 3, the primary hydroxyl group is selectively protected by an appropriate protective group. For example, a trityl group ($Pg_3$=Tr) can be introduced by treatment of intermediate (III-a) with chlorotriphenylmethane in presence of a base like pyridine in a solvent like toluene, tetrahydrofuran or dichloromethane at a temperature ranging from about 0 degrees Celsius to about room temperature. Additional examples of such protective groups and experimental conditions are known by those skilled in the art and can be found in T. W. Greene, *Protective Groups in Organic Synthesis*, John Wiley & Sons, New York, 1991.

In step 2 of Scheme 3, the secondary hydroxyl groups can be protected by the appropriate protecting groups. For example, benzyl groups ($Pg_4$ is Bn) can be introduced by treatment of intermediate (III-b) with benzyl bromide or benzyl chloride in the presence of sodium hydride, potassium hydride, potassium tert-butoxide in a solvent like tetrahydrofuran, 1,2-dimethoxyethane or N,N-dimethylformamide at a temperature ranging from about 0 degrees Celsius to about 80 degrees Celsius. Acetyl or benzoyl groups ($Pg_4$=Ac or Bz) may be introduced by treatment of intermediate (III-b) with acetyl chloride, acetyl bromide or acetic anhydride or benzoyl chloride or benzoic anhydride in the presence of a base like triethylamine, N,N-diisopropylethylamine or 4-(dimethylamino)pyridine in a solvent like tetrahydrofuran, 1,2-dimethoxyethane or dichloromethane at a temperature ranging from about 0 degrees Celsius to about 80 degrees Celsius.

In step 3 of Scheme 3, the primary hydroxyl group is deprotected to lead to intermediate (III-d). When Pg$_3$ is Tr, intermediate (III-c) is treated in the presence of an acid like para-toluenesulfonic acid in a alcoholic solvent like methanol at a temperature ranging from about −20 degrees Celsius to about room temperature to provide intermediate (III-d). Cosolvents like chloroform may be used.

In step 4 of Scheme 3, a hydroxymethylene group is introduced through a process similar to the one already described in Scheme 1 (step 1) and Scheme 2 (steps 4 and 5). Other sources of formaldehyde, like paraformaldehyde in a solvent like ethanol at a temperature ranging from about room temperature to about 70 degrees Celsius in the presence of an alkali metal alkoxide can also be used in this step. When Pg$_4$ is Bn, this step provides intermediate (III-e) and when Pg$_4$ is Ac or Bz, this step provides intermediate (III-f).

In step 5 of Scheme 3, intermediate (III-e) is treated with an acid like trifluoroacetic acid or an acidic resin in a solvent like dichloromethane at a temperature ranging from about −10 degrees Celsius to about room temperature to produce intermediate (III-g).

In step 6 of Scheme 3, the remaining protecting groups (Pg$_4$) may then be removed using the appropriate chemistry for the particular protecting groups. For example, benzyl protecting groups may be removed by treating with formic acid in the presence of palladium (Pd black) in a protic solvent (e.g., ethanol/THF) at about room temperature to produce the final product (A).

In step 7 of Scheme 3, intermediate (III-f) is treated with an acid like trifluoroacetic acid or an acidic resin in a solvent like dichloromethane at a temperature ranging from about −10 degrees Celsius to about room temperature to produce the final product (A).

Another alternative scheme for synthesizing product (A) is depicted in Scheme 4 and described below.

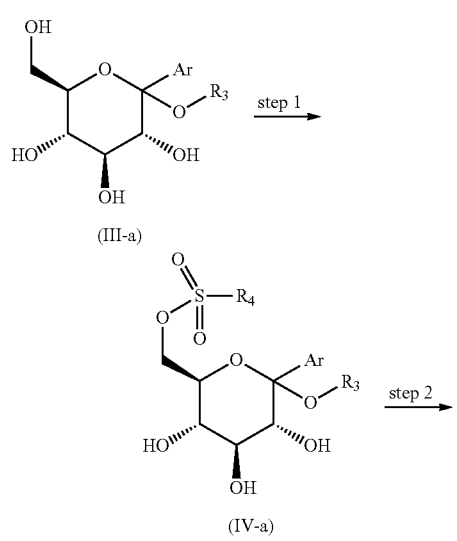

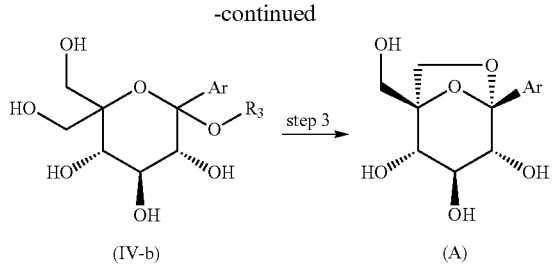

In step 1 of Scheme 4, intermediate (III-a) is treated with the appropriate arylsulfonyl chloride R$_4$SO$_2$Cl or arylsulfonic anhydride R$_4$S(O)$_2$OS(O)$_2$R$_4$ (wherein R$_4$ is an optionally substituted aryl group, such as found in the arylsulfonyl chlorides 4-methyl-benzenesulfonyl chloride, 4-nitro-benzenesulfonyl chloride, 4-fluoro-benzenesulfonyl chloride, 2,6-dichloro-benzenesulfonyl chloride, 4-fluoro-2-methyl-benzenesulfonyl chloride, and 2,4,6-trichloro-benzenesulfonyl chloride, and in the arylsulfonic anhydride, p-toluenesulfonic anhydride) in presence of a base like pyridine, triethylamine, N,N-diisopropylethylamine in a solvent like tetrahydrofuran, 2-methyltetrahydrofuran at a temperature ranging from about −20 degrees Celsius to about room temperature. Some Lewis acids like zinc(II) bromide may be used as additives.

In step 2 of Scheme 4, intermediate (IV-a) is submitted to a Kornblum-type oxidation (see, Kornblum, N., et al., *Journal of The American Chemical Society*, 81, 4113 (1959)) to produce the corresponding aldehyde which may exist in equilibrium with the corresponding hydrate and/or hemiacetal form. For example intermediate (IV-a) is treated in the presence of a base like pyridine, 2,6-lutidine, 2,4,6-collidine, N,N-diisopropylethylamine, 4-(dimethylamino)pyridine in a solvent like dimethyl sulfoxide at a temperature ranging from about room temperature to about 150 degrees Celsius. The aldehyde intermediate produced is then submitted to the aldol/Cannizzaro conditions described for step 1 (Scheme 1) and step 5 (Scheme 2) to produce intermediate (IV-b).

In step 3 of Scheme 4, intermediate (IV-b) is treated with an acid like trifluoroacetic acid or an acidic resin in a solvent like dichloromethane at a temperature ranging from about −10 degrees Celsius to about room temperature to produce the final product (A).

When R$^2$ is (C$_2$-C$_4$)alkynyl the process may be performed using Scheme 5, wherein R$^6$ is H or (C$_1$-C$_2$)alkyl.

Scheme 5
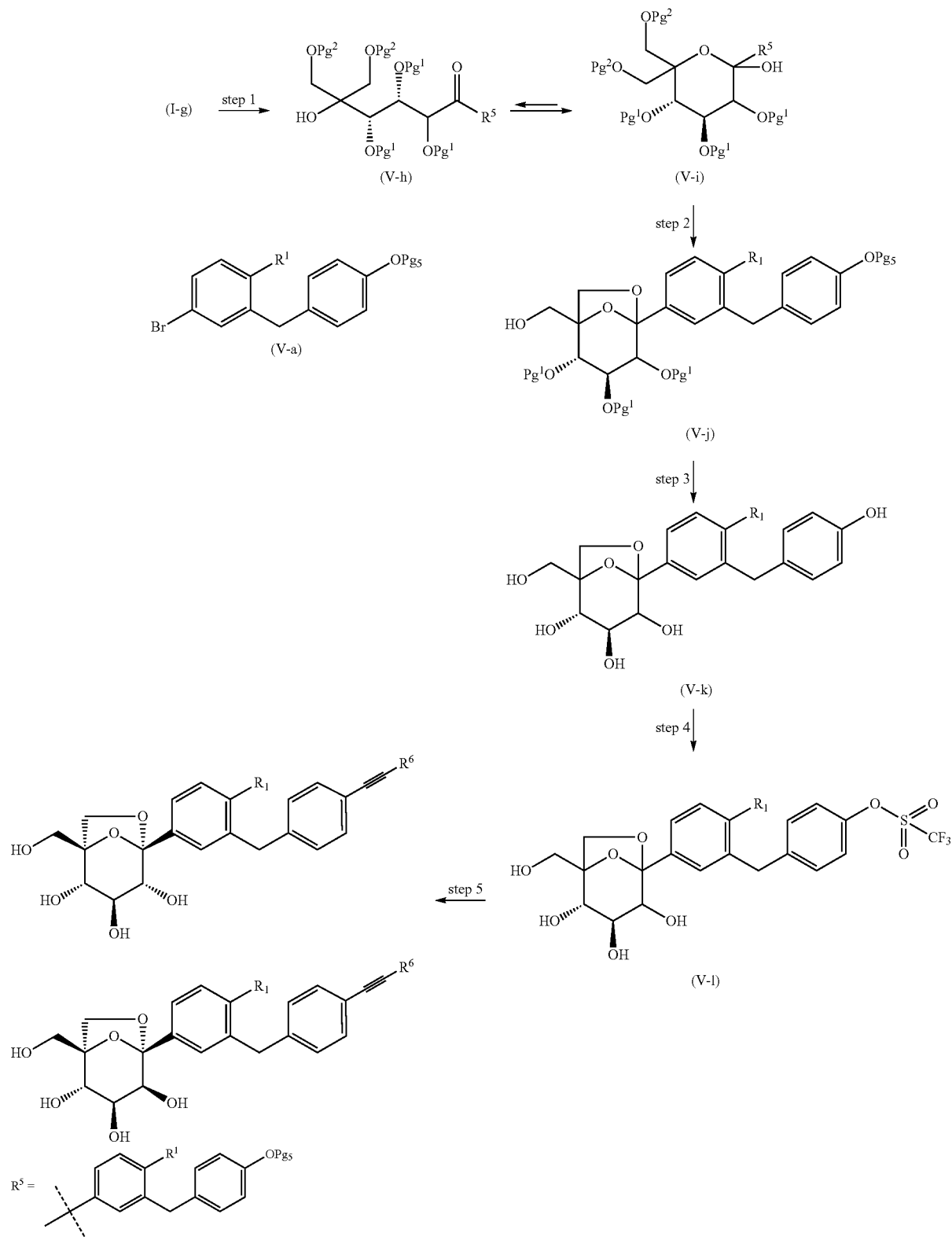
In step 1 of Scheme 5, which provides intermediate (V-i), the organometallic addition step is carried out in a similar way to the one described in Scheme 1, step 6, using the organo- metallic reagent derived from (V-a), where $Pg_5$ is a suitable protective group for the hydroxyl group. For instance $Pg_5$ can be a tertbutyldimethylsilyl group (TBS) (see US2007/

0054867 for preparation of for instance {4-[(5-bromo-2-chloro-phenyl)-methyl]-phenoxy}-tertbutyl-dimethyl-silane).

In step 2 of Scheme 5, when $Pg^2$=PMB, intermediate (V-i) is treated with an acid like trifluoroacetic acid, methanesulfonic acid or an acidic resin in presence of anisole in a solvent like dichloromethane at a temperature ranging from about −10 degrees Celsius to about room temperature to produce intermediate (V-j).

In step 3 of Scheme 5, protecting groups ($Pg_5$) and ($Pg^1$) can be removed to provide (V-k). Typically ($Pg_5$) is TBS and $Pg^1$ is Bn. In this circumstance, the protecting groups are removed by sequential treatment of (V-j) with 1) tetrabutylammonium fluoride in a solvent like tetrahydrofuran or 2-methyltetrahydrofuran at a temperature ranging from 0 degrees Celsius to about 40 degrees Celsius and 2) treatment with formic acid in the presence of palladium (Pd black) in a protic solvent (e.g., ethanol/THF) at about room temperature. In this sequence, the order of the 2 reactions is interchangeable.

In step 4 of Scheme 5, intermediate (V-k) is treated with N,N-bis-(trifluoromethanesulfonyl)-aniline in presence of a base like triethylamine or 4-dimethylaminopyridine in a solvent like dichloromethane or 1,2-dichloroethane at a temperature ranging from 0 degrees Celsius to about 40 degrees Celsius to produce intermediate (V-I).

In step 5 of Scheme 5, intermediate (V-I) is subjected to a Sonogashira-type reaction (see, Sonogashira, K. Coupling Reactions Between $sp^2$ and sp Carbon Centers. In *Comprehensive Organic Synthesis* (eds. Trost, B. M., Fleming, I.), 3, 521-549, (Pergamon, Oxford, 1991)). For instance (V-I) is treated with the appropriate terminal alkyne $HCCR^6$ in presence of copper(I) iodide, a catalyst like bis-(triphenylphosphine)-palladium dichloride or tetrakis(triphenylphosphine) palladium(0) in presence of a base like triethylamine or N,N-diisopropylethylamine in a solvent like N,N-dimethylformamide at a temperature ranging from about room temperature to about 120 degrees Celsius to produce the desired product (A) and (B). When $R^6$ is H, it is more convenient to use trimethylsilylacetylene. In this case the crude material obtained from the reaction described above is treated with a base like potassium carbonate in an alcoholic solvent like MeOH at about room temperature to produce after classical work-up known by those skilled in the art the desired product (A) and (B) where $R^2$ is —CCH.

One skilled in the art would understand that the chemistry described above in schemes 1 to 5, represents different ways of accessing intermediate (V-k). In turn, particularly when $R^1$ is Cl, (V-k) can be treated with an alkylating agent of choice under classical conditions to selectively alkylate the phenol group to produce (A) (and (B) in schemes 1 and 5) where $R^2$ is ($C_1$-$C_4$)alkoxy.

The compounds of the present invention contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization, distillation, sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC (high pressure liquid chromatography) column.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by the inhibition of the sodium-glucose transporters (in particular SGLT2); therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula (I). The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002,824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of sodium-glucose transporters in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of SGLT2.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, delayed wound healing, hyperinsulinemia, elevated blood levels of fatty acids, hyperlipidemia, hypertriglyceridemia, Syndrome X, increased high density lipoprotein levels, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005).

Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, anti-inflammatory agents and anti-hypertensive agents.

Suitable anti-obesity agents include cannabinoid-1 (CB-1) antagonists (such as rimonabant), 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include CB-1 antagonists (e.g., rimonabant, taranabant, surinabant, otenabant, SLV319 (CAS No. 464213-10-3) and AVE1625 (CAS No. 358970-97-5)), gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6, 10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoylestrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

Suitable anti-diabetic agents include an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, a VPAC2 receptor agonist and a glucokinase activator. Preferred anti-diabetic agents are metformin and DPP-IV inhibitors (e.g., sitagliptin, vildagliptin, alogliptin and saxagliptin).

Suitable anti-inflammatory agents include genital tract/urinary tract infection preventatives and treatments. Exemplary agents include cranberries (i.e. *Vaccinium macrocarpon*) and cranberry derivatives such as cranberry juice, cranberry extracts or flavonols of cranberries. Cranberry extracts may include one or more flavonols (i.e. anthocyanins and proanthocyanidins) or a purified cranberry flavonol compound, including myricetin-3-β-xylopyranoside, quercetin-3-β-glucoside, quercetin-3-α-arabinopyranoside, 3'-methoxyquercetin-3-α-xylopyranoside, quercetin-3-O-(6"-p-coumaroyl)-β-galactoside, quercetin-3-O-(6"-benzoyl)-β-galactoside, and/or quercetin-3-α-arabinofuranoside.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), and Accela ChemBio (San Diego, Calif.).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (delta) relative to residual solvent as an internal reference. The peak shapes are denoted as follows: s, singlet; d, doublet; dd, doublet of doublet; t, triplet; q, quartet; m, multiplet; bs or br.s., broad singlet; 2s, two singlets; br.d., broad doublet. Electrospray ionization mass spectra (ES) were obtained on a Waters™ ZMD instrument (carrier gas: nitrogen; solvent A: water/0.01% formic acid, solvent B: acetonitrile/0.005% formic acid; available from Waters Corp., Milford, Mass.). High resolution mass spectra (HRMS) were obtained on an Agilent™ Model 6210 time of flight. Where the intensity of single chlorine or single bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given.

Column chromatography was performed with either Baker™ silica gel (40 microm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.). MPLC (medium pressure liquid chromatography) was performed using a Biotage™ SP purification system or a Combiflash® Companion® from Teledyne™ Isco™; Biotage™ SNAP cartridge KPsil or Redisep Rf silica (from Teledyne™ Isco™) under low nitrogen pressure were used. HPLC (high pressure liquid chromatography) was performed using a Shimadzu™ 10A LC-UV or a Agilent™ 1100 preparatory HPLC.

Except where otherwise noted, all reactions were run under an inert atmosphere of nitrogen gas using anhydrous solvents. Also, except where otherwise noted, all reactions were run at room temperature (~23° C.).

When doing TLC (thin layer chromatography), $R_f$ is defined as the ratio of the distance traveled by the compound divided by the distance traveled by the eluent. $R_t$ (retention time).

Starting Materials

Generally, any of the following starting materials can be prepared using the procedures described in Schemes 7 or 8 of US Publication No. 2008/0132563, or alternatively, Schemes 2, 3 or 8 of US Publication No. 2007/0259821. More specifically, the following starting materials used in the following Examples can be prepared using the procedures described in the corresponding references or purchased from the corresponding vendor.

4-Bromo-2-(4-methoxy-benzyl)-1-methyl-benzene can be prepared by the procedures described in Example 8 of PCT Publication No. WO 01/027128.

4-Bromo-2-(4-ethoxy-benzyl)-1-methyl-benzene can be prepared by the procedures described in Preparation Example 17 of US2008/0132563.

4-Bromo-1-chloro-2-(4-methoxy-benzyl)-benzene can be prepared by the procedures described in Preparation Example 19 of US2008/0132563 or Example V of US2007/0259821.

4-Bromo-1-chloro-2-(4-ethoxy-benzyl)-benzene may be purchased from Shanghai Haoyuan Chemexpress Co., Ltd., Shanghai, People's Republic of China.

4-Bromo-2-(4-methoxy-benzyl)-benzonitrile can be prepared by the procedures described in Example XXII of US2007/0259821.

The following starting materials were prepared as described below.

Preparation of
4-bromo-1-fluoro-2-(4-methoxy-benzyl)-benzene

Oxalyl chloride (11.0 mL, 126 mmol) was added dropwise to a well stirred suspension of 5-bromo-2-fluoro-benzoic acid (25.0 g, 114 mmol) in dichloromethane (150 mL) and N,N-dimethylformamide (1.5 mL) at 0° C. The resulting mixture was allowed to gradually warm to room temperature. After 18 hours, the solid had gone into solution. The resulting light orange solution was concentrated under reduced pressure and was chased two times with diethyl ether to afford 5-bromo-2-fluoro-benzoyl chloride (27.0 g, quantitative yield) as a pale orange oil.

To a solution of 5-bromo-2-fluoro-benzoyl chloride (27.0 g, 114 mmol) and anisole (12.9 g, 13.0 mL, 119 mmol) in dichloromethane (150 mL) at 0° C. was added aluminum trichloride (16.2 g, 119 mmol) portionwise so that the internal temperature remained below 10° C. After stirring for 4 hours at 0° C., the solution was poured over crushed ice and the resulting mixture was stirred. After 30 minutes, the organic phase was removed and the aqueous phase was extracted two times with dichloromethane. The combined organic phases were washed once with aqueous 1M hydrochloric acid solution, once with aqueous 1M sodium hydroxide solution, and once with brine. The organic phase was dried over sodium sulfate, filtered, and concentrated under reduced pressure. The resulting residue was recrystallized from ethanol to afford (5-bromo-2-fluoro-phenyl)-(4-methoxy-phenyl)-methanone (22.5 g, 64%) as a white solid.

To a well stirred solution of (5-bromo-2-fluoro-phenyl)-(4-methoxy-phenyl)-methanone (22.5 g, 72.80 mmol) and triethylsilane (27.9 mL, 20.3 g, 175.0 mmol) in dichloromethane (20 mL) and acetonitrile (60 mL) at 0° C. was added boron trifluoride etherate (32.0 mL, 36.2 g, 255.0 mmol) dropwise. Boron trifluoride etherate was added at a rate so that the internal temperature did not exceed 20° C. The reaction solution was warmed to room temperature and stirred overnight. After a total of 18 hours, a solution of potassium hydroxide (5.0 g) in water (15.0 mL) was added and the resulting mixture was stirred for 2 hours. The organic phase was separated and the aqueous phase was extracted two times with diethyl ether. The combined organic phases were washed once with aqueous 1M sodium hydroxide solution and once with brine. The organic phase was dried over sodium sulfate, filtered, and concentrated under reduced pressure. Upon addition of ethanol to the resulting residue a white solid formed. The solid was collected and dried under high vacuum to afford 4-bromo-1-fluoro-2-(4-methoxy-benzyl)-benzene (20.1 g, 93% yield) as a white solid.

$^1H$ NMR (400 MHz, chloroform-d) delta ppm 3.79 (s, 3H), 3.89 (s, 2H), 6.85 (d, J=8.6 Hz, 2H), 6.91 (t, 1H), 7.12 (d, J=8.8 Hz, 2H), 7.21-7.31 (m, 2H).

Preparation of starting material
4-bromo-2-(4-ethoxy-benzyl)-benzonitrile

A solution of ethyl (4-ethoxy-phenyl)acetate (2.68 g, 12.87 mmol), 4-bromo-2-fluoro-benzonitrile (2.74 g, 13.70 mmol) in N-methylpyrrolidone (4 mL) was slowly added to a suspension of potassium tert-butoxide (3.14 g, 27.98 mmol) in N-methylpyrrolidone (13 mL) at 0° C. Upon addition, the solution became dark red. The dark-red mixture was stirred at 0° C. for 30 minutes and then at room temperature for 1 hour. Methanol (10 mL) and aqueous 1 M sodium hydroxide solution (13.7 mL) were added and the mixture was stirred overnight at room temperature. pH was adjusted to ~4 with hydrochloric acid (1 M aqueous solution) and the mixture was extracted with ethyl acetate (50 mL×4). The combined organic layers were washed with brine, dried over sodium sulfate and evaporated to dryness. N,N-dimethylformamide (5 mL) and potassium carbonate (7 g) were added, the mixture was heated to 100° C. for 1 hour and cooled to room temperature. Water was added and the mixture was extracted with ethyl acetate (60 mL×3). The combined organic layers were washed with brine, dried over sodium sulfate and evaporated to dryness. The crude was purified by flash chromatography over silica gel (eluting with a gradient of 0 to 14% ethyl acetate in heptane), to afford 2.26 g of crude product (containing the desired product and another product). The crude product was precipitated with methanol, affording 4-bromo-2-(4-ethoxy-benzyl)-benzonitrile (1.2 g, containing 5% of another compound with NMR peaks at 4.15 ppm quartet, and 1.5 ppm triplet).

$^1$H NMR (400 MHz, chloroform-d) delta 7.48-7.38 (m, 3H), 7.13 (d, J=8.4 Hz, 2H), 6.85 (d, J=8.4 Hz, 2H), 4.08 (s, 2H), 4.03 (q, J=7.2 Hz, 2H), 1.41 (t, J=7.2 Hz, 3H).

Preparation of starting material
4-bromo-2-(4-ethoxy-benzyl)-1-fluoro-benzene

To a solution of 4-bromo-1-fluoro-2-(4-methoxy-benzyl)-benzene (4.2 g, 14.2 mmol) in dichloromethane (20 mL) at 0° C. was slowly added a 1M solution of boron tribromide in dichloromethane (15.7 mL, 16.0 mmol) dropwise over 10 minutes. Once the addition of boron tribromide was complete the reaction mixture was gradually warmed to room temperature. After 4 hours, the reaction mixture was cooled to 0° C. and quenched by slow addition of 1 N aqueous hydrochloric acid solution (20 mL). The reaction mixture was stirred for 30 minutes and extracted twice with dichloromethane. The combined organic layers were dried over magnesium sulfate, filtered, and concentrated under reduced pressure to afford a light pink solid (3.83 g, 96%). The crude product 4-(5-bromo-2-fluoro-benzyl)-phenol was used in the next step without further purification.

$^1$H NMR (400 MHz, chloroform-d) delta ppm 3.88 (s, 2H), 4.76 (br. s., 1H), 6.77 (d, J=8.2 Hz, 2H), 6.91 (t, J=9.1 Hz, 1H), 7.07 (d, J=8.6 Hz, 2H), 7.23 (dd, J=6.8, 2.3 Hz, 1H), 7.26-7.31 (m, 1H).

To a solution of 4-(5-bromo-2-fluoro-benzyl)-phenol (6.0 g, 21.0 mmol) in anhydrous N,N-dimethylformamide (20 mL) cooled at 0° C. was added sodium hydride (60% dispersion in mineral oil, 1.02 g, 25.6 mmol). After stirring at 0° C. for 45 minutes, iodoethane (2.08 mL, 25.6 mmol) was added dropwise and the resulting mixture was allowed to warm up to room temperature. After 18 hours, the reaction mixture was quenched with water and extracted twice with ethyl acetate. The combined organic layers were washed twice with water and once with brine, dried over magnesium sulfate, filtered, and concentrated under reduced pressure. The crude residue was purified by flash chromatography over silica gel eluting with a gradient of 0 to 10% ethyl acetate in heptane to afford 4.6 g (58% yield) of the desired product as a yellow oil.

$^1$H NMR (400 MHz, chloroform-d) delta ppm 1.40 (t, J=7.0 Hz, 3H), 3.89 (s, 2H), 4.01 (q, J=6.9 Hz, 2H), 6.83 (d, J=8.4 Hz, 2H), 6.91 (t, J=9.0 Hz, 1H), 7.10 (d, J=8.8 Hz, 2H), 7.20-7.30 (m, 2H).

Preparation of toluene-4-sulfonic acid
tetrahydro-furan-3-yl ester

To a solution of 3-hydroxy tetrahydrofuran (2.5 g, 28.0 mmol) in anhydrous pyridine (60 mL) at room temperature was added 4-toluene sulfonyl chloride (6.49 g, 34.0 mmol). After stirring the reaction mixture for 18 hours at room temperature, the reaction mixture was concentrated under reduced pressure. The resulting residue was purified by flash chromatography over silica gel eluting with a gradient of 0 to 30% ethyl acetate in heptane to afford 3.5 g (51% yield) of the desired product as a colorless oil.

$^1$H NMR (400 MHz, chloroform-d) delta ppm 2.05-2.12 (m, 2H), 2.45 (s, 3H), 3.77-3.92 (m, 4H), 5.09-5.14 (m, 1H), 7.35 (d, J=8.00 Hz, 2H), 7.79 (d, 2H).

Preparation of toluene-4-sulfonic acid oxetan-3-yl
ester

To a solution of oxetan-3-ol (1.0 g, 13.0 mmol) in anhydrous pyridine (25 mL) at room temperature was added 4-toluene sulfonyl chloride (3.09 g, 16.2 mmol). After stirring the reaction mixture for 18 hours at room temperature, the reaction mixture was concentrated under reduced pressure. The resulting residue was purified by flash chromatography over silica gel eluting with a gradient of 0 to 30% ethyl acetate in heptane to afford 1.9 g (62% yield) of the desired product as a white solid.

$^1$H NMR (400 MHz, chloroform-d) delta ppm 2.46 (s, 3H), 4.63-4.75 (m, 4H), 5.26-5.34 (m, 1H), 7.36 (d, J=8.00 Hz, 2H), 7.78 (d, J=8.40 Hz, 2H).

Preparation of starting material 3-[4-(5-bromo-2-fluoro-benzyl)-phenoxy]-7-tetrahydro-furan To a solution of 4-(5-bromo-2-fluoro-benzyl)-phenol (1.5 g, 5.3 mmol) and cesium carbonate (2.61 g, 8.0 mmol) in N,N-dimethylformamide (15.0 mL) at room temperature was added a solution of toluene-4-sulfonic acid tetrahydro-furan-3-yl ester (1.94 g, 8.0 mmol) in N,N-dimethylformamide (10.0 mL). The reaction mixture was then stirred overnight at 50° C. After a total of 18 hours, the reaction mixture was cooled to room temperature, diluted with brine and extracted 3 times with ethyl acetate. The combined organic layers were washed twice with water and once with brine, dried over sodium sulfate, filtered, and concentrated under reduced pressure. The resulting crude residue was purified by flash chromatography over silica gel eluting with a gradient of 0 to 30% ethyl acetate in heptane to afford 1.66 g (89% yield) of the desired product as a colorless oil.

$^1$H NMR (400 MHz, chloroform-d) delta ppm 2.09-2.24 (m, 2H), 3.86-4.01 (m, 6H), 4.86-4.91 (m, 1H), 6.80 (d, J=8.6 Hz, 2H), 6.91 (t, J=9 Hz, 1H), 7.10 (d, J=8.6 Hz, 2H), 7.23 (dd, J=6.8, 2.5 Hz, 1H), 7.26-7.31 (m, 1H).

Preparation of starting material
3-[4-(5-bromo-2-fluoro-benzyl)-phenoxy]-oxetane To a solution of 4-(5-bromo-2-fluoro-benzyl)-phenol (1.1 g, 3.9 mmol) and cesium carbonate (1.91 g, 5.87 mmol) in N,N-dimethylformamide (15.0 mL) at room temperature was added a solution of toluene-4-sulfonic acid oxetan-3-yl ester (1.34 g, 8.0 mmol) in N,N-dimethylformamide (10.0 mL). The reaction mixture was then stirred overnight at 65° C. After a total of 18 hours, the reaction mixture was cooled to room temperature, diluted with brine and extracted 3 times with ethyl acetate. The combined organic layers were washed twice with water and once with brine, dried over sodium sulfate, filtered, and concentrated under reduced pressure. The crude residue was purified by flash chromatography over silica gel eluting with a gradient of 0 to 30% ethyl acetate in heptane to afford 0.948 g (72% yield) of the desired product as a white solid.

$^1$H NMR (400 MHz, chloroform-d) delta ppm 3.88 (s, 2H), 4.76 (dd, J=7.22, 5.3 Hz, 2H), 4.95 (t, J=6.6 Hz, 2H), 5.14-

5.21 (m, 1H), 6.63 (d, J=8.4 Hz, 2H), 6.92 (dd, 1H), 7.10 (d, J=8.6 Hz, 2H), 7.23 (dd, J=6.6, 2.15 Hz, 1H), 7.26-7.31 (m, 1H).

Preparation of 3-(4-(5-bromo-2-chlorobenzyl)phenoxy)oxetane 4-bromo-1-chloro-2-(4-methoxybenzyl)-benzene (10 g, 32 mmol) was dissolved in dichloromethane (32 mL) and cooled to 0° C. under nitrogen. A 1.0 M boron tribromide solution in dichloromethane (35.3 mL, 34.3 mmol) was added dropwise over 10 minutes. Following the addition, the ice bath was removed and the solution was stirred at room temperature for 1 hour. The reaction mixture was cooled to 0° C. and quenched by addition of 1N aqueous hydrochloric acid solution (45 mL). The mixture was stirred for 30 minutes, transferred to a separatory funnel, the organic layer was collected, and the aqueous layer was extracted with dichloromethane (45 mL). The combined organic extracts were dried over magnesium sulfate, filtered, and concentrated in vacuo to afford 4-(5-bromo-2-chlorobenzyl)phenol (9.5 g, 99% yield) as a white solid.

To a solution of crude 4-(5-bromo-2-chlorobenzyl)phenol (3.0 g, 10 mmol) and cesium carbonate (4.9 g, 15 mmol) in N,N-dimethylformamide (77.5 mL) at room temperature was added a solution of toluene-4-sulfonic acid oxetan-3-yl ester (3.5 g, 15 mmol) in N,N-dimethylformamide (8 mL). The mixture was heated to 65° C. for 22 hours whereupon an additional aliquot of cesium carbonate (3.3 g, 10 mmol) was added. The reaction mixture was stirred for a further 12 hours at 120° C., cooled to room temperature whereupon water and ethyl acetate were added and the mixture was carefully acidified with 1N aqueous hydrochloric acid solution. The organic layer was separated, washed with brine (3 times), and concentrated in vacuo. Purification via Biotage MPLC (silica gel, eluting with a gradient of 0 to 25% ethyl acetate in heptane) afforded 3-(4-(5-bromo-2-chlorobenzyl)phenoxy)oxetane (2.5 g, 70% yield) as a white solid.

$^1$H NMR (400 MHz, dichloromethane-d2) delta ppm 7.34-7.28 (m, 2H), 7.26 (d, J=8.4 Hz, 1H), 7.14-7.09 (m, 2H), 6.69-6.35 (m, 2H), 5.22-5.16 (m, 1H), 4.96-4.91 (m, 2H), 4.72-4.68 (m, 2H), 4.01 (s, 2H).

Preparation of 4-bromo-2-(4-chloro-benzyl)-1-fluoro-benzene

A solution of 5-bromo-2-fluorobenzaldehyde (10.2 g, 50 mmol) in anhydrous tetrahydrofuran (200 mL) was cooled to −78° C. A solution of 4-chlorophenyl-magnesium bromide (1M in diethyl ether, 60 mL, 60 mmol) was added via syringe over 8 minutes. Stirring was continued at low temperature for 5 minutes and the reaction was warmed up to room temperature and stirred for 1 hour at this temperature. The solution was cooled in an ice-water bath and quenched by addition of saturated aqueous ammonium chloride solution (40 mL). The organic phase was decanted and the aqueous residue was concentrated under reduced pressure to remove any remaining organic solvent. The aqueous phase was extracted with ethyl acetate (200 mL×2) and the extracts were combined with the decanted tetrahydrofuran solution. This solution was washed with brine (25 mL) and was dried (sodium sulfate), filtered and concentrated under reduced pressure, giving crude (5-bromo-2-fluorophenyl)-(4-chlorophenyl)-methanol (15.2 g, 96% yield) as a yellow solid.

To a solution of the above (5-bromo-2-fluorophenyl)-(4-chlorophenyl)-methanol (15.0 g, 48 mmol) and triethylsilane (18.5 mL, 116 mmol) in dichloromethane (40 mL) and acetonitrile (20 mL) at 0° C. under nitrogen, was slowly added boron trifluoride diethyl etherate (22.7 mL, 181 mmol). The resulting solution was stirred for 18 hours, while slowly warming to room temperature. The reaction was cooled in an ice-water bath, quenched by slow addition of 7 M aqueous potassium hydroxide solution (30 mL) and extracted with methyl tert-butyl ether (200 mL×2). The combined organic solution was washed with water (25 mL×2), brine (25 mL×2), dried (sodium sulfate), filtered and concentrated under reduced pressure. Purification by flash column chromatography over silica gel eluting with a gradient of ethyl acetate in heptane gave 2-(4-chlorobenzyl)-4-bromo-1-fluorobenzene (5.0 g, 35% yield) as a colorless oil. $^1$H NMR (400 MHz, chloroform-d) delta ppm 7.33-7.22 (m, 4H), 7.13 (d, J=8.4 Hz, 2H), 6.93 (dd, J=9.2, 9.2 Hz, 1H), 3.92 (s, 2H).

Preparation of Intermediates

Preparation of Intermediate ((2R,3R,4S,5R)-6-allyloxy-3,4,5-tris-benzyloxy-tetrahydro-pyran-2-yl)-methanol (I-1a)

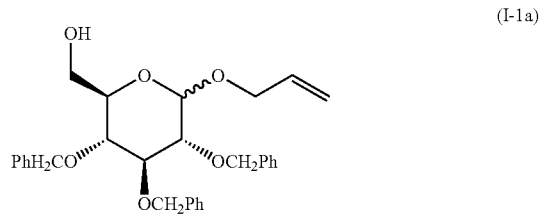

A suspension of D-glucose (1.2 kg, 6.6 mol), trifluoromethane sulfonic acid (12 mL) and allyl alcohol (5 L) was heated at 80° C. for 3 days. The mixture was cooled down to room temperature, the volatiles were removed in vacuo and the residue dissolved in N,N-dimethylformamide (8 L). This was split into four equal reactions and to each was added trityl chloride (463 g, 1.67 mol) and triethylamine (231 mL, 1.67 mol). A slight exotherm was observed while adding the triethylamine. The reaction mixture was stirred for 2 days at 30° C. and then each reaction split in half, giving eight equal reactions. To each of these reactions was added benzyl chloride (300 mL, 2.60 mol), followed by portionwise addition of sodium hydride (102.5 g, 2.60 mol) maintaining the reaction temperature between 40 to 50° C. After complete addition, the reaction mixtures were stirred at room temperature for 20 hours. Each reaction was then poured onto ice/water (2 L) and extracted with ethyl acetate (2.5 L). The organic phases of each were washed with saturated brine/water (1:1, 2×2 L), combined and dried over magnesium sulfate (product $R_f$ 0.85 in 3:1 hexanes/ethyl acetate). After filtration and evaporation the residue was dissolved in a mixture of dichloromethane (16 L) and methanol (4 L). The mixture was split into 5 equal portions and to each was added sulfuric acid (32 mL). The reactions were stirred for 3 hours, washed with brine/2M aqueous sodium hydroxide solution (1:1, 2×2 L), combined and dried over magnesium sulfate. After filtration and concentration in vacuo, the residue was further purified on silica gel eluting with 30% ethyl acetate in toluene to give intermediate compound (I-1a) as a mixture of anomers (1.77 kg, 54% yield from D-glucose). $R_f$ 0.15 in 3:1 hexanes/ethyl acetate.

Preparation of Intermediate ((3S,4S,5R)-6-allyloxy-3,4,5-tris-benzyloxy-2-hydroxymethyl-tetrahydro-pyran-2-yl)-methanol (I-1b)

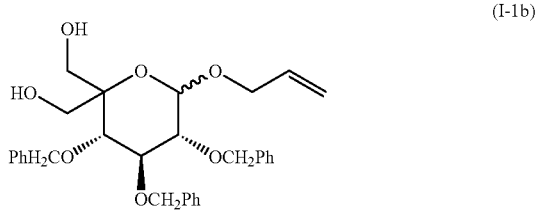

A solution of dimethylsulfoxide (87 mL, 1.22 mol) in dichloromethane (160 mL) was added dropwise to a solution of oxalyl chloride (64.7 mL, 0.76 mol) in dichloromethane (2.5 L) at −78° C. After complete addition a solution of intermediate (I-1a) (287 g, 0.59 mol) in dichloromethane (500 mL) was added dropwise at −78° C. After complete addition the reaction mixture was stirred for 30 minutes and triethylamine (417 mL, 2.9 mol) was added dropwise. After complete addition the reaction mixture was allowed to self warm to room temperature. The reaction was then washed with 1M aqueous hydrochloric acid solution (2 L) and water (2 L), and then dried over magnesium sulfate. This reaction procedure was repeated on six equivalent reactions and after drying they were combined and evaporated to give the aldehyde as a yellow oil (1.71 kg). This oil was dissolved in isopropanol (2.57 L) and split into seven equal reactions. To each of these was added a 37% aqueous formaldehyde solution (0.79 L, 10 mol), followed by the dropwise addition of a solution of sodium hydroxide (32 g, 0.8 mol) in water (130 mL). After complete addition the reaction mixture was stirred at room temperature for 2 days. The reaction mixture was diluted with brine (2 L) and extracted with ethyl acetate (2 L). The organic phase was further washed with saturated aqueous sodium bicarbonate solution (2 L), brine (2 L) and then dried over magnesium sulfate. The organic phases from the seven reactions were combined, evaporated and the residue purified on silica gel (eluting with 4 to 1 up to 1 to 1 hexanes in ethyl acetate) to give intermediate compound (I-1b) as a mixture of anomers (980 g, 53% yield over the two steps). $R_f$ 0.57 and 0.60 in 1:1 hexanes/ethyl acetate.

(3S,4S,5R)-6-allyloxy-3,4,5-tris-benzyloxy-2,2-bis-(4-methoxy-benzyloxymethyl)-tetrahydro-pyran (I-1c)

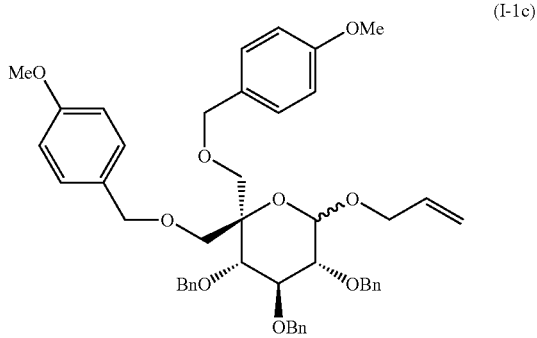

The starting diol [((3S,4S,5R)-6-allyloxy-3,4,5-tris-benzyloxy-2-hydroxymethyl-tetrahydro-pyran-2-yl)-methanol (I-1b: 10 g, 19.208 mmol) was dissolved in N,N-dimethylformamide (70 mL) and cooled to 0° C. Sodium hydride (60% dispersion in mineral oil, 1.69 g, 42.3 mmol) was added and the reaction was allowed to stir at 0° C. for 1 hour before the addition of 1-bromomethyl-4-methoxy-benzene (5.96 mL, 40.3 mmol). The reaction was then heated to 60° C. overnight. The mixture was cooled down to room temperature and the reaction was quenched with water and extracted with ethyl acetate (2 times). The combined organic layers were washed with water, brine, dried over sodium sulfate, filtered and concentrated under reduced pressure. The reaction was then chromatographed over silica gel (eluting with a gradient of 0 to 80% ethyl acetate in heptane) yielding 7.55 g (52% yield) of product (I-1c). MS 778.8 (M+NH$_4^+$; positive mode).

(3R,4S,5S)-3,4,5-tris-benzyloxy-6,6-bis-(4-methoxy-benzyloxymethyl)-tetrahydro-pyran-2-ol (I-1d)

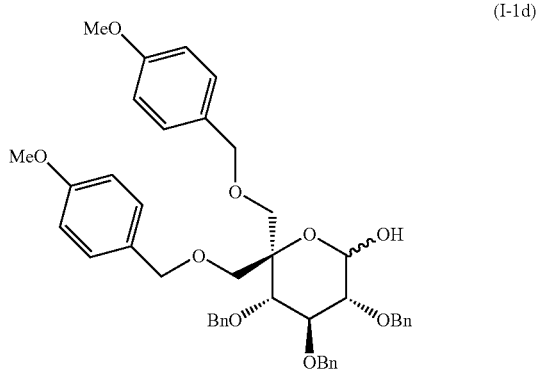

To a solution of starting material ((3S,4S,5R)-6-allyloxy-3,4,5-tris-benzyloxy-2,2-bis-(4-methoxy-benzyloxymethyl)-tetrahydro-pyran, (I-1c: 7.55 g, 9.92 mmol) in methanol (60 mL) and dichloromethane (20 mL) at room temperature was added in palladium (II) chloride (528 mg, 2.98 mmol) and the resulting mixture was stirred at this temperature for 4 hours. TLC indicated the clean formation of a more polar product. The reaction was filtered through Celite® and concentrated under reduced pressure. The crude material was chromatographed over silica gel eluting with a gradient of 0 to 80% ethyl acetate in heptane yielding 5.6 g (78% yield) of product (I-1d). MS 738.8 (M+NH$_4^+$; positive mode).

(3R,4S,5S)-3,4,5-tris-benzyloxy-6,6-bis-(4-methoxy-benzyloxymethyl)-tetrahydro-pyran-2-one (I-1e)

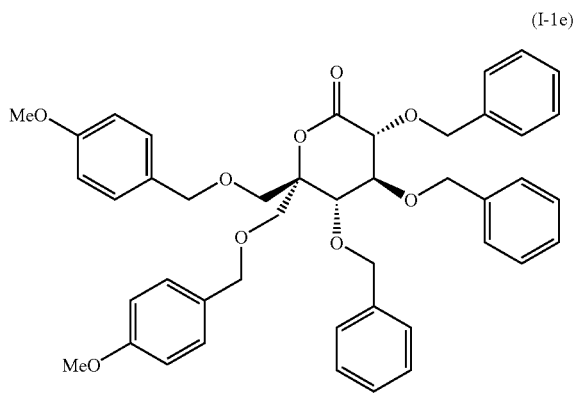

(I-1e)

(2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-g) and/or (3R,4S,5S)-3,4,5-tris-benzyloxy-6,6-bis-(4-methoxy-benzyloxymethyl)-2-(methoxy-methyl-amino)-tetrahydro-pyran-2-ol (I-1f)

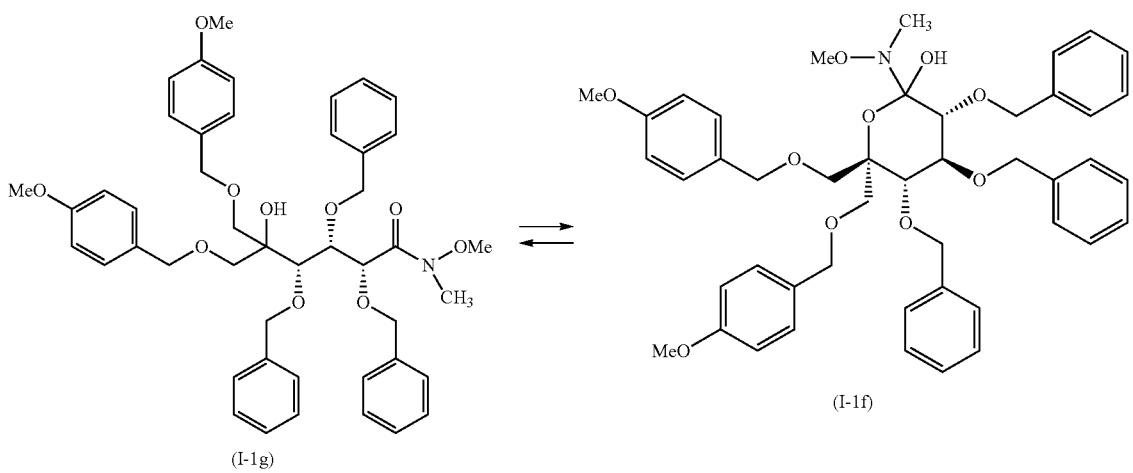

(I-1g)  (I-1f)

To a solution of oxalyl dichloride (1.9 mL, 23 mmol) in dichloromethane (65 mL) at −78° C. was added a solution of dimethyl sulfoxide (3.3 mL, 47 mmol) in dichloromethane (5 mL) and the resulting solution was stirred at this temperature for 30 minutes. A solution of starting material ((3R,4S,5S)-3,4,5-tris-benzyloxy-6,6-bis-(4-methoxy-benzyloxymethyl)-tetrahydro-pyran-2-ol, (I-1d, 5.6 g, 7.7 mmol) in dichloromethane (15.0 mL) was then added dropwise and the resulting mixture was stirred for 30 minutes allowing the temperature to rise to −60° C. Triethylamine (9.7 mL, 69.5 mmol) was added dropwise and the mixture allowed to warm up to 0° C. over 1 hour. The reaction was quenched by addition of saturated aqueous ammonium chloride solution and the organic phase was dried over magnesium sulfate, filtered and concentrated under reduced pressure. The crude material was purified by flash chromatography over silica gel eluting with a gradient of 0 to 60% ethyl acetate in heptane to produce the product (I-1e) (4 g, 72% yield).

$^1$H NMR (400 MHz, chloroform-d) delta ppm 3.24 (d, J=10 Hz, 1H), 3.40-3.47 (m, 2H), 3.74 (s, 3H), 3.77 (s, 3H), 3.86 (d, J=10 Hz, 1H), 4.07 (d, J=8.6 Hz, 1H), 4.15 (d, J=9.6 Hz, 1H), 4.35-4.55 (m, 6H), 4.65-4.72 (m, 2H), 4.82 (d, J=11 Hz, 1H), 4.87 (d, J=11.2 Hz, 1H), 5.10 (d, J=11.1 Hz, 1H), 6.74-6.79 (m, 2H), 6.81-6.85 (m, 2H), 7.11 (dd, J=7.0, 2.5 Hz, 2H), 7.17-7.41 (m, 17H).

To a solution of lactone ((3R,4S,5S)-3,4,5-tris-benzyloxy-6,6-bis-(4-methoxy-benzyloxymethyl)-tetrahydro-pyran-2-one (I-1e: 10.4 g, 14.5 mmol) and N,O-dimethyl-hydroxylamine hydrochloride (1.77 g, 29.0 mmol) in dichloromethane (100 mL) at 0° C. was added dropwise a 2.0 M solution of trimethyl aluminum in hexanes (14.5 mL, 29.0 mmol) and the resulting solution was stirred at room temperature for 16 hours. The reaction mixture was cooled to 0° C. and quenched by slow addition of aqueous 1N hydrochloric acid solution. The resulting mixture was allowed to stir for 1 hour. The organic phase was separated and washed with aqueous 1N hydrochloric acid solution, dried over sodium sulfate, filtered, and concentrated under reduced pressure. The crude material was purified by medium pressure chromatography (gradient of 5 to 40% ethyl acetate in heptane) yielding 6.5 g (58%) of product.

$^1$H NMR (400 MHz, chloroform-d) delta ppm 2.62 (br. s, 1H), 2.94 (br. s., 3H), 3.23 (br. s., 3H), 3.42 (d, J=9.4 Hz, 1H), 3.50-3.60 (m, 3H), 3.75 (s, 3H), 3.77 (s, 3H), 4.03 (d, J=6.9 Hz, 1H), 4.20 (dd, J=6.9, 3.3 Hz, 1H), 4.31-4.44 (m, 5H), 4.46-4.51 (m, 2H), 4.53 (d, J=12 Hz, 1H), 4.66 (d, J=12 Hz, 1H), 4.80 (br. d, J=11.5 Hz, 1H), 4.87 (d, J=11.4 Hz, 1H), 6.77-6.83 (m, 4H), 7.15-7.35 (m, 19H). ([M+H$^+$] 780.8, positive mode; [M+HCO$_2^-$] 824.7, negative mode). HRMS calculated for C$_{46}$H$_{54}$NO$_{10}$ (M+H$^+$) 780.3742, found 780.3708.

(2R,3S,4S)-2,3,4,6-tetrakis-benzyloxy-5-benzyloxymethyl-5-hydroxy-hexanoic acid methoxy-methyl-amide (I-6g) and/or (3R,4S,5S)-3,4,5-tris-benzyloxy-6,6-bis-benzyloxymethyl-2-(methoxy-methyl-amino)-tetrahydro-pyran-2-ol (I-6f)

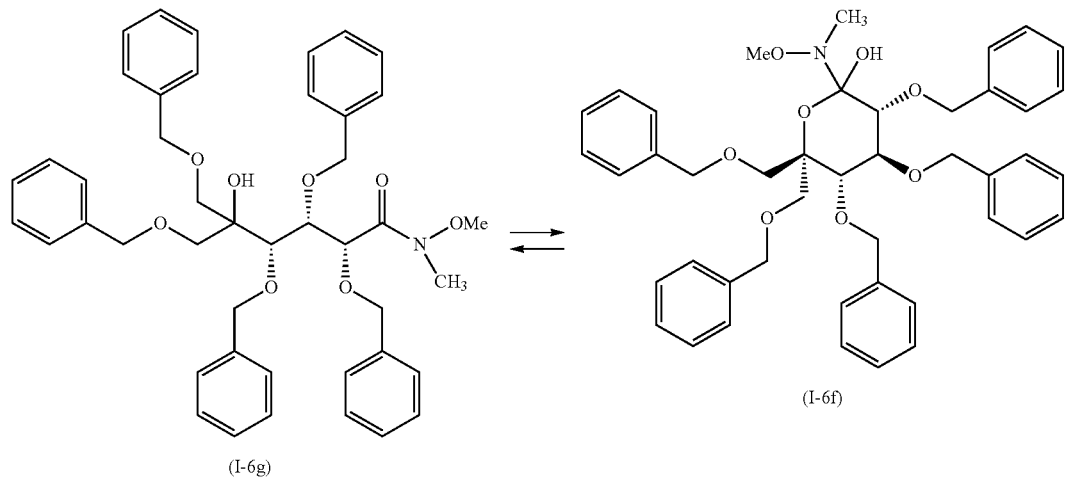

This compound was prepared starting from [((3S,4S,5R)-6-allyloxy-3,4,5-tris-benzyloxy-2-hydroxymethyl-tetrahydro-pyran-2-yl)-methanol (I-1b) using a similar procedure as the one described for the synthesis of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) and/or (3R,4S,5S)-3,4,5-tris-benzyloxy-6,6-bis-(4-methoxy-benzyloxymethyl)-2-(methoxy-methyl-amino)-tetrahydro-pyran-2-ol (I-1f) except that the alkylating agent used in the experimental part describing the conversion from (I-1b) to (I-1c) was benzyl bromide instead of para-methoxybenzyl bromide.

$^1$H NMR (400 MHz, chloroform-d) delta ppm 2.66 (br. s, 1H), 2.94 (br. s., 3H), 3.23 (br. s., 3H), 3.48 (d, J=9.4 Hz, 1H), 3.55-3.66 (m, 3H), 4.05 (d, J=6.9 Hz, 1H), 4.21 (dd, J=6.9, 3.3 Hz, 1H), 4.36 (d, 1H, J=11.7 Hz), 4.41-4.58 (m, 7H), 4.68 (d, J=11.9 Hz, 1H), 4.81 (br. d, J=11.5 Hz, 1H), 4.89 (d, J=11.5 Hz, 1H), 7.15-7.35 (m, 25H). MS [M+H$^+$] 720.7, positive mode; [M+HCO$_2^-$] 764.7, negative mode).

(4S,5S)-3,4,5-tris-benzyloxy-2-[3-(4-methoxy-benzyl)-4-methyl-phenyl]-6,6-bis-(4-methoxy-benzyloxymethyl)-tetrahydro-pyran-2-ol (I-1i)

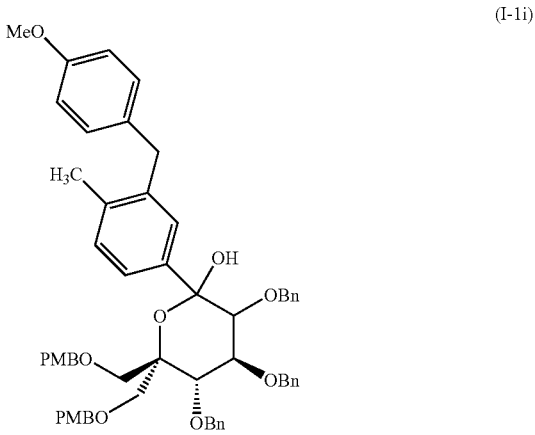

n-Butyl lithium (0.97 mL, 2.5 M/hexanes, 3.15 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-bromo-2-(4-methoxy-benzyl)-1-methyl-benzene (690 mg, 3 equivalents) in anhydrous tetrahydrofuran (2.7 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-g) (608 mg) in anhydrous tetrahydrofuran (1.35 mL) was then added dropwise over 1.5 hours using a syringe pump and the resulting mixture was stirred at −78° C. for 1 hour before being allowed to warm to −20° C. over 14 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of 1M aqueous hydrochloric acid solution. The resulting biphasic mixture was stirred at room temperature for 15 minutes. The organic phase was separated, washed with brine, dried over magnesium sulfate, filtered and concentrated. Chromatography over silica gel using a gradient of 20 to 50% ethyl acetate in heptane gave the product as a mixture of isomers (440 mg, 61% yield).

HRMS calculated for $C_{59}H_{62}O_{10}Na$ (M+Na$^+$) 953.4235, found 953.4236.

{(2S,3S)-2,3,4-tris-benzyloxy-5-[3-(4-methoxy-benzyl)-4-methyl-phenyl]-6,8-dioxa-bicyclo[3.2.1]oct-1-yl}-methanol (I-1k)

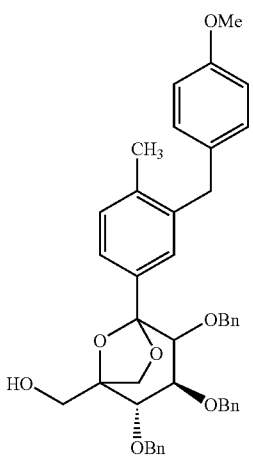

(I-1k)

To a solution of intermediate I-1i (150 mg) in dichloromethane (3 mL) was added anisole (90 microL, 5 equivalents) followed by 3 mL of a solution of 20% trifluoroacetic acid in dichloromethane and the resulting mixture was stirred at room temperature for about 1 hour. The mixture was concentrated and the crude was chromatographed over silica gel (using a gradient of 10 to 30% ethyl acetate in heptane) to afford the desired product as a mixture of isomers (66 mg, 61% yield). MS (LCMS) 673.9 (M+H$^+$; positive mode).

(4S,5S)-3,4,5-tris-benzyloxy-2-[3-(4-ethoxy-benzyl)-4-methyl-phenyl]-6,6-bis-(4-methoxy-benzyloxymethyl)-tetrahydro-pyran-2-ol (I-2i)

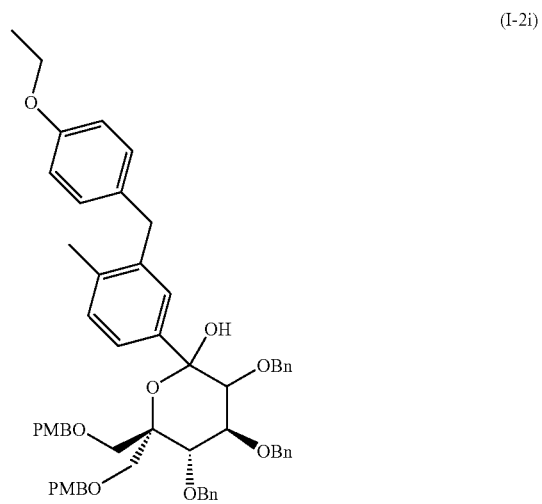

(I-2i)

n-Butyl lithium (0.312 mL, 2.5 M/hexanes, 3.05 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-bromo-2-(4-ethoxy-benzyl)-1-methyl-benzene (238 mg, 3.05 equivalents) in anhydrous tetrahydrofuran (0.9 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (200 mg) in anhydrous tetrahydrofuran (0.6 mL) was then added dropwise over 1.5 hours using a syringe pump and the resulting mixture was stirred at −78° C. for 1 hour before being allowed to warm to room temperature over 16 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of aqueous 1M hydrochloric acid solution. The resulting biphasic mixture was stirred at room temperature for 15 minutes. The organic phase was separated, washed with brine, dried over magnesium sulfate, filtered and concentrated. The crude material was chromatographed using the Biotage™ automated chromatography unit (two stacked 10 g silica gel columns; eluting with a gradient of 0 to 60% ethyl acetate in heptane) to give the product as a mixture of isomers (136 mg, 56% yield). MS (LCMS) 968 (M+Na$^+$; positive mode).

{(2S,3S)-2,3,4-tris-benzyloxy-5-[3-(4-ethoxy-benzyl)-4-methyl-phenyl]-6,8-dioxa-bicyclo[3.2.1]oct-1-yl}-methanol (I-2k)

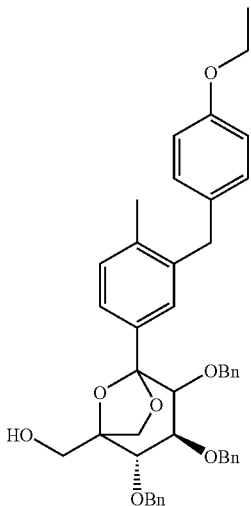

(I-2k)

To a solution of the intermediate I-2i (136 mg, 0.145 mmol) in dichloromethane (4 mL) was added anisole (310 microL, ~5 equivalents) followed by 4 mL of a solution of 20% trifluoroacetic acid in dichloromethane and the resulting mixture was stirred at room temperature for 1.5 hours. The mixture was concentrated and the crude was chromatographed using the ISCO™ Combiflash® Companion® automated chromatography unit (4 g silica gel column) and eluting with a gradient of 0 to 70% ethyl acetate in heptane to afford the desired product as a mixture of isomers (85 mg, 85% yield). MS (LCMS) 687.7 (M+H$^+$; positive mode).

(4S,5S)-3,4,5-tris-benzyloxy-2-[4-chloro-3-(4-methoxy-benzyl)-phenyl]-6,6-bis-(4-methoxy-benzyloxymethyl)-tetrahydro-pyran-2-ol (I-3i)

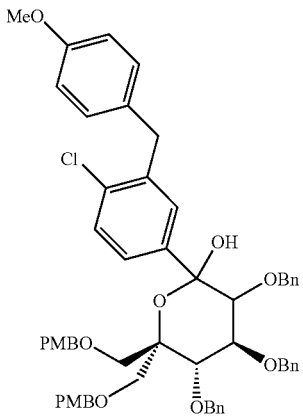

(I-3i)

n-Butyl lithium (0.97 mL, 2.5 M/hexanes, 3.15 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-bromo-1-chloro-2-(4-methoxy-benzyl)-benzene (725 mg, 2.95 equivalents) in anhydrous tetrahydrofuran (2.7 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (616 mg) in anhydrous tetrahydrofuran (1.35 mL) was then added dropwise over 1.5 hours using a syringe pump and the resulting mixture was stirred at −78° C. for 1 hour before being allowed to warm to −20° C. over 14 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of aqueous 1M hydrochloric acid solution. The resulting biphasic mixture was stirred at room temperature for 15 minutes. The organic phase was separated, washed with brine, dried over magnesium sulfate, filtered and concentrated. Chromatography over silica gel using a gradient of 10 to 40% ethyl acetate in heptane gave the product as a mixture of isomers (530 mg, 71% yield).

{(2S,3S)-2,3,4-tris-benzyloxy-5-[4-chloro-3-(4-methoxy-benzyl)-phenyl]-6,8-dioxa-bicyclo[3.2.1]oct-1-yl}-methanol (I-3k)

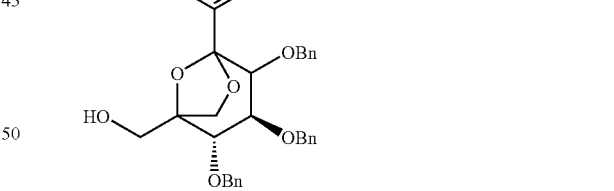

(I-3k)

To a solution of the intermediate I-3i (530 mg) in dichloromethane (11 mL) was added anisole (300 microL, 5 equivalents) followed by 11 mL of a solution of 20% trifluoroacetic acid in dichloromethane and the resulting mixture was stirred at room temperature for 1 hour. The mixture was concentrated and the crude was chromatographed over silica gel using a gradient of 10 to 40% ethyl acetate in heptane to afford the product as a mixture of isomers (229 mg, 59% yield)

MS (LCMS) 693.6 (M+H$^+$; positive mode). .

41

(4S,5S)-3,4,5-tris-benzyloxy-2-[4-chloro-3-(4-ethoxy-benzyl)-phenyl]-6,6-bis-(4-methoxy-benzyloxymethyl)-tetrahydro-pyran-2-ol (I-4i)

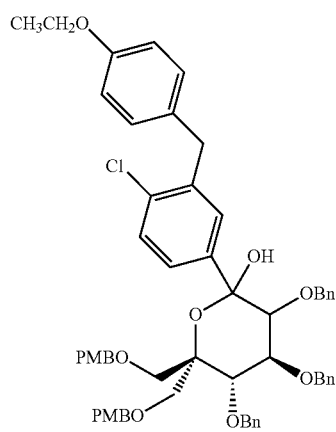

(I-4i)

n-Butyl lithium (1.0 mL, 2.5 M/hexanes, 3.25 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-bromo-1-chloro-2-(4-ethoxy-benzyl)-benzene (815 mg, 3.25 equivalents) in anhydrous tetrahydrofuran (2.9 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (600 mg) in anhydrous tetrahydrofuran (1.45 mL) was then added dropwise over 1.3 hours using a syringe pump and the resulting mixture was stirred at −78° C. for 1 hour before being allowed to warm to −25° C. over 14 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of aqueous 1M hydrochloric acid solution. The resulting biphasic mixture was stirred at room temperature for 15 minutes. The organic phase was separated, washed with brine, dried over magnesium sulfate, filtered and concentrated. Chromatography over silica gel using a gradient of 10 to 40% ethyl acetate in heptane gave the product as a mixture of isomers (280 mg, 38% yield).

HRMS calculated for $C_{59}H_{61}O_{10}ClNa$ (M+Na$^+$) 987.3845, found 987.3840.

42

{(2S,3S)-2,3,4-tris-benzyloxy-5-[4-chloro-3-(4-ethoxy-benzyl)-phenyl]-6,8-dioxa-bicyclo[3.2.1]oct-1-yl}-methanol (I-4k)

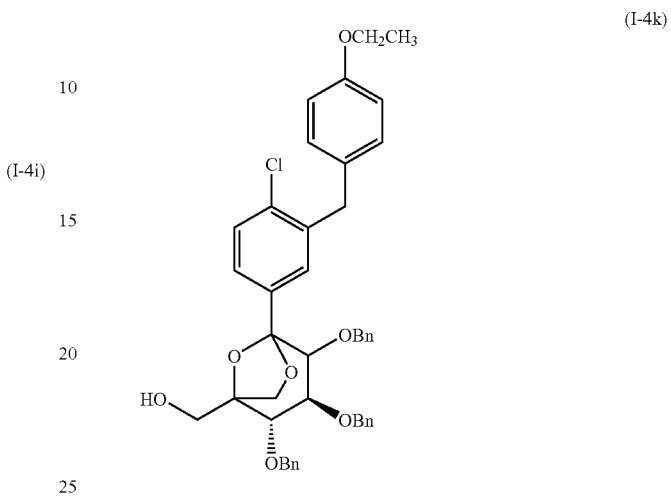

(I-4k)

To a solution of the intermediate I-4i (1.46 g) in dichloromethane (31 mL) was added anisole (900 microL, ~5 equivalents) followed by 31 mL of a solution of 20% trifluoroacetic acid in dichloromethane and the resulting mixture was stirred at room temperature for 1 hour. The mixture was concentrated and the crude was chromatographed over silica gel using a gradient of 10 to 30% ethyl acetate in heptane to afford the product as a mixture of isomers (670 mg, 63% yield).

HRMS calculated for $C_{43}H_{44}O_7Cl$ (M+H$^+$) 707.2770, found 707.2765.

(4S,5S)-3,4,5-tris-benzyloxy-2-[4-fluoro-3-(4-methoxy-benzyl)-phenyl]-6,6-bis-(4-methoxy-benzyloxymethyl)-tetrahydro-pyran-2-ol (I-5i)

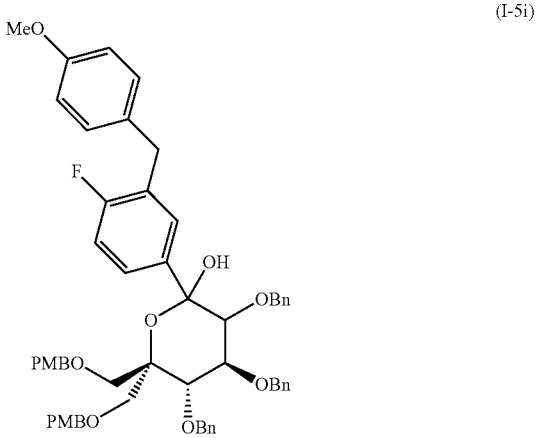

(I-5i)

n-Butyl lithium (462 microL, 2.5 M/hexanes, 3.0 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-Bromo-1-fluoro-2-(4-methoxy-benzyl)-benzene (341 mg, 3 equivalents) in anhydrous tetrahydrofuran (1.4 mL) at −78° C. under nitrogen. The resulting solution was stirred at this temperature for 1 hour. Then a solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (300 mg, 0.385 mmol) in anhydrous tetrahydrofuran (0.70 mL) was added dropwise very slowly (1 drop every 5 seconds) and the resulting mixture was stirred at −78° C. for an additional hour before warming to 10° C. over 12 hours (put in a deep Dewar covered with aluminum foil to maintain cold temperature; size of Dewar: external diameter 10 cm, internal diameter 8 cm, height 9 cm). The reaction was diluted with diethyl ether and quenched by the dropwise addition of aqueous 1N hydrochloric acid solution. The resulting biphasic mixture was stirred at room temperature for 15 minutes. The organic phase was separated, washed with brine, dried over magnesium sulfate, filtered, and concentrated under reduced pressure. The crude residue was purified by flash chromatography over silica gel (eluting with a gradient of 10 to 40% ethyl acetate in heptane) to afford the product as a mixture of isomers (199 mg, 55% yield).

{(2S,3S)-2,3,4-tris-benzyloxy-5-[4-fluoro-3-(4-methoxy-benzyl)-phenyl]-6,8-dioxa-bicyclo[3,2,1]oct-1-yl}-methanol (I-5k)

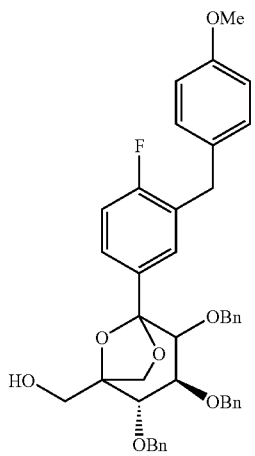

(I-5k)

To a solution of (4S,5S)-3,4,5-Tris-benzyloxy-2-[4-fluoro-3-(4-methoxy-benzyl)-phenyl]-6,6-bis-(4-methoxy-benzyloxymethyl)-tetrahydro-pyran-2-ol (I-5i; 191 mg, 0.204 mmol) in dichloromethane (3.75 mL) was added anisole (0.178 mL, 1.63 mmol) followed by a 20% solution of trifluoroacetic acid in dichloromethane (3.75 mL) at room temperature under nitrogen. After stirring for 1 hour at room temperature, the reaction mixture was concentrated under reduced pressure. The crude residue was purified by flash chromatography over silica gel (eluting with a gradient of 10 to 30% ethyl acetate in heptane) to afford the product as a mixture of isomers (115 mg, 83% yield). MS (LCMS) 677.7 (M+H$^+$; positive mode).

(4S,5S)-3,4,5-tris-benzyloxy-2-[3-(4-ethoxy-benzyl)-4-fluoro-phenyl]-6,6-bis-(4-methoxy-benzyloxymethyl)-tetrahydro-pyran-2-ol (I-10i)

(I-10i)

n-Butyl lithium (508 microL, 2.5 M/hexanes, 3.0 equivalents) was added dropwise (1 drop every 5 seconds) to an oxygen degassed solution of 4-Bromo-2-(4-ethoxy-benzyl)-1-fluoro-benzene (392.0 mg, 1.27 mmol) in anhydrous tetrahydrofuran (1.5 mL) at −78° C. under nitrogen. The resulting solution was stirred at this temperature for 1 hour. Then a solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide I-1g (330.0 mg, 0.423 mmol) in anhydrous tetrahydrofuran (0.75 mL) was added dropwise very slowly (1 drop every 5 seconds) and the resulting mixture was stirred at −78° C. for an additional hour before warming to 10° C. over 12 hours (put in a deep Dewar covered with aluminum foil to maintain cold temperature). The reaction was diluted with diethyl ether and quenched by the dropwise addition of aqueous 1N hydrochloric acid solution. The resulting biphasic mixture was stirred at room temperature for 15 minutes. The organic phase was separated, washed with brine, dried over magnesium sulfate, filtered, and concentrated under reduced pressure. The crude residue was purified by flash chromatography over silica gel (eluting with a gradient of 10 to 40% ethyl acetate in heptane) to afford the product as a mixture of isomers (180 mg, 44% yield).

{(2S,3S)-2,3,4-tris-benzyloxy-5-[3-(4-ethoxy-benzyl)-4-fluoro-phenyl]-6,8-dioxa-bicyclo[3.2.1]oct-1-yl}-methanol (I-10k)

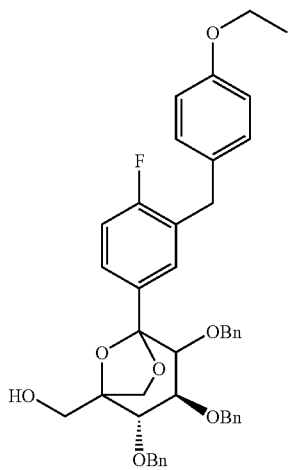

To a solution of intermediate I-10i (180.0 mg, 0.19 mmol) in dichloromethane (2.0 mL) was added anisole (0.175 mL, 1.60 mmol) followed by a 20% solution of trifluoroacetic acid in dichloromethane (2.0 mL) at room temperature under nitrogen. After stirring for 1 hour, the reaction mixture was concentrated under reduced pressure. The crude residue was purified by flash chromatography over silica gel (eluting with a gradient of 10 to 30% ethyl acetate in heptane) to afford the product as a mixture of isomers (85.0 mg, 64% yield).

(4S,5S)-3,4,5-tris-benzyloxy-2-{4-fluoro-3-[4-(tetrahydro-furan-3-yloxy)-benzyl]-phenyl}-6,6-bis-(4-methoxy-benzyloxymethyl)-tetrahydro-pyran-2-ol (I-11i)

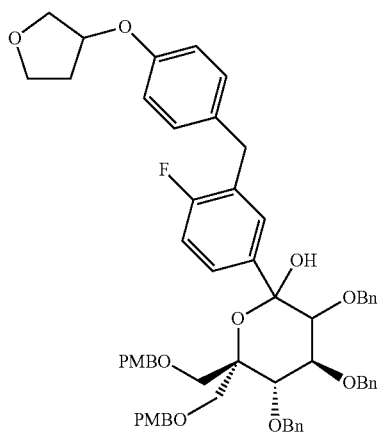

n-Butyl lithium (1.0 mL, 2.5 M/hexanes, 3.0 equivalents) was added dropwise (1 drop every 5 seconds) to an oxygen degassed solution of 3-[4-(5-bromo-2-fluoro-benzyl)-phenoxy]-tetrahydro-furan (878 mg, 2.50 mmol) in anhydrous tetrahydrofuran (3.0 mL) at −78° C. and the resulting solution was stirred at this temperature for 1 hour. A solution of (2R, 3S,4S)-2,3,4-tris-benzyloxy-5-hydroxy-6-(4-methoxy-benzyloxy)-5-(4-methoxy-benzyloxymethyl)-hexanoic acid methoxy-methyl-amide I-1g (650 mg, 0.833 mmol) in anhydrous tetrahydrofuran (1.5 mL) was then added dropwise very slowly (0.9 mL/hour) and the resulting mixture was stirred at −78° C. for an additional hour before warming to 10° C. over 12 hours (put in a deep Dewar covered with aluminum foil to maintain cold temperature). The reaction was diluted with diethyl ether and quenched by the dropwise addition of aqueous 1N hydrochloric acid solution. The resulting biphasic mixture was stirred at room temperature for 15 minutes. The organic phase was separated, washed with brine, dried over magnesium sulfate, filtered, and concentrated under reduced pressure. The crude residue was purified by flash chromatography over silica gel (eluting with a gradient of 10 to 40% ethyl acetate in heptane) to afford the product as a mixture of isomers (287 mg, 34% yield)

((2S,3S)-2,3,4-tris-benzyloxy-5-{4-fluoro-3-[4-(tetrahydro-furan-3-yloxy)-benzyl]-phenyl}-6,8-dioxa-bicyclo[3.2.1]oct-1-yl)-methanol (I-11k)

To a solution of (4S,5S)-3,4,5-Tris-benzyloxy-2-{4-fluoro-3-[4-(tetrahydro-furan-3-yloxy)-benzyl]-phenyl}-6,6-bis-(4-methoxy-benzyloxymethyl)-tetrahydro-pyran-2-ol I-11i (275 mg, 0.28 mmol) in dichloromethane (2.0 mL) was added anisole (0.250 mL, 2.29 mmol) followed by a 20% solution of trifluoroacetic acid in dichloromethane (8.0 mL) at room temperature under nitrogen. After stirring for 1 hour, the reaction mixture was concentrated under reduced pressure. The crude residue was purified by flash chromatography over silica gel (eluting with a gradient of 10 to 30% ethyl acetate in heptane) to afford the product as a mixture of isomers (168 mg, 83% yield).

(4S,5S)-3,4,5-tris-benzyloxy-2-[3-(4-chloro-benzyl)-4-fluoro-phenyl]-6,6-bis-(4-methoxy-benzyloxymethyl)-tetrahydro-pyran-2-ol (I-12i)

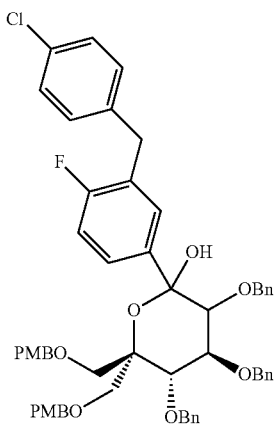

(I-12i)

n-Butyl lithium (1.0 mL, 2.5 M/hexanes, 3.1 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 4-Bromo-2-(4-chloro-benzyl)-1-fluoro-benzene (702 mg, 2.9 equivalents) in anhydrous tetrahydrofuran (3.0 mL) at −78° C. and the resulting solution was stirred at this temperature for 25 minutes. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (621 mg) in anhydrous tetrahydrofuran (1.5 mL) was then added dropwise using a syringe pump (0.9 mL/hour) and the resulting mixture was stirred at low temperature for an additional 17 hours (placed in a deep Dewar covered with aluminum foil to maintain cold temperature; size of Dewar: external diameter 10 cm, internal diameter 8 cm, height 9 cm). The reaction was quenched by dropwise addition of aqueous 1M hydrochloric acid solution (1.5 mL). The resulting biphasic mixture was stirred at room temperature for 30 minutes. The mixture was diluted with saturated aqueous ammonium chloride (15 mL) and was extracted with ethyl acetate (15 mL×3). The combined organic solution was washed with brine (30 mL), dried over magnesium sulfate, filtered and concentrated. Chromatography over silica gel using a gradient of 10 to 40% ethyl acetate in heptane gave the product as a mixture of isomers (477 mg, 64% yield).

{(2S,3S)-2,3,4-tris-benzyloxy-5-[3-(4-chloro-benzyl)-4-fluoro-phenyl]-6,8-dioxa-bicyclo[3.2.1]oct-1-yl}-methanol (I-12k)

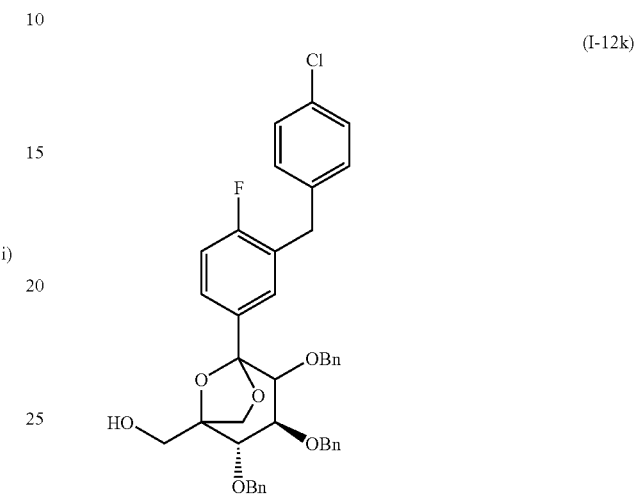

To a solution of the intermediate I-12i (243 mg) in dichloromethane (9 mL) was added anisole (0.15 mL, 5.3 equivalents) followed by trifluoroacetic acid (1.0 mL, 50 equivalents) and the resulting mixture was stirred at room temperature for 2 hours. The mixture was concentrated and the crude was chromatographed over silica gel using a gradient of 10 to 30% ethyl acetate in heptane to afford the product as a mixture of isomers (102 mg, 58% yield).

(4S,5S)-3,4,5-tris-benzyloxy-2-{4-fluoro-3-[4-(oxetan-3-yloxy)-benzyl]-phenyl}-6,6-bis-(4-methoxy-benzyloxymethyl)-tetrahydro-pyran-2-ol (I-13i)

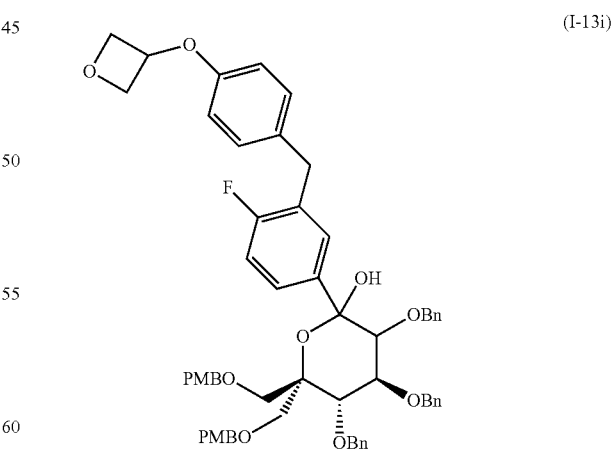

n-Butyl lithium (1.12 mL, 2.5 M/hexanes, 3.0 equivalents) was added dropwise (1 drop every 5 seconds) to an oxygen degassed solution of 3-[4-(5-Bromo-2-fluoro-benzyl)-phenoxy]-oxetane (942.0 mg, 2.79 mmol) in anhydrous tetrahydrofuran (3.0 mL) at −78° C. and the resulting solution was stirred at this temperature for 1 hour. A solution of (2R,3S, 4S)-2,3,4-tris-benzyloxy-5-hydroxy-6-(4-methoxy-benzyloxy)-5-(4-methoxy-benzyloxymethyl)-hexanoic acid methoxy-methyl-amide I-1g (725.0 mg, 0.930 mmol) in anhydrous tetrahydrofuran (1.5 mL) was then added dropwise very slowly (0.9 ml/hour) and the resulting mixture was stirred at −78° C. for an additional hour before warming to 10° C. over 12 hours (put in a deep Dewar covered with aluminum foil to maintain cold temperature). The reaction was diluted with diethyl ether and quenched by the dropwise addition of aqueous 1N hydrochloric acid solution. The resulting biphasic mixture was stirred at room temperature for 15 minutes. The organic phase was separated, washed with brine, dried over magnesium sulfate, filtered, and concentrated under reduced pressure. The crude residue was purified by flash chromatography over silica gel (eluting with a gradient of 10 to 40% ethyl acetate in heptane) to afford the product as a mixture of isomers (535 mg, 59% yield).

((2S,3S)-2,3,4-tris-benzyloxy-5-{4-fluoro-3-[4-(oxetan-3-yloxy)-benzyl]-phenyl}-6,8-dioxa-bicyclo[3.2.1]oct-1-yl)-methanol (I-13k)

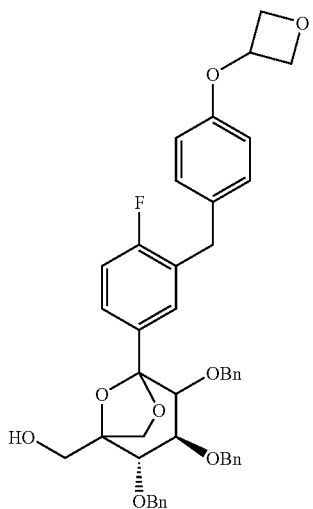

(I-13k)

To a solution of (4S,5S)-3,4,5-Tris-benzyloxy-2-{4-fluoro-3-[4-(oxetan-3-yloxy)-benzyl]-phenyl}-6,6-bis-(4-methoxy-benzyloxymethyl)-tetrahydro-pyran-2-ol I-13i (535 mg, 0.548 mmol) in dichloromethane (2.0 mL) was added anisole (0.480 mL, 4.38 mmol) followed by a 20% solution of trifluoroacetic acid in dichloromethane (8.0 mL) at room temperature under nitrogen. After stirring for 1 hour, the reaction mixture was concentrated under reduced pressure. The crude residue was purified by flash chromatography over silica gel (eluting with a gradient of 10 to 30% ethyl acetate in heptane) to afford the product as a mixture of isomers (300 mg, 76% yield).

(4S,5S)-3,4,5-tris-benzyloxy-2-{4-chloro-3-[4-(oxetan-3-yloxy)-benzyl]-phenyl}-6,6-bis-(4-methoxy-benzyloxymethyl)-tetrahydro-pyran-2-ol (I-14i)

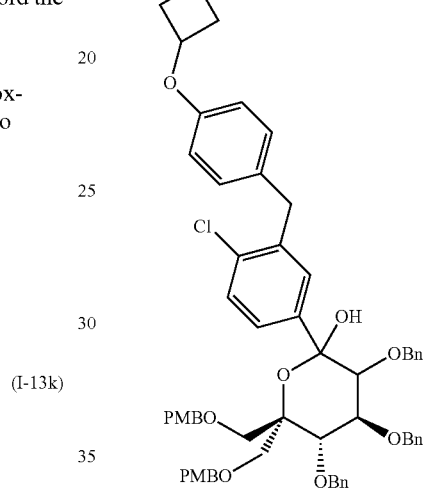

(I-14i)

n-Butyl lithium (0.97 mL, 2.5 M/hexanes, 3.15 equivalents) was added dropwise (1 drop every 5 seconds) to an oxygen degassed solution (placed in a pre dried Biotage™ microwave vial 10-20 mL sealed with its cap and placed under a positive stream of nitrogen gas) of 3-(4-(5-bromo-2-chlorobenzyl)phenoxy)oxetane (824 mg, 2.95 equivalents) in anhydrous tetrahydrofuran (2.7 mL) at −78° C. and the resulting solution was stirred at this temperature for an additional hour. A solution of (2R,3S,4S)-2,3,4-tris-benzyloxy-5-hydroxy-6-(4-methoxy-benzyloxy)-5-(4-methoxy-benzyloxymethyl)-hexanoic acid methoxy-methyl-amide (I-1g) (616 mg) in anhydrous tetrahydrofuran (1.35 mL) was then added dropwise over 1.5 hours using a syringe pump and the resulting mixture was stirred at −78° C. for 1 hour before being allowed to warm to −20° C. over 14 hours (put in a deep Dewar covered with aluminum foil to maintain cold temperature; size of Dewar: external diameter 10 cm, internal diameter 8 cm, height 9 cm). Diethyl ether was added and the reaction was quenched by dropwise addition of aqueous 1M hydrochloric acid solution. The resulting biphasic mixture was stirred at room temperature for 15 minutes. The organic phase was separated, dried over sodium sulfate, filtered and concentrated. Chromatography over silica gel using a gradient of 0-50% ethyl acetate in heptane gave the product as a mixture of isomers (563 mg, 72% yield).

((2S,3S)-2,3,4-Tris-benzyloxy-5-{4-chloro-3-[4-(oxetan-3-yloxy)-benzyl]-phenyl}-6,8-dioxa-bicyclo[3.2.1]oct-1-yl)-methanol (I-14k)

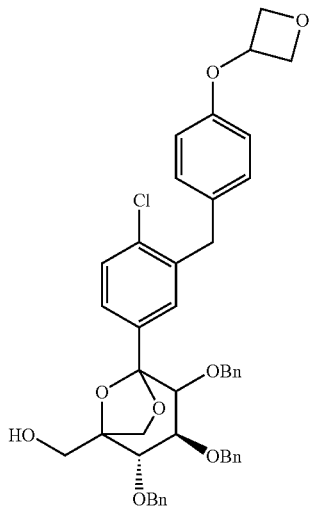

(I-14k)

To a solution of the intermediate (4S,5S)-3,4,5-tris-benzyloxy-2-{4-chloro-3-[4-(oxetan-3-yloxy)-benzyl]-phenyl}-6,6-bis-(4-methoxy-benzyloxymethyl)-tetrahydro-pyran-2-ol I-14i (282 mg) in dichloromethane (2.84 mL) was added anisole (200 microL, ~7 equivalents) followed by 3.07 mL of a solution of 20% trifluoroacetic acid in dichloromethane and the resulting mixture was stirred at room temperature for 1.5 hours. The mixture was concentrated and the crude was chromatographed over silica gel using a gradient of 10 to 50% ethyl acetate in heptane to afford the product as a mixture of isomers (186 mg, 89% yield).

Example 1

(1S,2S,3S,4R,5S)-1-hydroxymethyl-5-[3-(4-methoxy-benzyl)-4-methyl-phenyl]-6,8-dioxa-bicyclo[3.2.1]octane-2,3,4-triol (1A) and (1S,2S,3S,4S,5S)-1-hydroxymethyl-5-[3-(4-methoxy-benzyl)-4-methyl-phenyl]-6,8-dioxa-bicyclo[3.2.1]octane-2,3,4-triol (1B)

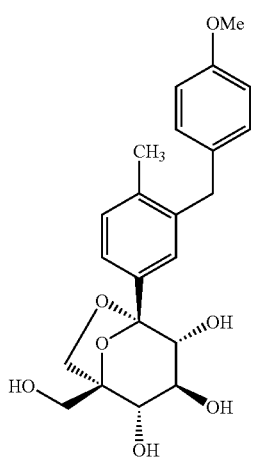

(1A)

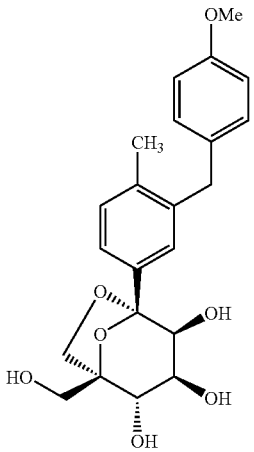

(1B)

To a solution of {(2S,3S)-2,3,4-tris-benzyloxy-5-[3-(4-methoxy-benzyl)-4-methyl-phenyl]-6,8-dioxa-bicyclo[3.2.1]oct-1-yl}-methanol (I-1k: 236 mg) in ethanol/tetrahydrofuran (7 mL, 4/1 volume) was added successively formic acid (270 microL, 19 equivalents) and palladium black (150 mg, 4 equivalents) and the resulting mixture was stirred at room temperature for 3 hours. The palladium was filtered and the crude mixture obtained after evaporation of solvent was purified by chromatography over silica gel eluting with a gradient of 85 to 100% ethyl acetate in heptane. The mixture of products obtained was purified by HPLC preparative.

HPLC preparative method: reverse phase C18 phenomenex column Luna 5 micrometer 150×21.20 mm, 20 mL/minute, gradient of acetonitrile/0.1% formic acid:water/0.1% formic acid; 20 to 60% of acetonitrile/0.1% formic acid over 20 minutes. UV detection: 254 nm. The HPLC indicated a ratio of diastereoisomers of 3:1 (1A:1B).

1A: (55 mg, 39% yield); $R_t$=10.9 minutes; the fractions containing the product were concentrated under reduced pressure. The crude material was precipitated from ethyl acetate and heptane. The resulting white solid was washed with heptane 2 times and dried under reduced pressure. MS (LCMS) 403.3 (M+H$^+$; positive mode) 447.3 (M+HCO$_2^-$, negative mode).

$^1$H NMR (400 MHz, methanol-d$_4$) delta 7.33 (d, 1H, J=1.6 Hz), 7.30 (dd, 1H, J=7.6 and 1.6 Hz), 7.10 (d, 1H, J=7.6 Hz), 7.02-6.98 (m, 2H), 6.79-6.75 (m, 2H), 4.13 (d, 1H, J=7.4 Hz), 3.90 (s, 2H), 3.82 (d, 1H, J=12.5 Hz), 3.77 (dd, 1H, J=8.2 and 1.2 Hz), 3.72 (s, 3H), 3.66 (d, 1H, J=12.5 Hz), 3.65 (t, 1H, J=8.0 Hz), 3.59 (d, 1H, J=7.8 Hz), 3.58 (dd, 1H, J=7.5 and 1.5 Hz), 2.16 (s, 3H). HRMS calculated for $C_{22}H_{27}O_7$ (M+H$^+$) 403.1751, found 403.1737.

1B: (20 mg, 14% yield); $R_t$=11.5 minutes; the fractions containing the product were concentrated under reduced pressure. The crude material was precipitated from ethyl acetate and heptane. The resulting white solid was washed with heptane 2 times and dried under reduced pressure. MS (LCMS) 403 (M+H$^+$; positive mode) 447 (M+HCO$_2^-$, negative mode).

$^1$H NMR (400 MHz, methanol-d$_4$) delta 7.38 (d, 1H, J=1.8 Hz) 7.33 (dd, 1H, J=7.9 and 1.8 Hz), 7.10 (d, 1H, J=7.9 Hz), 7.02-6.97 (m, 2H), 6.79-6.74 (m, 2H), 4.02 (d, 1H, J=7.4 Hz), 3.93 (t, 1H, J=2.2 Hz), 3.91 (br. s, 2H), 3.88 (d, 1H, J=12.5

Hz), 3.84 (d, 2H, J=2.4 Hz), 3.75 (d, 1H, J=12.5 Hz), 3.71 (s, 3H), 3.49 (d, 1H, J=7.4 Hz), 2.16 (s, 3H).

Example 2

(1S,2S,3S,4R,5S)-5-[3-(4-ethoxy-benzyl)-4-methyl-phenyl]-1-hydroxymethyl-6,8-dioxa-bicyclo[3.2.1]octane-2,3,4-triol (2A) and (1S,2S,3S,4S,5S)-5-[3-(4-ethoxy-benzyl)-4-methyl-phenyl]-1-hydroxymethyl-6,8-dioxa-bicyclo[3.2.1]octane-2,3,4-triol (2B)

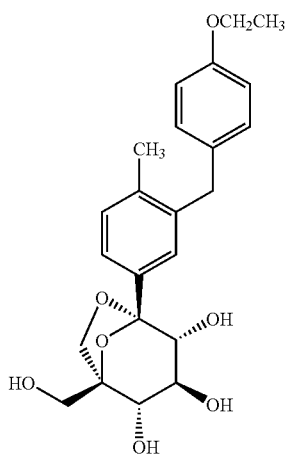
(2A)

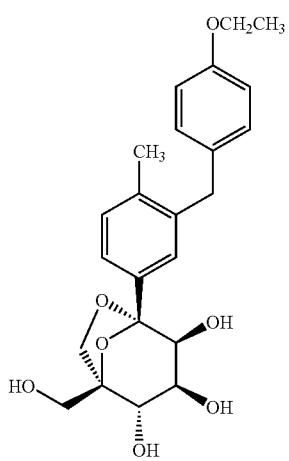
(2B)

To a solution of {(2S,3S)-2,3,4-tris-benzyloxy-5-[3-(4-ethoxy-benzyl)-4-methyl-phenyl]-6,8-dioxa-bicyclo[3.2.1]oct-1-yl}-methanol (I-2k: 85 mg, 0.12 mmol) in ethanol/tetrahydrofuran (7 mL, ~4/1 volume) was added successively formic acid (95 microL, 19 equivalents) and palladium black (53 mg, 4 equivalents) and the resulting mixture was stirred at room temperature for 3 hours. The palladium was filtered and the crude mixture obtained after evaporation of solvent was purified by HPLC preparative.

HPLC preparative method: reverse phase C18 phenomenex column Luna 5 micrometer 150×21.20 mm, 20 mL/minute, gradient of acetonitrile/0.1% formic acid:water/0.1% formic acid; 20 to 60% of acetonitrile/0.1% formic acid over 20 minutes. UV detection: 254 nm. The HPLC indicated a ratio of diastereoisomers of 4:1 (2A:2B).

2A: (20 mg; 38% yield) $R_f$=12.7 minutes; the fractions containing the product were concentrated under reduced pressure. The crude material was precipitated from ethyl acetate and heptane. The resulting white solid was washed with heptane 2 times and dried under reduced pressure.

MS (LCMS) 417.3 (M+H$^+$; positive mode); 461.4 (M+HCO$_2^-$; negative mode). $^1$H NMR (400 MHz, methanol-d$_4$) delta ppm 1.34 (t, J=6.9 Hz, 3H), 2.18 (s, 3H), 3.60 (d, J=8 Hz, 2H), 3.66 (t, J=8 Hz, 1H), 3.68 (d, J=12.5 Hz, 1H), 3.78 (d, 1H, J=8.8 Hz), 3.84 (d, J=12.4 Hz, 1H), 3.92 (s, 2H), 3.97 (q, J=7 Hz, 2H), 4.15 (d, J=7.5 Hz, 1H), 6.77 (m, 2H), 7.00 (m, 2H), 7.12 (d, J=7.7 Hz, 1H), 7.31 (dd, J=7.9 and 1.4 Hz, 1H), 7.34 (s, 1H).

2B: (5 mg; 9% yield) $R_f$=13.2; minutes the fractions containing the product were concentrated under reduced pressure. The crude material was precipitated from ethyl acetate and heptane. The resulting white solid was washed with heptane 2 times and dried under reduced pressure.

MS (LCMS) 417.3 (M+H$^+$; positive mode); 461.4 (M+HCO$_2^-$; negative mode). $^1$H NMR (400 MHz, methanol-d$_4$) delta ppm 1.34 (t, J=6.9 Hz, 3H), 2.18 (s, 3H), 3.52 (d, 1H, J=7.4 Hz), 3.77 (d, J=12.5 Hz, 1H), 4.00-3.84 (m, 8H), 4.04 (d, J=7.4 Hz, 1H), 6.79-6.75 (m, 2H), 7.03-6.98 (m, 2H), 7.12 (d, J=7.9 Hz, 1H), 7.35 (dd, J=7.7 and 1.9 Hz, 1H), 7.39 (d, J=1.9 Hz, 1H).

Example 3

(1S,2S,3S,4R,5S)-5-[4-chloro-3-(4-methoxy-benzyl)-phenyl]-1-hydroxymethyl-6,8-dioxa-bicyclo[3.2.1]octane-2,3,4-triol (3A) and (1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol (3B)

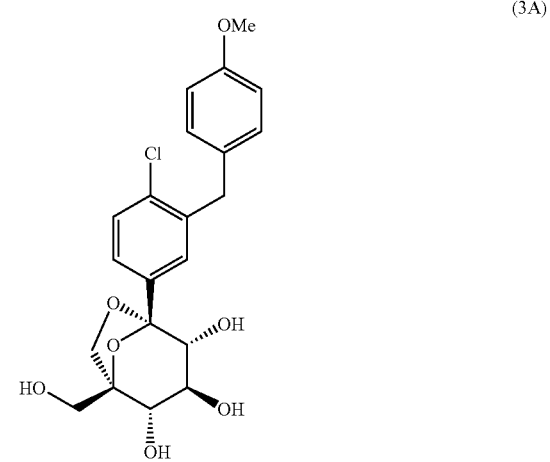
(3A)

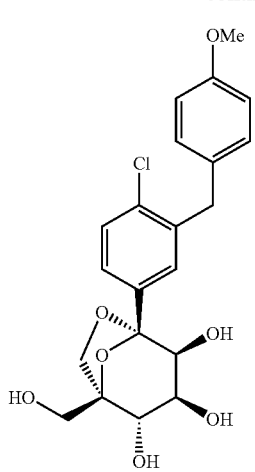

(3B)

To a solution of {(2S,3S)-2,3,4-tris-benzyloxy-5-[4-chloro-3-(4-methoxy-benzyl)-phenyl]-6,8-dioxa-bicyclo[3.2.1]oct-1-yl}-methanol (I-3k: 229 mg) in ethanol/tetrahydrofuran (7 mL, 4/1 volume) was added successively formic acid (270 microL, 20 equivalents) and palladium black (140 mg, 4 equivalents) and the resulting mixture was stirred at room temperature. After 1 hour, additional formic acid (270 microL, 20 equivalents) and palladium black (140 mg, 4 equivalents) were added and the mixture was allowed to stir for an additional hour at room temperature. The palladium was filtered and the crude mixture obtained after evaporation of solvent was purified by HPLC preparative.

HPLC preparative method: reverse phase C18 phenomenex column Luna 5 micrometer 150×21.20 mm, 20 mL/minutes, gradient of acetonitrile/0.1% formic acid:water/0.1% formic acid; 20 to 60% of acetonitrile/0.1% formic acid over 20 minutes. UV detection: 254 nm. The HPLC indicated a ratio of diastereoisomers of 1.4:1 (3A:3B).

3A: (50 mg; 36% yield) $R_f$=12.1 minutes; the fractions containing the product were concentrated under reduced pressure. The crude material was precipitated from ethyl acetate and heptane. The resulting white solid was washed with heptane 2 times and concentrated under reduced pressure.

MS (LCMS) 423.3 (M+H$^+$; positive mode); 467.3 (M+HCO$_2^-$; negative mode). $^1$H NMR (400 MHz, methanol-d$_4$) delta 7.43 (s, 1H), 7.38-7.30 (m, 2H), 7.08 (d, 2H), 6.79 (d, 2H), 4.12 (d, 1H, J=7.5 Hz), 4.01 (s, 2H), 3.81 (d, 1H, J=12.5 Hz), 3.75 (d, 1H, J=8.4 Hz), 3.73 (s, 3H), 3.66 (d, 1H, J=11.7 Hz), 3.63 (t, 1H, J=8.2 Hz), 3.57 (d, 1H, J=7.4 Hz), 3.52 (d, 1H, J=7.8 Hz). HRMS calculated for C$_{21}$H$_{24}$O$_7$Cl (M+H$^+$) 423.1205, found 423.1192.

3B: (37 mg; 27% yield) $R_f$=12.8 minutes; the fractions containing the product were concentrated under reduced pressure. The crude material was precipitated from ethyl acetate and heptane. The resulting white solid was washed with heptane 2 times and concentrated under reduced pressure.

MS (LCMS) 423.3 (M+H$^+$; positive mode) 467.3 (M+HCO$_2^-$, negative mode). $^1$H NMR (400 MHz, methanol-d$_4$) delta 7.50 (d, 1H, J=1.9 Hz) 7.42 (dd, 1H, J=8.3 and 1.9 Hz), 7.35 (d, 1H, J=8.3 Hz), 7.12-7.07 (m, 2H), 6.83-6.78 (m, 2H), 4.06-4.01 (m, 3H), 3.91-3.83 (m, 4H), 3.78-3.72 (m, 4H), 3.51 (d, 1H, J=7.5 Hz).

Example 4

(1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (4A) and (1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol (4B)

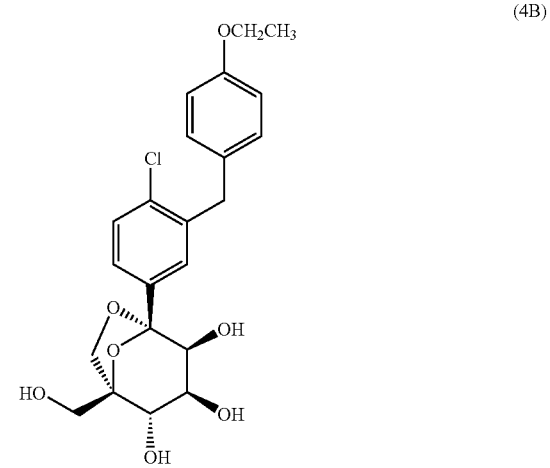

(4A)

(4B)

To a solution of {(2S,3S)-2,3,4-tris-benzyloxy-5-[4-chloro-3-(4-ethoxy-benzyl)-phenyl]-6,8-dioxa-bicyclo[3.2.1]oct-1-yl}-methanol (I-4-k: 335 mg) in ethanol/tetrahydrofuran (10 mL, 4/1 volume) was added successively formic acid (420 microL, 22 equivalents) and palladium black (208 mg, 4 equivalents) and the resulting mixture was stirred at room temperature. After 1 hour, additional formic acid (420 microL, 22 equivalents) and palladium black (208 mg, 4 equivalents) were added and the mixture was allowed to stir for an additional hour at room temperature. The palladium was filtered and the crude mixture obtained after evaporation of solvent was purified by HPLC preparative.

HPLC preparative: reverse phase C18 Gemini column 5 micrometer 30×100 mm, 40 mL/minute, gradient of acetonitrile/0.1% formic acid:water/0.1% formic acid; 25 to 50% of acetonitrile/0.1% formic acid over 18 minutes; UV detection: 220 nm. The HPLC indicated a ratio of diastereomers of 1.1:1 (4A:4B).

4A: (60 mg, 29% yield); $R_t$=12.4 minutes; the fractions containing the product were concentrated under reduced pressure. The crude material was precipitated from ethyl acetate and heptane. The resulting white solid was washed with heptane 2 times and dried under reduced pressure.

MS (LCMS) 437.3 (M+H$^+$; positive mode); 481.3 (M+HCO$_2^-$; negative mode). $^1$H NMR (400 MHz, methanol-$d_4$) delta 7.43 (d, 1H, J=1.9 Hz), 7.36 (dd, 1H, J=8.3 and 2 Hz), 7.32 (d, 1H, J=8.3 Hz), 7.08-7.04 (m, 2H), 6.79-6.75 (m, 2H), 4.12 (d, 1H, J=7.5 Hz), 4.00 (s, 2H), 3.96 (q, 2H, J=7.0 Hz), 3.81 (d, 1H, J=12.5 Hz), 3.75 (dd, 1H, J=8.3 and 1.3 Hz), 3.65 (d, 1H, J=12.5 Hz), 3.63 (t, 1H, J=8.2 Hz), 3.57 (dd, 1H, J=7.5 and 1.3 Hz), 3.52 (d, 1H, J=8.0 Hz), 1.33 (t, 3H, J=6.9 Hz). HRMS calculated for C$_{22}$H$_{26}$O$_7$Cl (M+H$^+$) 437.1361, found 437.1360.

4B: (30 mg, 15% yield); $R_t$=13.2 minutes; the fractions containing the product were concentrated under reduced pressure. The crude material was precipitated from ethyl acetate and heptane. The resulting white solid was washed with heptane 2 times and dried under reduced pressure.

MS (LCMS) 437.3 (M+H$^+$; positive mode) 481.3 (M+HCO$_2^-$, negative mode). $^1$H NMR (400 MHz, methanol-$d_4$) delta 7.48 (d, 1H, J=1.9 Hz) 7.40 (dd, 1H, J=8.1 and 1.9 Hz), 7.32 (d, 1H, J=8.3 Hz), 7.08-7.03 (m, 2H), 6.80-6.74 (m, 2H), 4.04-3.99 (m, 3H), 3.95 (q, 2H, J=7 Hz), 3.89-3.81 (m, 4H), 3.73 (d, 1H, J=12.5 Hz), 3.49 (d, 1H, J=7.3 Hz), 1.32 (t, 3H, J=7 Hz). HRMS calculated for C$_{22}$H$_{26}$O$_7$Cl (M+H$^+$) 437.1361, found 437.1358.

Example 5

(1S,2S,3S,4R,5S)-5-[4-fluoro-3-(4-methoxy-benzyl)-phenyl]-1-hydroxymethyl-6,8-dioxa-bicyclo[3.2.1]octane-2,3,4-triol (5A) and (1S,2S,3S,4S,5S)-5-[4-fluoro-3-(4-methoxy-benzyl)-phenyl]-1-hydroxymethyl-6,8-dioxa-bicyclo[3.2.1]octane-2,3,4-triol (5B)

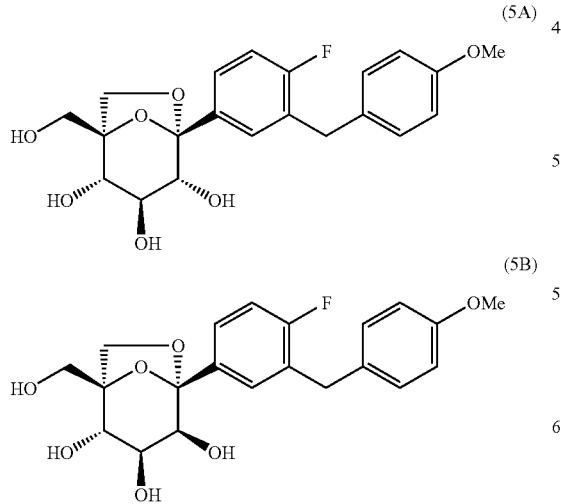

To a solution of {(2S,3S)-2,3,4-Tris-benzyloxy-5-[4-fluoro-3-(4-methoxy-benzyl)-phenyl]-6,8-dioxa-bicyclo[3.2.1]oct-1-yl}-methanol (115 mg, 0.170 mmol) in a 4:1 solution of ethanol/tetrahydrofuran (10 mL) was added successively formic acid (137 microL, 3.42 mmol) and palladium black (73 mg, 0.687 mmol). The resulting mixture was stirred at room temperature. After 3 hours, additional formic acid (137 microL, 3.42 mmol) and palladium black (73 mg, 0.687 mmol) were added. After 18 hours, the reaction mixture was filtered and the filtrate was concentrated under reduced pressure. The resulting crude residue was purified by flash chromatography over silica gel (eluting with a gradient of 0 to 15% methanol in dichloromethane) to afford 64 mg of a white solid. The mixture of isomers was purified by preparative HPLC.

HPLC preparative method: reverse phase C18 phenomenex column Luna 5 micrometer 150×21.20 mm, 20 mL/minute, gradient of acetonitrile/0.1% formic acid:water/0.1% formic acid; 20 to 80% of acetonitrile/0.1% formic acid over 20 minutes). UV detection: 254 nm. The HPLC indicated a ratio of diastereomers of 1:1 (5A:5B).

5A: (6 mg; 9% yield) $R_t$=8.5 minutes; the fractions containing the product were concentrated under reduced pressure. The crude material was precipitated from ethyl acetate and heptane. The resulting white solid was washed with heptane 2 times and dried under reduced pressure.

$^1$H NMR (400 MHz, methanol-$d_4$) delta ppm 3.55 (d, J=7.8 Hz, 1H), 3.58 (dd, J=7.5, 1.2 Hz, 1H), 3.64 (t, J=8.2 Hz, 1H), 3.67 (d, J=12.5 Hz, 1H), 3.74 (s, 3H), 3.77 (dd, J=8.3, 1.2 Hz, 1H), 3.83 (d, J=12.5 Hz, 1H), 3.91 (s, 2H), 4.14 (d, J=7.4 Hz, 1H), 6.76-6.84 (m, 2H), 7.02 (dd, J=9.9, 8.3 Hz, 1H), 7.09-7.13 (m, 2H), 7.37-7.44 (m, 2H); MS: 407.4 (M+H$^+$; positive mode); 451.3 (M+HCO$_2^-$; negative mode)

5B: (12 mg, 17% yield) $R_t$=9 minutes; the fractions containing the product were concentrated under reduced pressure. The crude material was precipitated from ethyl acetate and heptane. The resulting white solid was washed with heptane 2 times and dried under reduced pressure.

$^1$H NMR (400 MHz, methanol-$d_4$) delta ppm 3.51 (d, J=7.4 Hz, 1H), 3.74 (s, 3H), 3.75 (d, 1H, J=13 Hz), 3.83-3.93 (m, 6H), 4.03 (d, J=7.4 Hz, 1H), 6.78-6.82 (m, 2H), 7.02 (dd, J=9.9, 8.5 Hz, 1H), 7.09-7.13 (m, 2H), 7.42-7.49 (m, 2H); MS: 407.4 (M+H$^+$; positive mode); 451.3 (M+HCO$_2^-$; negative mode)

Example 6

2-(4-methoxybenzyl)-4-((1S,2S,3S,4R,5S)-2,3,4-trihydroxy-1-(hydroxymethyl)-6,8-dioxa-bicyclo[3,2,1]oct-5-yl)-benzonitrile (6A)

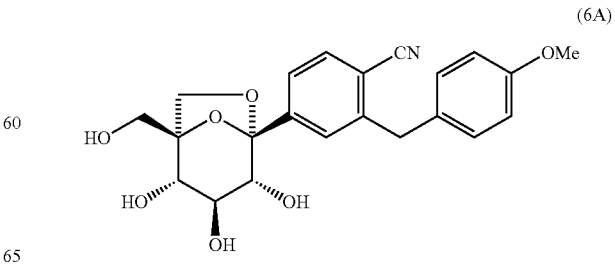

n-Butyl lithium (1.04 mL, 2.6 mmol, 2.5 M in hexane) was added to a solution of isopropyl magnesium bromide (1.27 mL, 1.27 mmol, 1 M in tetrahydrofuran) at 0° C. After being stirred for 30 minutes, the resulting mixture was cooled to −78° C. and a solution of 4-bromo-2-(4-ethoxy-benzyl)-benzonitrile (380 mg, 1.20 mmol) in anhydrous tetrahydrofuran (1 mL) was added. The greenish mixture was stirred for 1 hour at −78° C. and a solution of (2R,3S,4S)-2,3,4,6-tetrakis-benzyloxy-5-benzyloxymethyl-5-hydroxy-hexanoic acid methoxy-methyl-amide (I-6g) (700 mg, 0.972 mmol) in anhydrous tetrahydrofuran (2 mL) was added very slowly (over 20 minutes, 1 drop every 5 seconds). The solution was stirred at −78° C. for 1 hour and slowly warmed up to room temperature over 3 hours. The reaction was quenched by dropwise addition of aqueous 1M hydrochloric acid solution and then diluted with ethyl acetate. The resulting biphasic mixture was stirred at room temperature for 15 minutes. The organic phase was separated, washed with brine, dried over magnesium sulfate, filtered and concentrated, affording the crude product. The crude product was purified by flash chromatography over silica gel eluting with a gradient of 0 to 20% ethyl acetate in heptane affording the desired intermediate 2-(4-Ethoxy-benzyl)-4-((4S,5S)-3,4,5-tris-benzyloxy-6,6-bis-benzyloxymethyl-2-hydroxy-tetrahydro-pyran-2-yl)-benzonitrile (300 mg; 34% yield). MS 918.8 (M+Na$^+$, positive mode).

Boron trichloride (4.18 mL, 4.18 mmol, 1 M solution in hexane) was added to the solution of the above intermediate (250 mg, 0.279 mmol) in CH$_2$Cl$_2$ (2 mL) at −78° C. The mixture was stirred at −78° C. for 10 minutes and then warmed up to room temperature overnight. The mixture was quenched with water (10 mL) and extracted with ethyl acetate (50 mL). The organic layer was dried over sodium sulfate and evaporated to dryness. Purification by flash chromatography over silica gel (eluting with methanol in dichloromethane: 1 to 9 in volume) gave the desired intermediate 2-(4-Hydroxy-benzyl)-4-((1S,2S,3S,4R,5S)-2,3,4-trihydroxy-1-hydroxymethyl-6,8-dioxa-bicyclo[3.2.1]oct-5-yl)-benzonitrile (35 mg, 30% yield).

Potassium carbonate (28 mg, 0.2 mmol) was added to a solution of the above intermediate (34 mg, 0.077 mmol) in acetone (0.4 mL), followed by iodomethane (7 microL, 0.11 mmol) at room temperature. The mixture was stirred at 45° C. overnight. The mixture was diluted with ethyl acetate (60 mL) and washed with water. The organic layer was dried over sodium sulfate and evaporated to dryness. Purification by preparative Thin Layer Chromatography over silica gel (eluting with methanol in dichloromethane: 1 to 9 in volume) allowed isolation of desired product 6A (18 mg; 57% yield).

$^1$H NMR (400 MHz, methanol-d$_4$) delta 7.69 (d, J=8 Hz, 1H), 7.61 (s, 1H), 7.56 (d, J=8 Hz, 1H), 7.19-7.14 (m, 2H), 6.87-6.82 (m, 2H), 4.18 (d, J=7.6 Hz, 1H), 4.14 (s, 2H), 3.86 (d, J=12.7 Hz, 1H); 3.81 (d, J=8.3 Hz, 1H), 3.76 (s, 3H), 3.69 (d, J=12.5 Hz, 1H); 3.67 (t, J=8.1 Hz, 1H), 3.61 (d, J=7.6 Hz, 1H), 3.54 (d, J=8 Hz, 1H); MS 458.4 (M+HCO$_2^-$; negative mode).

Example 7

2-(4-ethoxybenzyl)-4-((1S,2S,3S,4R,5S)-2,3,4-trihydroxy-1-(hydroxymethyl)-6,8-dioxa-bicyclo[3,2,1]oct-5-yl)-benzonitrile (7A)

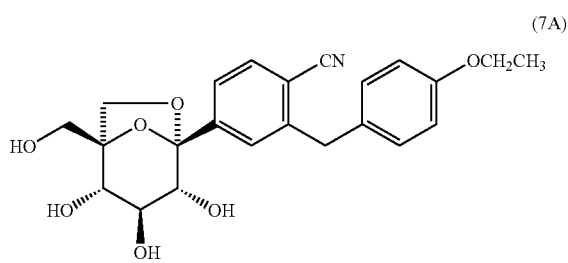

(7A)

Potassium carbonate (8 mg, 0.058 mmol) was added to a solution of intermediate 2-(4-hydroxy-benzyl)-4-((1S,2S,3S,4R,5S)-2,3,4-trihydroxy-1-hydroxymethyl-6,8-dioxa-bicyclo[3.2.1]oct-5-yl)-benzonitrile (see example 6; 8.9 mg, 0.022 mmol) in acetone (0.4 mL), followed by iodoethane (4 microL, 0.044 mmol) at room temperature. The mixture was stirred at 45° C. overnight. The mixture was diluted with ethyl acetate (60 mL) and washed with water. The organic layer was dried over sodium sulfate and evaporated to dryness. Purification by preparative Thin Layer Chromatography over silica gel (eluting with methanol in dichloromethane: 1 to 9 in volume) allowed isolation of desired product 7A (2.4 mg; 26% yield).

$^1$H NMR (methanol-d$_4$) delta 7.69 (d, J=8.0 Hz, 1H), 7.61 (d, J=1.5 Hz, 1H), 7.56 (dd, J=8.0, 1.5 Hz, 1H), 7.17-7.13 (m, 2H), 6.86-6.81 (m, 2H), 4.18 (d, J=7.5 Hz, 1H), 4.14 (s, 2H), 4.01 (q, J=7.0 Hz, 2H); 3.86 (d, J=12.5 Hz, 1H); 3.80 (dd, J=8.0 and 1.2 Hz, 1H), 3.70 (d, J=11.7 Hz, 1H), 3.67 (t, J=8.0 Hz, 1H), 3.61 (dd, J=7.5 and 1.2 Hz, 1H), 3.54 (d, J=7.8 Hz, 1H), 1.37 (t, J=7.0 Hz, 3H); MS 472.1 (M+HCO$_2^-$; negative mode).

Example 8 illustrates the preparation of a crystalline derivative of the compound of Example 3B in order to confirm the structure and stereochemistry of Example 3B.

Example 8

Per 4-bromobenzoylation of (1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol (3B) to give (8A)

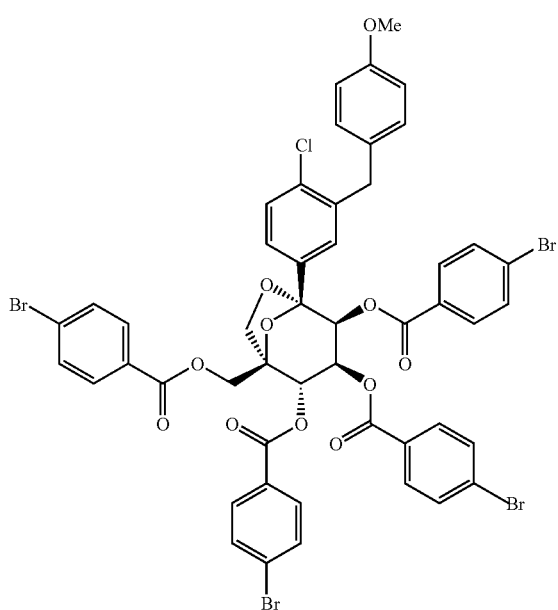

(8A)

To a solution of (1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol (3B) (11 mg, 0.026 mmol) in anhydrous tetrahydrofuran (600 microL) were added at room temperature N,N-diisopropylethylamine (32 microL, 7 equivalents) and 4-dimethylaminopyridine (3 mg, 0.9 equivalents) followed by para-bromobenzoyl chloride (35 mg, 6 equivalents) and the resulting mixture was stirred at room temperature for 62 hours. Ethyl acetate and water were added and the organic phase was successively washed with 0.5M aqueous hydrochloric acid solution and brine. The organic phase was dried over magnesium sulfate, filtered, concentrated and the crude was purified by flash chromatography over silica gel eluting with a gradient of 15 to 30% ethyl acetate in heptane to afford 27 mg of product (90% yield).

$^1$H NMR (400 MHz, chloroform-d) delta 7.82 (m, 2H), 7.74-7.64 (m, 4H), 7.58-7.46 (m, 8H), 7.42-7.34 (m, 4H), 7.29 (d, 1H, J=8.3 Hz), 6.89 (m, 2H), 6.63 (m, 2H), 6.04 (dd, 1H, J=9.6 and 1 Hz), 5.98 (dd, 1H, J=9.6 and 4.4 Hz), 5.89 (d, 1H, J=4.4 Hz), 4.70 (d, 1H, J=12.4 Hz), 4.65 (d, 1H, J=12.4 Hz), 4.60 (d, 1H, J=8 Hz), 3.98-3.88 (m, 3H), 3.73 (s, 3H).

Single crystals were obtained by vapor diffusion techniques using heptane and ethyl acetate as solvents. Melting point=191° C. *Single Crystal X-Ray Analysis.* A representative crystal was surveyed and a 1 Å data set (maximum sin Θ/λ=0.5) was collected on a Bruker APEX II/R diffractometer. Friedel pairs were collected in order to facilitate the determination of the absolute configuration. Atomic scattering factors were taken from the International Tables for Crystallography. See, *International Tables for Crystallography*, Vol. C, pp. 219, 500, Kluwer Academic Publishers, 1992. All crystallographic calculations were facilitated by the SHELXTL system. See, *SHELXTL*, Version 5.1, Bruker AXS, (1997). All diffractometer data were collected at room temperature. Pertinent crystal, data collection, and refinement are summarized in Table 1 below.

TABLE 1

Crystal data and structure refinement for Example 8A.

| | |
|---|---|
| Empirical formula | $C_{49}H_{35}O_{11}Br_4Cl$ |
| Formula weight | 1154.86 |
| Temperature | 296(2) K |
| Wavelength | 1.54178 Å |
| Crystal system | Monoclinic |
| Space group | C2 |
| Unit cell dimensions | a = 23.7485(6) Å   α = 90°. |
| | b = 6.3175(2) Å   β = 104.4910(10)°. |
| | c = 32.3167(8) Å   γ = 90°. |
| Volume | 4694.3(2) Å$^3$ |
| Z | 4 |
| Density (calculated) | 1.634 Mg/m$^3$ |
| Absorption coefficient | 5.216 mm$^{-1}$ |
| F(000) | 2296 |
| Crystal size | 0.12 × 0.03 × 0.02 mm$^3$ |
| Theta range for data collection | 3.75 to 50.43°. |
| Reflections collected | 8339 |
| Independent reflections | 3932 [R(int) = 0.0491] |
| Completeness to theta = 50.43° | 89.7% |
| Absorption correction | Empirical Absorption Correction |
| Refinement method | Full-matrix least-squares on F$^2$ |
| Data/restraints/parameters | 3932/1/587 |
| Goodness-of-fit on F$^2$ | 0.967 |
| Final R indices [I > 2sigma(I)] | R1 = 0.0371, wR2 = 0.0854 |
| Absolute structure parameter | −0.03(2) |
| Extinction coefficient | 0.00011(3) |
| Largest diff. peak and hole | 0.297 and −0.294 e · Å$^{-3}$ |

A trial structure was obtained by direct methods. This trial structure refined routinely. Hydrogen positions were calculated wherever possible. The methyl hydrogens were located by difference Fourier techniques and then idealized. The hydrogen parameters were added to the structure factor calculations but were not refined. The shifts calculated in the final cycles of least squares refinement were all less than 0.1 of the corresponding standard deviations. The final R-index was 3.71%. A final difference Fourier revealed no missing or misplaced electron density. The refined structure was plotted using the SHELXTL plotting package (FIG. 1). The absolute configuration was determined by the method of Flack. See, Flack, H. D., *Acta Crystalloar.*, A39, 876, (1983).

Example 9 illustrates the preparation of a crystalline derivative of the compound of Example 4A in order to confirm the structure and stereochemistry of Example 4A.

Example 9

Per 4-nitrobenzoylation of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (4A) to give (9A)

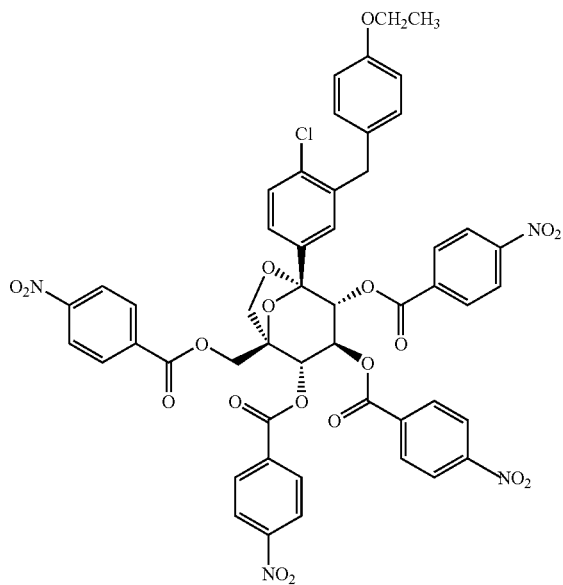

(9A)

To a solution of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (4A: 10.6 mg, 0.024 mmol) in anhydrous tetrahydrofuran (300 microL) cooled at 0° C. were added N,N-diisopropylethylamine (30 microL, 7 equivalents) and 4-dimethylaminopyridine (3 mg, 1 equivalents) followed by para-nitrobenzoyl chloride (27 mg, 6 equivalents) and the resulting mixture was stirred at 60° C. for 6 hours. The mixture was cooled to room temperature, ethyl acetate and water were added and the organic phase was successively washed with 0.5M aqueous hydrochloric acid solution and brine. The organic phase was dried over magnesium sulfate, filtered, concentrated and the crude was purified by flash chromatography over silica gel eluting with a gradient of 10 to 50% ethyl acetate in heptane to afford 18 mg of product (73% yield).

$^1$H NMR (400 MHz, chloroform-d) delta 8.33 (m, 2H), 8.28-8.12 (m, 8H), 8.07 (m, 2H), 8.00 (m, 2H), 7.91 (m, 2H), 7.45-7.40 (m, 2H), 7.34 (d, 1H, J=8.2 Hz), 6.87 (m, 2H), 6.64 (m, 2H), 6.13 (d, 1H, J=8.6 Hz), 6.06 (t, 1H, J=8.3 Hz), 5.86 (d, 1H, J=8.1 Hz), 4.81 (d, 1H, J=8.3 Hz), 4.75 (d, 1H, J=12.7 Hz), 4.60 (d, 1H, J=12.8 Hz), 4.06 (d, 1H, J=8.5 Hz), 3.98-3.90 (m, 4H), 1.39 (t, 3H, J=7 Hz).

Single crystals were obtained by slow recrystallization from acetonitrile/isopropanol as solvents. Melting point=211° C. A representative crystal was surveyed and a 0.88 Å data set (maximum sin $\Theta/\lambda=0.57$) was collected on a Bruker APEX II/R diffractometer. Friedel pairs were collected in order to facilitate the determination of the absolute configuration. Atomic scattering factors were taken from the International Tables for Crystallography. See, *International Tables for Crystallography*, Vol. C, pp. 219, 500, Kluwer Academic Publishers, 1992. All crystallographic calculations were facilitated by the SHELXTL system. See, *SHELXTL*, Version 5.1, Bruker AXS, (1997). All diffractometer data were collected at room temperature. Pertinent crystal, data collection, and refinement are summarized in Table 2 below.

TABLE 2

| Crystal data and structure refinement for Example 9A. | |
|---|---|
| Empirical formula | $C_{50}H_{37}N_4O_{19}Cl$ |
| Formula weight | 1033.29 |
| Temperature | 296(2) K |
| Wavelength | 1.54178 Å |
| Crystal system | Monoclinic |
| Space group | P2(1) |
| Unit cell dimensions | a = 17.5050(4) Å  α = 90°. |
|  | b = 6.2303(2) Å  β = 97.6580(10)°. |
|  | c = 21.9545(5) Å  γ = 90°. |
| Volume | 2373.03(11) Å$^3$ |
| Z | 2 |
| Density (calculated) | 1.446 Mg/m$^3$ |
| Absorption coefficient | 1.452 mm$^{-1}$ |
| F(000) | 1068 |
| Crystal size | 0.18 × 0.02 × 0.01 mm$^3$ |
| Theta range for data collection | 2.55 to 61.76°. |
| Reflections collected | 8972 |
| Independent reflections | 5062 [R(int) = 0.0236] |
| Completeness to theta = 61.76° | 85.8% |
| Absorption correction | Empirical Absorption Correction |
| Max. and min. transmission | 0.9856 and 0.7801 |
| Refinement method | Full-matrix least-squares on F$^2$ |
| Data/restraints/parameters | 5062/1/668 |
| Goodness-of-fit on F$^2$ | 1.009 |
| Final R indices [I > 2sigma(I)] | R1 = 0.0436, wR2 = 0.1090 |
| Absolute structure parameter | 0.02(3) |
| Extinction coefficient | 0.0015(2) |
| Largest diff. peak and hole | 0.217 and −0.173 e · Å$^{-3}$ |

A trial structure was obtained by direct methods. This trial structure refined routinely. Hydrogen positions were calculated wherever possible. The methyl hydrogens were located by difference Fourier techniques and then idealized. The hydrogen parameters were added to the structure factor calculations but were not refined. The shifts calculated in the final cycles of least squares refinement were all less than 0.1 of the corresponding standard deviations. The final R-index was 4.36%. A final difference Fourier revealed no missing or misplaced electron density.

Figure 2:
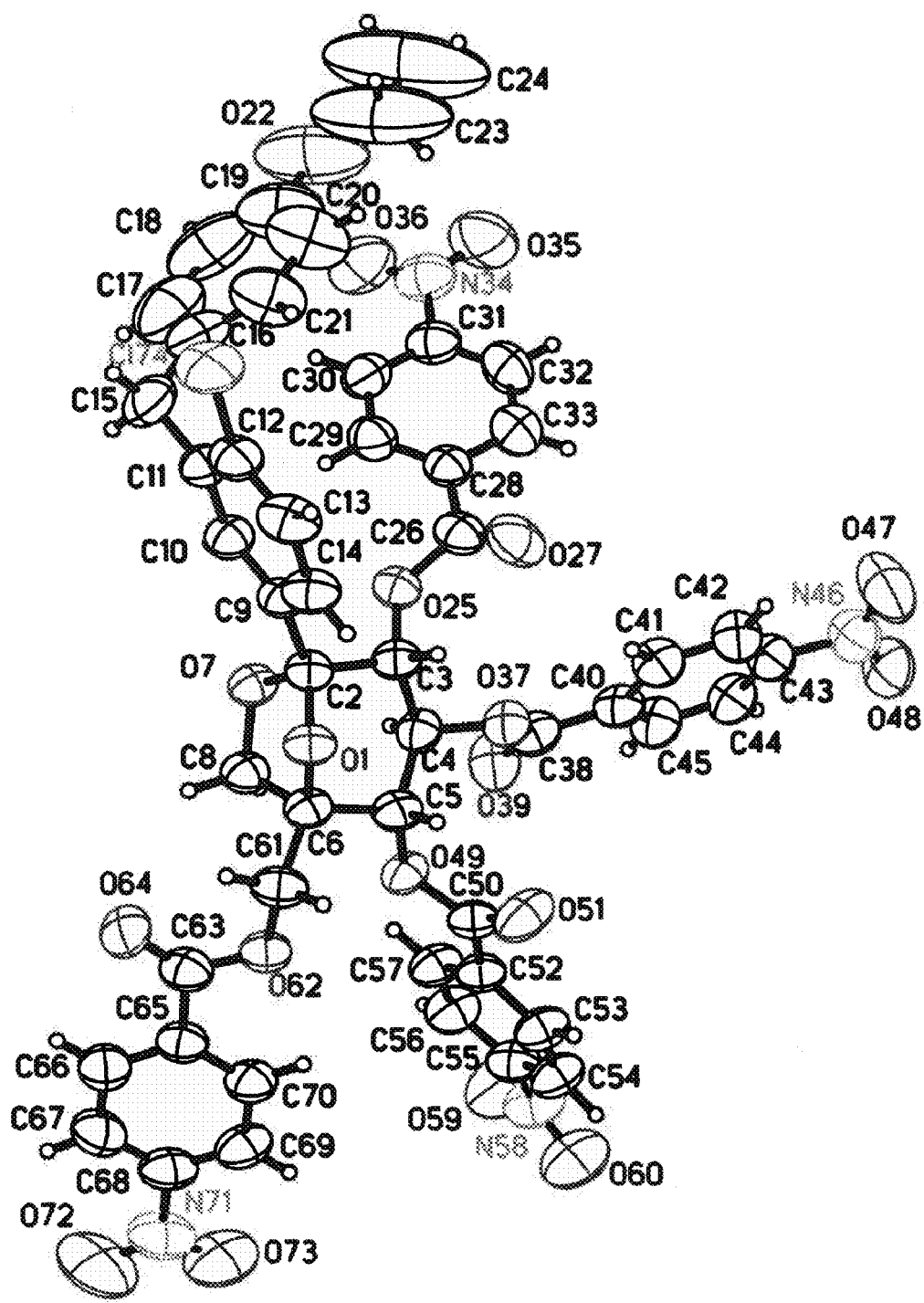
FIG. 2 represents the refined crystal structure for the Example 9A compound which was plotted using the SHELXTL plotting package.

The refined structure was plotted using the SHELXTL plotting package (FIG. 2). The absolute configuration was determined by the method of Flack See, Flack, H. D., Acta Crystalloar., A39, 876, (1983).

Example 10

(1S,2S,3S,4R,5S)-5-[3-(4-ethoxy-benzyl-4-fluoro-phenyl]-1-hydroxymethyl-6,8-dioxa-bicyclo[3.2.1]octane-2,3,4-triol (10A) and (1S,2S,3S,4S,5S)-5-[3-(4-ethoxy-benzyl)-4-fluoro-phenyl]-1-hydroxymethyl-6,8-dioxa-bicyclo[3.2.1]octane-2,3,4-triol (10B)

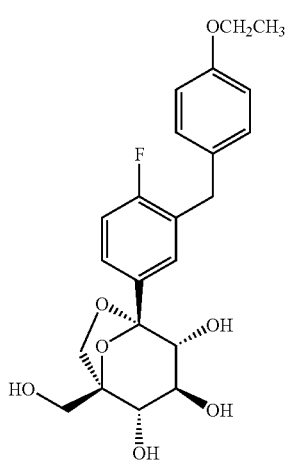

(10A)

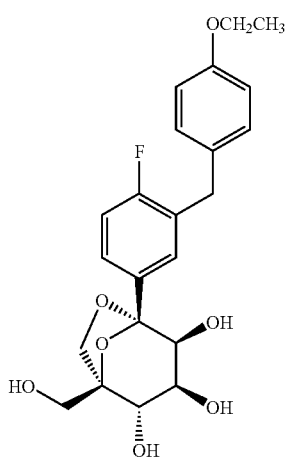

(10B)

To a solution of {(2S,3S)-2,3,4-tris-benzyloxy-5-[3-(4-ethoxy-benzyl)-4-fluoro-phenyl]-6,8-dioxa-bicyclo[3.2.1]oct-1-yl}-methanol I-10k (80.0 mg, 0.120 mmol) in a 4:1 solution of ethanol/tetrahydrofuran (10 mL) was added successively formic acid (93 microL, 2.32 mmol) and palladium black (62 mg, 0.580 mmol). The resulting mixture was stirred at room temperature. After 3 hours, additional formic acid (93 microL, 2.32 mmol) and palladium black (62 mg, 0.580 mmol) were added. After 5 hours, the reaction mixture was filtered and the filtrate was concentrated under reduced pressure. The resulting crude residue was purified by flash chromatography over silica gel (eluting with a gradient of 0 to 15% methanol in dichloromethane) to afford 35.0 mg of a white solid (mixture of isomers). The mixture of isomers was purified by preparative HPLC.

HPLC preparative method: reverse phase C18 Gemini column, 5 micrometer 30×100 mm, 40 mL/minute flow rate, gradient of acetonitrile/0.1% formic acid:water/0.1% formic acid; 25 to 50% acetonitrile/0.1% formic acid over 18 minutes; UV detection: 220 nm.

HPLC analytical method: reverse phase C18 Gemini column, 5 μm 4.6×150 mm, 1 mL/minute flow rate, gradient of acetonitrile/0.1% trifluoroacetic acid:water/0.1% trifluoroacetic acid; 5 to 100% acetonitrile/0.1% trifluoroacetic acid over 12 minutes; UV detection: 220 nm.

10A: (2.2 mg, 4.5% yield) $R_t$=7 minutes (analytical method); the fractions containing the product were concentrated under reduced pressure.

MS (LCMS) 421.4 (M+H$^+$; positive mode) 465.3 (M+HCO$_2^-$, negative mode). $^1$H NMR (400 MHz, methanol-d$_4$) delta ppm 1.33 (t, J=7.0 Hz, 3H), 3.53 (d, J=8.0 Hz, 1H), 3.57 (dd, J=7.5, 1.5 Hz, 1H), 3.60-3.67 (m, 2H), 3.75 (dd, J=8.3, 1.3 Hz, 1H), 3.81 (d, J=12.5 Hz, 1H), 3.89 (s, 2H), 3.96 (q, J=6.9 Hz, 2H), 4.12 (d, J=7.4 Hz, 1H), 6.77 (m, 2H), 7.00 (dd, J=9.4, 8.2 Hz, 1H), 7.08 (m, 2H), 7.36-7.41 (m, 2H).

10B: (1.8 mg, 3.7% yield) $R_t$=7.13 minutes (analytical method); the fractions containing the product were concentrated under reduced pressure.

MS (LCMS) 421.4 (M+H$^+$; positive mode) 465.3 (M+HCO$_2^-$, negative mode). $^1$H NMR (400 MHz, methanol-d$_4$) delta ppm 1.34 (t, J=7.0 Hz, 3H), 3.51 (d, J=7.4 Hz, 1H), 3.75 (d, 1H, J=12.5 Hz), 3.82-4.01 (m, 8H), 4.03 (d, J=7.4 Hz, 1H), 6.79 (m, 2H), 7.02 (dd, J=9.8, 8.4 Hz, 1H), 7.10 (m, 2H), 7.41-7.49 (m, 2H).

Note: after preparative HPLC, the fraction containing these products were concentrated and repurified by flash chromatography over silica gel (eluting with a gradient of 0 to 10% methanol in dichloromethane).

Example 11

(1S,2S,3S,4R,5S)-5-{4-fluoro-3-[4-(tetrahydro-furan-3-yloxy)-benzyl]-phenyl}-1-hydroxymethyl-6,8-dioxa-bicyclo[3.2.1]octane-2,3,4-triol (11A)

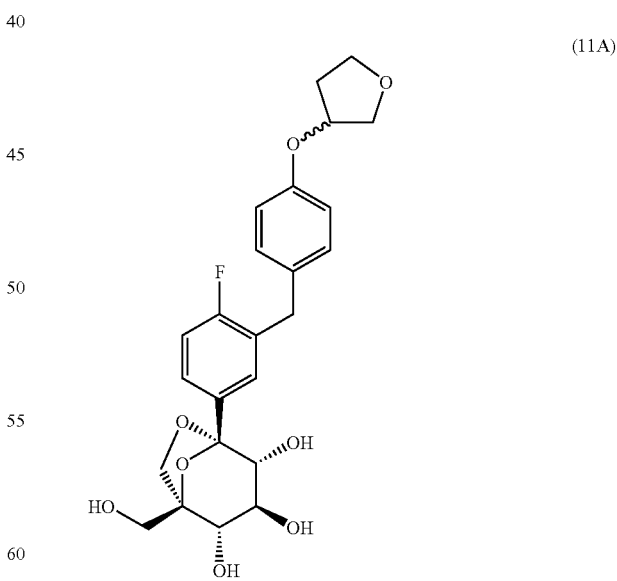

(11A)

To a solution of ((2S,3S)-2,3,4-tris-benzyloxy-5-{4-fluoro-3-[4-(tetrahydro-furan-3-yloxy)-benzyl]-phenyl}-6,8-dioxa-bicyclo[3.2.1]oct-1-yl)-methanol I-11k (160.0 mg, 0.218 mmol) in a 4:1 solution of ethanol/tetrahydrofuran (10 mL) was added successively formic acid (185 microL, 4.64 mmol) and palladium black (148 mg, 1.39 mmol). The resulting mixture was stirred at room temperature. After 3 hours, additional formic acid (185 microL, 4.64 mmol) and palladium black (148 mg, 1.39 mmol) were added. After 5 hours, the reaction mixture was filtered and the filtrate was concentrated under reduced pressure. The resulting crude residue was purified by flash chromatography over silica gel (eluting with a gradient of 0 to 15% methanol in dichloromethane) to afford 100 mg of a white solid (mixture of isomers). The mixture of isomers was purified by preparative HPLC.

HPLC preparative method: reverse phase C18 Gemini column, 5 micrometer 30×100 mm, 40 mL/minute flow rate, gradient of acetonitrile/0.1% formic acid:water/0.1% formic acid; 25 to 50% acetonitrile/0.1% formic acid over 18 minutes; UV detection: 220 nm.

HPLC analytical method: reverse phase C18 Gemini column, 5 micrometer 4.6×150 mm, 1 mL/minute flow rate, gradient of acetonitrile/0.1% trifluoroacetic acid:water/0.1% trifluoroacetic acid; 5 to 100% acetonitrile/0.1% trifluoroacetic acid over 12 minutes; UV detection: 220 nm.

11A: (19 mg, 19% yield) $R_t$=6.43 minutes (analytical method); the fractions containing the product were concentrated under reduced pressure.

$^1$H NMR (400 MHz, methanol-$d_4$) delta ppm 2.03-2.11 (m, 1H), 2.15-2.25 (m, 1H), 3.55 (d, 1H, J=8 Hz), 3.59 (dd, 1H, J=7.4 and 1 Hz), 3.61-3.69 (m, 2H), 3.77 (dd, J=8.2 and 1 Hz, 1H), 3.81-3.96 (m, 7H), 4.14 (d, J=7.4 Hz, 1H), 4.94-4.98 (m, 1H), 6.79 (m, 2H), 7.02 (dd, J=9.9, 8.5 Hz, 1H), 7.12 (m, 2H), 7.37-7.45 (m, 2H).

Example 12

(1S,2S,3S,4R,5S)-5-[3-(4-chlorobenzyl)-4-fluorophenyl]-1-hydroxymethyl-6,8-dioxabicyclo[3.2.1]octane-2,3,4-triol (12A) and (1S,2S,3S,4S,5S)-5-[3-(4-chlorobenzyl)-4-fluorophenyl]-1-hydroxymethyl-6,8-dioxabicyclo[3.2.1]octane-2,3,4-triol (12B)

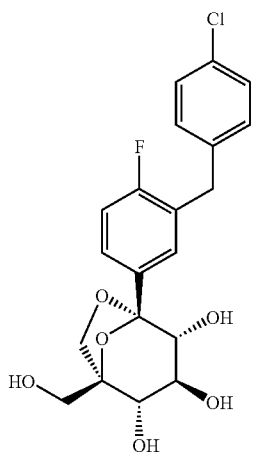

(12A)

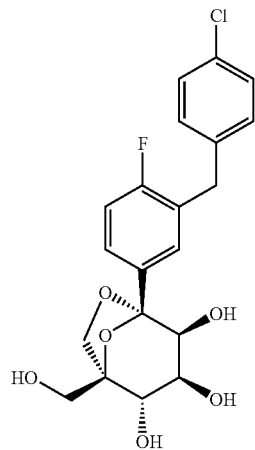

(12B)

To a mixture of intermediate I-12k (102 mg) and palladium black (98 mg, 6.1 equivalents) in ethanol/tetrahydrofuran (2 mL, 4/1 volume) was added formic acid (0.9 mL) and the resulting mixture was stirred at room temperature. After 1 hour, additional palladium black (67 mg, 4.2 equivalents) was added and the mixture was allowed to stir for an additional hour at room temperature. The palladium was removed by filtration through Celite® and the filtrate was concentrated, giving the product mixture. This material was combined with a second batch of crude material (prepared from intermediate I-12k (80 mg) following the procedure described above) for purification by preparative HPLC.

HPLC preparative conditions: reverse phase C18 Gemini column 5 micrometer 30×100 mm, flow rate 40 mL/minute, gradient of acetonitrile/0.1% formic acid:water/0.1% formic acid; 25 to 50% of acetonitrile/0.1% formic acid over 18 minutes), UV detection: 220 nm.

HPLC analytical method: reverse phase C18 Gemini column, 5 μm 4.6×150 mm, 1 mL/minute flow rate, gradient of acetonitrile/0.1% trifluoroacetic acid:water/0.1% trifluoroacetic acid; 5 to 100% acetonitrile/0.1% trifluoroacetic acid over 12 minutes; UV detection: 220 nm.

12A: (18 mg, 16% yield) $R_t$=7.11 minutes (analytical method); MS (LCMS) 411.3 (M+H$^+$; positive mode); 409.2 (M−H$^+$; negative mode). $^1$H NMR (400 MHz, methanol-$d_4$) delta ppm 7.45-7.42 (m, 2H), 7.25 (d, J=8.4 Hz, 2H), 7.19 (d, J=8.4 Hz, 2H), 7.05 (dd, J=9.6, 9.2 Hz, 1H), 4.15 (d, J=7.6 Hz, 1H), 3.98 (s, 2H), 3.84 (d, J=12.4 Hz, 1H), 3.78 (dd, J=8.4, 1.2 Hz, 1H), 3.68 (d, J=12.8 Hz, 1H), 3.66 (t, J=8.2 Hz, 1H), 3.60 (dd, J=7.4, 1.4 Hz, 1H), 3.56 (d, J=7.6 Hz, 1H).

12B: (12 mg, 11% yield) $R_t$=7.25 minutes (analytical method); MS (LCMS) 411.3 (M+H$^+$; positive mode); 409.1 (M−H$^+$; negative mode). $^1$H NMR (400 MHz, methanol-$d_4$) delta ppm 7.52-7.45 (m, 2H), 7.25 (d, J=8.4 Hz, 2H), 7.19 (d, J=8.4 Hz, 2H), 7.05 (dd, J=9.8, 8.6 Hz, 1H), 4.05 (d, J=7.2 Hz, 1H), 3.98 (s, 2H), 3.91-3.84 (m, 4H), 3.76 (d, J=12.4 Hz, 1H), 3.52 (d, J=7.6 Hz, 1H).

Example 13

(1S,2S,3S,4R,5S)-5-{4-fluoro-3-[4-(oxetan-3-yloxy)-benzyl]-phenyl}-1-hydroxymethyl-6,8-dioxa-bicyclo[3.2.1]octane-2,3,4-triol (13A)

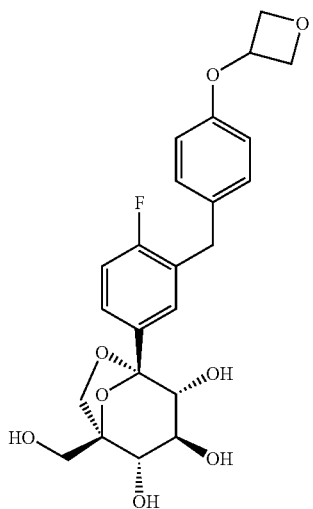

(13A)

To a solution of ((2S,3S)-2,3,4-tris-benzyloxy-5-{4-fluoro-3-[4-(oxetan-3-yloxy)-benzyl]-phenyl}-6,8-dioxa-bicyclo[3.2.1]oct-1-yl)-methanol I-13k (300 mg, 0.417 mmol) in a 4:1 solution of ethanol/tetrahydrofuran (10 mL) was added successively formic acid (333 microL, 8.34 mmol) and palladium black (266 mg, 2.50 mmol). The resulting mixture was stirred at room temperature. After 3 hours, additional formic acid (333 microL, 8.34 mmol) and palladium black (266 mg, 2.50 mmol) were added. After 5 hours, the reaction mixture was filtered and the filtrate was concentrated under reduced pressure. The resulting crude residue was purified by flash chromatography over silica gel (eluting with a gradient of 0 to 15% methanol in dichloromethane) to afford 153.0 mg of a white solid (mixture of isomers). The mixture of isomers was purified by preparative HPLC.

HPLC preparative method: reverse phase C18 Gemini column, 5 micrometer 30×100 mm, 40 mL/minute flow rate, gradient of acetonitrile/0.1% formic acid:water/0.1% formic acid; 25 to 50% acetonitrile/0.1% formic acid over 18 minutes; UV detection: 220 nm.

13A: (23 mg, 12% yield) $R_t$=7.9 minutes; the fractions containing the product were concentrated under reduced pressure.

$^1$H NMR (400 MHz, methanol-$d_4$) delta ppm 3.52 (d, J=7.8 Hz, 1H), 3.57 (d, J=7.2 Hz, 1H), 3.60-3.68 (m, 2H), 3.75 (d, J=8.2 Hz, 1H), 3.81 (d, J=12.5 Hz, 1H), 3.89 (s, 2H), 4.12 (d, J=7.4 Hz, 1H), 4.63 (dd, J=7.3, 4.8 Hz, 2H), 4.95 (t, J=6.5 Hz, 2H), 5.16-5.23 (m, 1H), 6.63 (m, 2H), 7.00 (dd, J=9.7, 8.5 Hz, 1H), 7.10 (m, 2H), 7.36-7.42 (m, 2H).

Example 14

(1S,2S,3S,4R,5S)-5-{4-chloro-3-[4-(oxetan-3-yloxy)-benzyl]-phenyl}-1-hydroxymethyl-6,8-dioxa-bicyclo[3.2.1]octane-2,3,4-triol (14A)

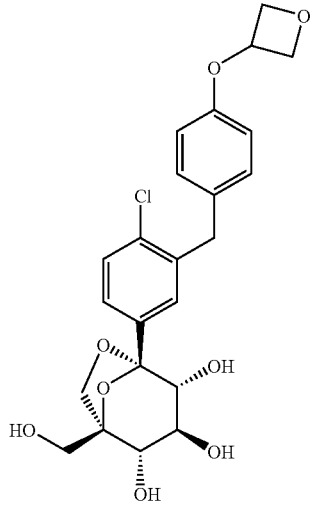

(14A)

To a solution of intermediate ((2S,3S)-2,3,4-tris-benzyloxy-5-{4-chloro-3-[4-(oxetan-3-yloxy)-benzyl]-phenyl}-6,8-dioxa-bicyclo[3.2.1]oct-1-yl)-methanol I-14k (182 mg) in ethanol/tetrahydrofuran (14 mL, 4/1 volume) was added successively formic acid (190 microL, 20 equivalents) and palladium black (106 mg, 4 equivalents) and the resulting mixture was stirred at room temperature. After 2 hours an additional 1 mL of tetrahydrofuran was added and the resulting mixture was stirred at room temperature for a additional hour. At this point additional formic acid (190 microL, 20 equivalents) and palladium black (106 mg, 4 equivalents) were added and the mixture was allowed to stir for an additional hour at room temperature. The palladium was filtered and the crude mixture obtained after evaporation of solvent (containing a mixture of isomers) was purified by HPLC preparative.

HPLC preparative method: reverse phase C18 Xbridge column 5 micrometer 100×30 mm, flow rate 40 mL/minute, gradient of acetonitrile/0.1% formic acid:water/0.1% formic acid; 30 to 55% of acetonitrile/0.1% formic acid over 11 minutes; UV detection: 220 nm.

14A: (20 mg, 17% yield); $R_t$=4.43 minutes; the fractions containing the product were concentrated under reduced pressure resulting in a white solid.

MS (LCMS) 465.3 (M+H$^+$; positive mode); 509.2 (M+HCO$_2^-$; negative mode). $^1$H NMR (400 MHz, methanol-$d_4$) delta ppm 3.53 (d, J=8.0 Hz, 1H), 3.58 (dd, J=7.4, 1.4 Hz, 1H), 3.64 (t, J=8.2 Hz, 1H), 3.67 (d, J=12.4 Hz, 1H), 3.77 (dd, J=8.4, 1.4 Hz, 1H), 3.83 (d, J=12.6 Hz, 1H), 4.03 (s, 2H), 4.14 (d, J=7.4 Hz, 1H), 4.65 (m, 2H), 4.97 (t, J=6.6 Hz, 2H), 5.22 (m, 1H), 6.65 (m, 2H), 7.11 (m, 2H), 7.34 (d, J=8.4 Hz, 1H), 7.38 (dd, J=8.4, 2.2 Hz, 1H), 7.45 (d, J=2.0 Hz, 1H).

Example 15

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-proline to give (15)

L-proline dissolved in water (approximately 480 mg/mL) was added to the example 4A compound (approximately 80 moles L-proline per mole (example 4A compound)). Volume was doubled with ethanol and solution was capped and stirred for approximately 12 hours. Volume was reduced by half by evaporation on the bench. Volume was doubled using ethanol and the volume of solution was again reduced by half using evaporation. Solid was recovered using centrifugal filtration.

Example 16

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-proline to give (16)

L-proline dissolved in water (approximately 480 mg/mL) was added to the example 4A compound (approximately 59 moles L-proline per mole example 4A compound). Volume was doubled with methanol and solution was clear. Volume was increased by 25% using acetone. Solution was capped and stirred for approximately 12 hours. Volume was reduced by approximately 60% through evaporation on the bench. Volume was doubled using methanol and remaining solvent was evaporated leaving solid white precipitate.

Example 17

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-proline to give (17)

A solution of ethanol saturated with L-proline was added to the example 4A compound (approximately 2.2 moles L-proline per mole example 4A compound) in a glass vial. Clear solution was capped and stirred for approximately 72 hours. Volume was reduced by half by evaporation at room temperature. Precipitate was seen and vial was capped and stirred for approximately 12 hours. White solid was collected using centrifugal filtration.

Example 18

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-proline to give (18)

L-proline dissolved in water (330 mg/mL) was dripped into approximately 2 mL of the example 4A compound dissolved in isopropanol (98 mg/mL) until solution became cloudy. After 15-20 minutes precipitation was observed and suspension became thick. Approximately 8 mL of water was added and solution was capped and stirred overnight. White solid was collected using vacuum filtration and dried in a 50° C. vac oven for approximately 2 hours.

Example 19

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-pyroglutamic acid to give (19)

153 microL of the compound (4A) in isopropyl alcohol (97.97 mg/mL) was pipetted into 500 microL of L-pyroglutamic acid in water (213.0 mg/mL). Solution was capped and stirred overnight. Approximately 5-10 mg more solid L-pyroglutamic acid was added. 100 microL of ethanol was added. Solution was capped and stirred overnight. Ethanol was added until total volume was adjusted to approximately 2 mL. Solution was uncapped and left in hood overnight. Approximately 10-30 mg more example 4A compound was added. Solution was capped and stirred for approximately 2 days. White precipitate was seen. Suspension was pipetted into a Co-star microcentrifuge tube equipped with a 0.45 microm nylon filter membrane insert. Solution was centrifuged until solid was separated from solution. Cocrystal (19) was recovered.

Example 20

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-pyroglutamic acid to give (20)

4-5 mL of a 1:1 ethanol/water solution was saturated with L-pyroglutamic acid (412.1 mg/mL). 730 mg of the example 4A compound was added to 3.2 mL of the L-pyroglutamic acid solution. After approximately 1 minute, precipitation was seen. The solution was too thick to stir therefore 2 mL of a 1:1 ethanol/water solution was added. The solution was stirred overnight. The solid was collected using vacuum filtration on a 0.45 microm nylon filter membrane. The solid was dried in a 50° C. vacuum oven for approximately 2 hours. Approximately 960 mg of the cocrystal complex (20) was recovered. The stoichiometric ratio of Example 4A compound to L-pyroglutamic acid was determined using quantitative NMR to be 1:1.63. Excess L-pyroglutamic acid was removed by suspending the material in ethanol yielding 1:1 co-crystal (20).

Example 21

Cocrystallization of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) with L-pyroglutamic acid to give (21)

494 mg of the example 4A compound was dissolved in 1.5 mL solution of isopropanol and ethanol (4:1 respectively). 917.2 mg of L-pyroglutamic acid was dissolved in 3 mL water. Both solutions were heated to 40° C. 200 microL of L-pyroglutamic acid solution was added to example 4A compound solution every minute until all solution was transferred (both solutions capped unless solution was being transferred). Vial with L-pyroglutamic acid solution was washed with 200 microL ethanol and solution was transferred to example 4A compound solution. Solution was stirred for 5 minutes and then heat was turned off (solution cooled at approximately 1 degree Celsius every 3 minutes). At 30° C., solution was placed on ambient temperature stirrer and stirred at 20° C. for 20 minutes. Solution was clear. Approximately 2 mL of dry seeds were added. Suspension became thick over the next 2 hours. Solution was stirred overnight. Solid was recovered using vacuum filtration on a Pyrex 2 mL 10-15M sintered glass funnel filter. Solid was dried for 24 hours in a 50° C. vacuum oven.

Example 22

Cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-proline and cocrystal of (1S,2S,3S,4R, 5S)-5-[4-chloro-3-(4-ethoxy-benzyl)-phenyl]-1-hydroxymethyl-6,8-dioxa-bicyclo[3.2.1]octane-2,3, 4-triol (Example 4A compound) and L-pyroglutamic acid Powder X-ray Diffraction Analysis: The powder X-ray diffraction patterns of the cocrystal of example 4A compound with L-proline and the cocrystal of example 4A compound with L-pyroglutamic acid were carried out on a Bruker D5000 diffractometer using copper radiation (wavelength: 1.54056 Å). The tube voltage and amperage were set to 40 kV and 40 mA, respectively. The divergence and scattering slits were set at 1 mm, and the receiving slit was set at 0.6 mm. Diffracted radiation was detected by a Kevex PSI detector. A theta-two theta continuous scan at 2.4° per minute (1 second per 0.040 step) from 3.0 to 40° 2θ was used. An alumina standard was analyzed to check the instrument alignment. Data were collected and analyzed using Bruker axis software Version 7.0. Samples were prepared by placing them in a quartz holder. It should be noted that Bruker Instruments purchased Siemens; thus, Bruker D5000 instrument is essentially the same as a Siemens D5000. Eva Application 13.0.0.3 software was used to visualize and evaluate PXRD spectra. PXRD data files (.raw) were not processed prior to peak searching. Generally, a Threshold value of 2 and a Width value of 0.3 were used to make preliminary peak assignments. The output of automated assignments was visually checked to ensure validity and adjustments manually made if necessary.

To perform an X-ray diffraction measurement on a Bragg-Brentano instrument like the Bruker system used for measurements reported herein, the sample is typically placed into a holder which has a cavity. The sample powder is pressed by a glass slide or equivalent to ensure a random surface and proper sample height. The sample holder is then placed into the instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in XRPD peak positions. A systematic study showed that, using a Shimadzu XRD-6000 in the typical Bragg-Brentano configuration, sample height difference of 1 mm lead to peak shifts as high as 1° 2θ (Chen et al.; *J Pharmaceutical and Biomedical Analysis,* 2001; 26, 63). These shifts can be identified from the X-ray Diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Bruker into agreement with the expected peak positions and may be in the range of 0 to 0.2° 2θ.

The powder X-ray diffraction values are generally accurate to within ±0.2 2-theta degrees, due to slight variations of instrument and test conditions.

Figure 3:
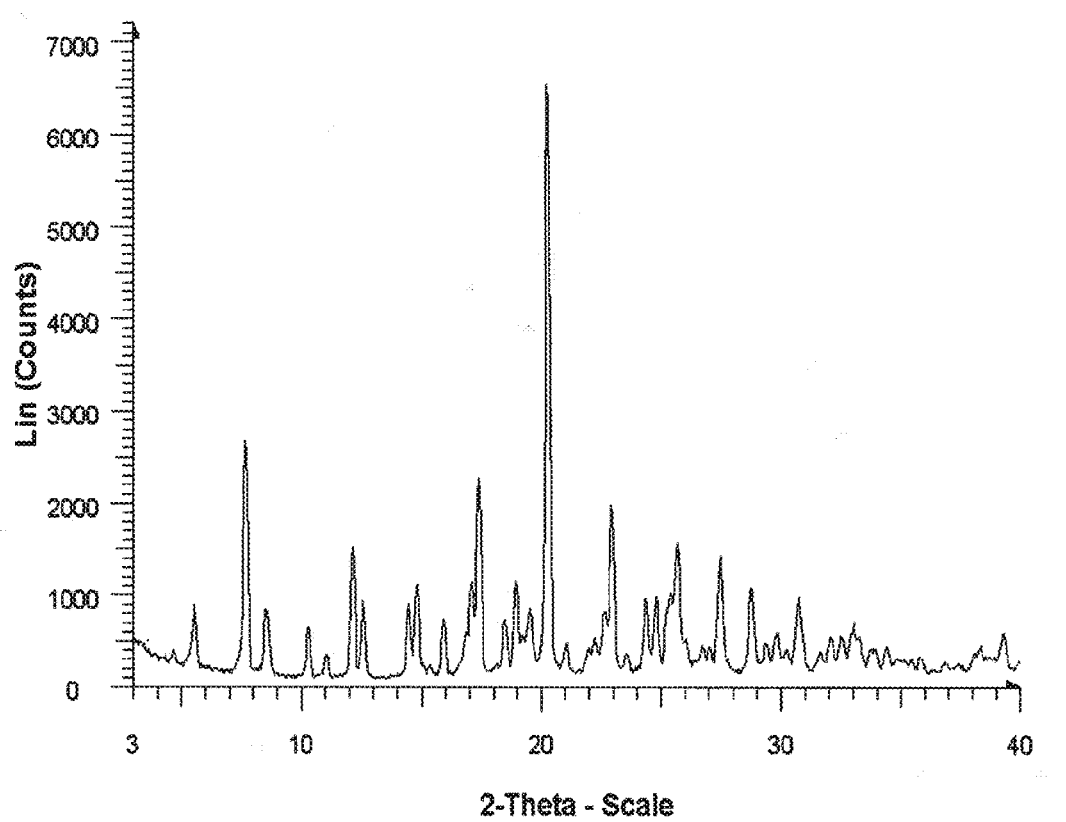
FIG. 3 represents an observed powder X-ray diffraction pattern for Example 22: Example 18 Cocrystal of Example 4A compound and L-proline

Cocrystal of example 4A compound and L-proline from Example 18 characterized by the following powder x-ray diffraction pattern, provided in FIG. 3, expressed in terms of the degree 2θ and relative intensities with a relative intensity of ≧2.7% measured on a Bruker D5000 diffractometer with CuKα radiation:

| Angle (Degree 2θ) | Relative Intensity* (≧2.7%) |
| --- | --- |
| 4.6 | 5.1 |
| 5.5 | 12.8 |
| 7.6 | 40.2 |
| 8.5 | 11.9 |
| 10.3 | 9.1 |
| 11.0 | 4.5 |
| 12.1 | 22.3 |
| 12.6 | 13.5 |
| 14.4 | 13.1 |
| 14.8 | 16.1 |
| 15.3 | 2.7 |
| 15.9 | 10.4 |
| 16.5 | 3.0 |
| 16.8 | 8.2 |
| 17.0 | 16.6 |
| 17.4 | 33.9 |
| 18.1 | 2.9 |
| 18.4 | 10.3 |
| 18.9 | 16.8 |
| 19.5 | 12.2 |
| 20.3 | 100.0 |
| 21.0 | 6.5 |
| 22.0 | 5.5 |
| 22.2 | 7.1 |
| 22.6 | 11.5 |
| 22.9 | 29.3 |
| 23.5 | 4.5 |
| 24.3 | 13.8 |
| 24.8 | 14.2 |
| 25.4 | 14.7 |
| 25.7 | 23.2 |
| 26.0 | 6.9 |
| 26.8 | 5.9 |
| 27.0 | 5.8 |
| 27.5 | 21.2 |
| 28.8 | 15.5 |
| 29.4 | 6.5 |
| 29.8 | 8.2 |
| 30.2 | 5.3 |
| 30.7 | 14.1 |
| 31.7 | 5.2 |
| 32.1 | 7.4 |
| 32.5 | 7.7 |
| 33.0 | 9.9 |
| 33.3 | 7.5 |
| 33.8 | 5.5 |
| 34.4 | 5.8 |
| 35.5 | 3.4 |
| 35.8 | 4.0 |
| 36.9 | 3.1 |

-continued

| Angle (Degree 2θ) | Relative Intensity* (≧2.7%) |
|---|---|
| 37.4 | 2.9 |
| 38.2 | 4.7 |
| 38.3 | 6.0 |
| 39.3 | 8.0 |

*The relative intensities may change depending on the crystal size and morphology.

Characteristic 2θ Peaks or Combinations of Cocrystal of Example 4A Compound and L-Proline

| Angle (Degree 2θ) |
|---|
| 7.6 |
| 12.1 |
| 20.3 |
| 28.8 |

Figure 4:
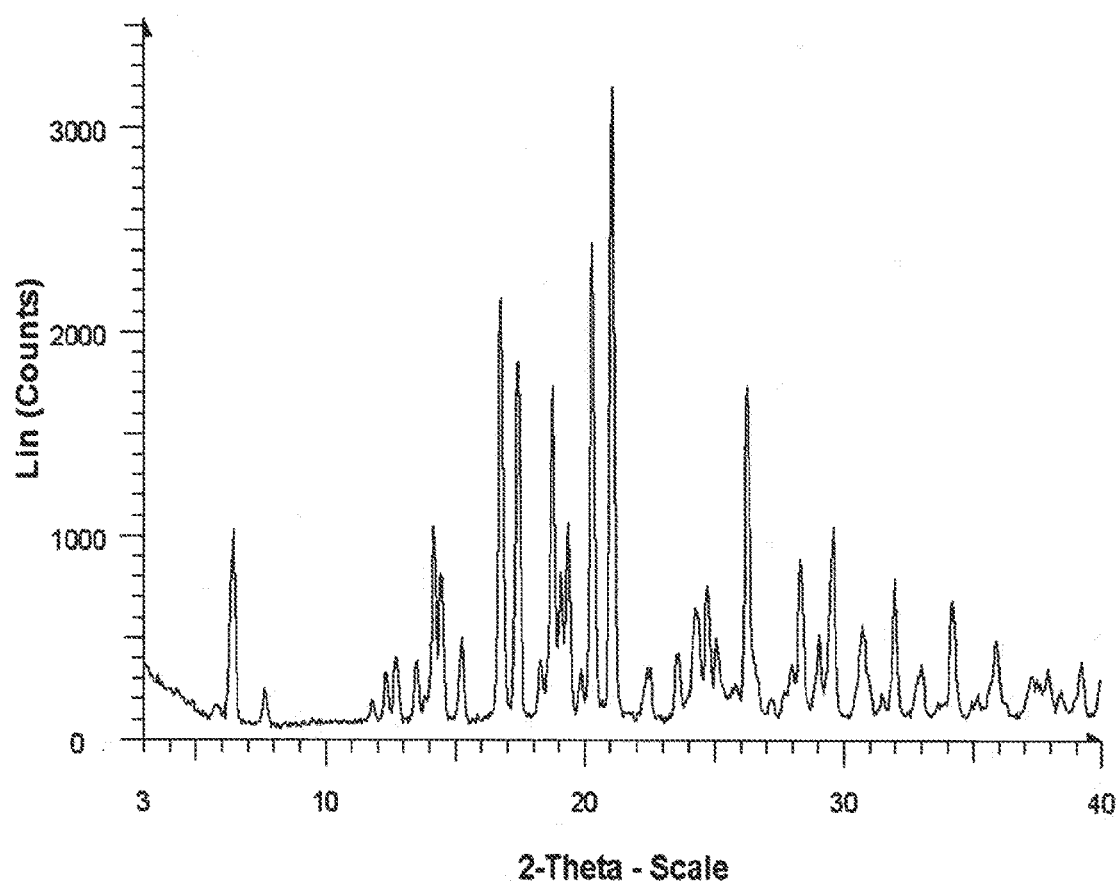
FIG. 4 represents an observed powder X-ray diffraction pattern for Example 22: Example 20 Cocrystal of Example 4A compound and L-pyroglutamic acid

Cocrystal of example 4A compound and L-pyroglutamic acid from Example 20 characterized by the following powder x-ray diffraction pattern, provided in FIG. 4, expressed in terms of the degree 2θ and relative intensities with a relative intensity of ≧2.7% measured on a Bruker D5000 diffractometer with CuKα radiation:

| Angle (Degree 2θ) | Relative Intensity* (≧4.3%) |
|---|---|
| 6.4 | 31.0 |
| 7.6 | 5.9 |
| 11.8 | 4.3 |
| 12.3 | 8.8 |
| 12.7 | 11.0 |
| 13.5 | 10.4 |
| 14.2 | 31.3 |
| 14.4 | 24.0 |
| 15.2 | 13.9 |
| 16.7 | 66.8 |
| 17.4 | 57.1 |
| 18.3 | 10.5 |
| 18.7 | 53.3 |
| 19.1 | 24.2 |
| 19.3 | 32.0 |
| 19.8 | 9.2 |
| 20.3 | 75.6 |
| 21.1 | 100.0 |
| 22.5 | 9.2 |
| 23.6 | 11.7 |
| 24.3 | 18.7 |
| 24.7 | 22.2 |
| 25.0 | 14.2 |
| 26.2 | 53.4 |
| 27.2 | 4.6 |
| 27.9 | 10.0 |
| 28.3 | 26.3 |
| 29.0 | 14.5 |
| 29.5 | 31.3 |
| 30.7 | 16.2 |
| 31.5 | 5.4 |
| 32.0 | 23.2 |
| 33.0 | 9.9 |
| 34.2 | 19.9 |
| 35.2 | 5.4 |
| 35.9 | 13.6 |
| 37.3 | 8.3 |

-continued

| Angle (Degree 2θ) | Relative Intensity* (≧4.3%) |
|---|---|
| 37.9 | 9.5 |
| 38.4 | 6.1 |
| 39.2 | 10.3 |

*The relative intensities may change depending on the crystal size and morphology.

Characteristic 2θ Peaks or Combinations of Cocrystal of Example 4A Compound and L-Pyroglutamic Acid

| Angle (Degree 2θ) |
|---|
| 6.4 |
| 16.7 |
| 17.4 |
| 21.1 |

Example 23

Cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-proline and cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-pyroglutamic acid Differential Scanning Calorimetry Thermogram Analysis:
Thermograms were obtained on a TA Instruments Q1000 Differential Scanning Calorimeter (DSC). 1-2 mg of sample was placed in aluminum sample pans and then covered with a pierced lid. The energy was measured against an empty pan as the temperature increased from 25° C. to 200-300° C. at 10° C. per minute. The onset temperature of the melting endotherm was reported as the melting temperature. The onset temperature of the melting endotherm is dependent on the rate of heating, the purity of the sample, size of crystal and sample, among other factors. Typically, the DSC results are accurate to within about ±2° C., preferably to within ±1.5° C.

Figure 5:
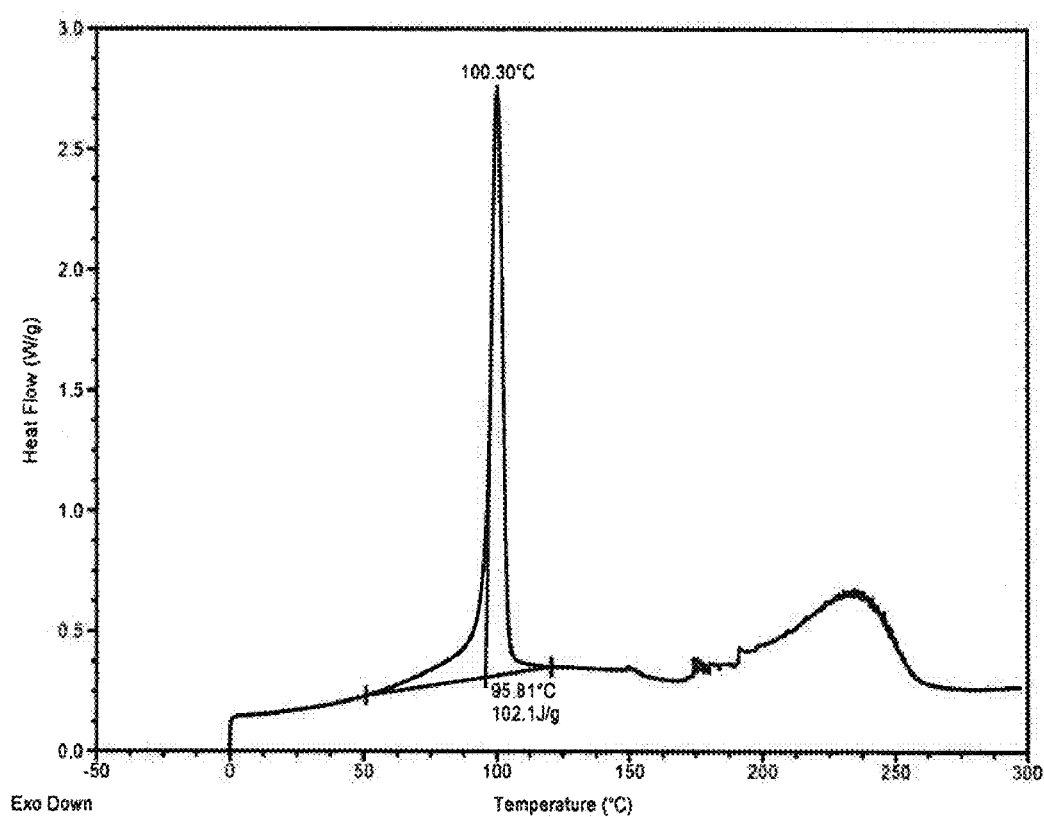
FIG. 5 represents an observed differential scanning calorimetry thermogram for Example 23: Example 18 Cocrystal of Example 4A compound and L-proline

Example 18 cocrystal of Example 4A compound and L-proline DSC results are shown in FIG. 5.

Figure 6:
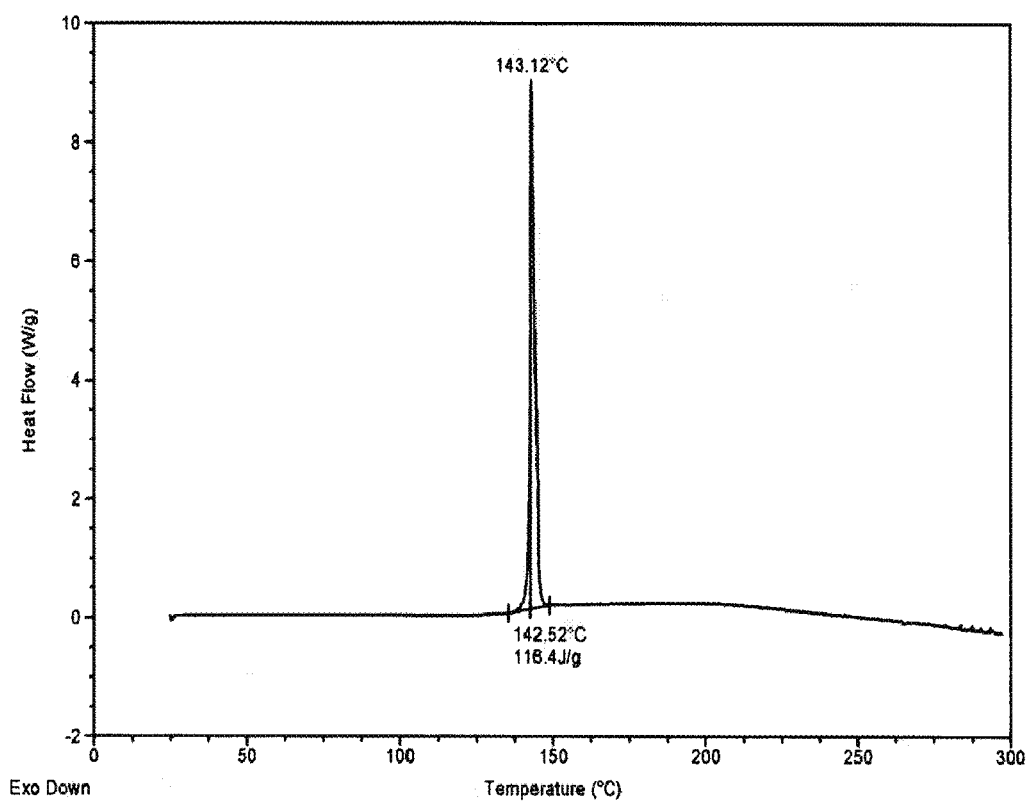
FIG. 6 represents an observed differential scanning calorimetry thermogram for Example 23: Example 20 Cocrystal of Example 4A compound and L-pyroglutamic acid

Example 20 cocrystal of Example 4A compound and L-pyroglutamic acid DSC results are shown in FIG. 6.

Example 24

Cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-proline Single Crystal X-Ray Analysis. A representative crystal using the filtrate from example 17 and concentrating via slow evaporation was surveyed and a 0.85 Å data set (maximum sin Θ/λ=0.60) was collected on a Bruker APEX diffractometer. Friedel pairs were collected in order to facilitate the determination of the absolute configuration. Atomic scattering factors were taken from the International Tables for Crystallography, Vol. C, pp. 219, 500, Kluwer Academic Publishers, 1992. All crystallographic calculations were facilitated by the SHELXTL system, Version 5.1, Bruker AXS, 1997. All diffractometer data were collected at room temperature. Pertinent crystal, data collection, and refinement are summarized in Table 24-1.

A trial structure was obtained by direct methods. This trial structure refined routinely except the unexpected water molecule and the conformational disorder with the L-proline. The L-proline was modeled with ~60/40 occupancy in the "half-chair" and "envelope" conformations A very similar disorder was observed in H. D. Flack, *Acta Crystallogr.*, A39, 876, 1983.

The hydrogen atoms bonded to N1, O6 and O7 located by difference Fourier techniques and allowed to refine with distances restrained. The relevant hydrogen atoms bonded to O5 were located from Fourier techniques, but was deleted and placed in idealized location (HFIX 83). The relevant hydrogen atom bonded to O4 could not be found with Fourier techniques and was placed in an idealized location (HFIX 83). The hydrogen atoms on the water molecule could not be located and were left out of the solution. The hydrogen parameters were added to the structure factor calculations but were not refined. The shifts calculated in the final cycles of least squares refinement were all less than 0.1 of the corresponding standard deviations. The final R-index was 5.15%. A final difference Fourier revealed no missing or misplaced electron density.

Figure 7:
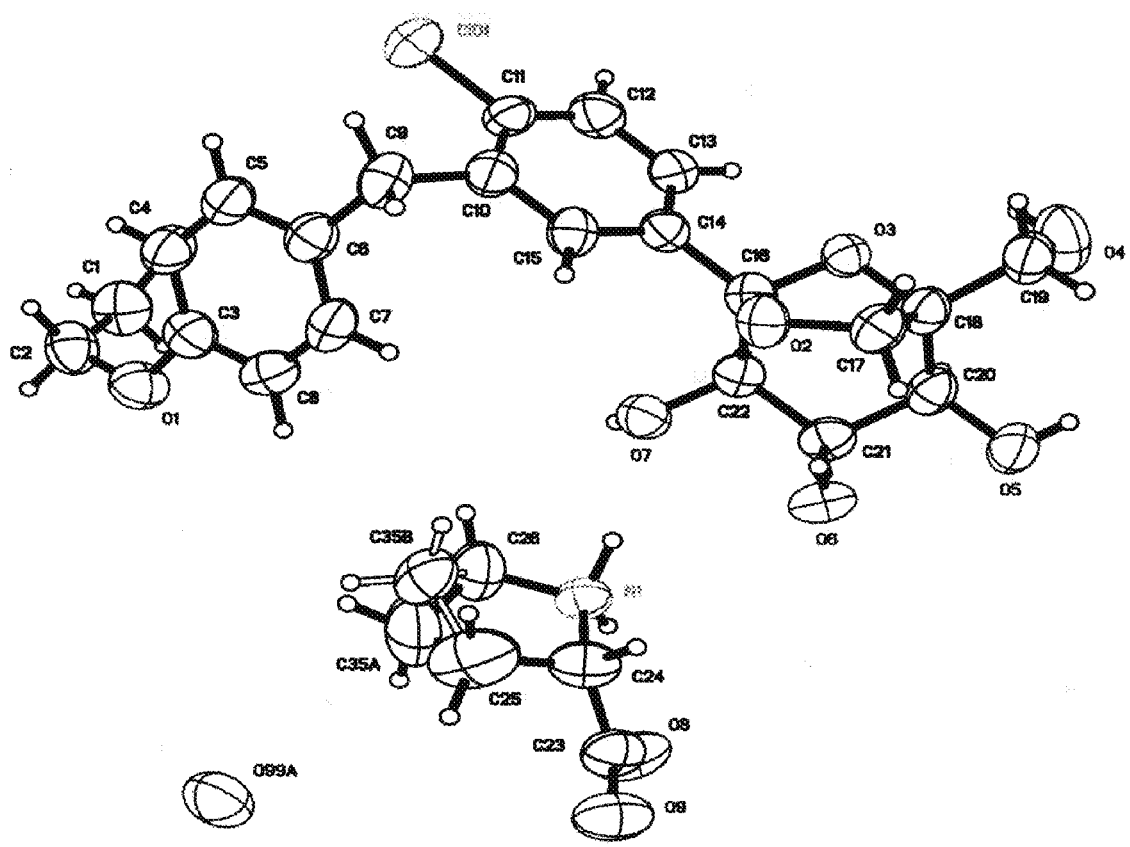
FIG. 7 represents the refined crystal structure for the Example 24: Cocrystal of Example 4A compound and L-proline which was plotted using the SHELXTL plotting package

The refined structure was plotted using the SHELXTL plotting package (FIG. 7). The absolute configuration was determined by the method of Flack[4]. Coordinates, anisotropic temperature factors, distances and angles are available as supplementary material (Tables 24-2 to 24-5).

TABLE 24-1

Crystal data and structure refinement for Example 24

| | |
|---|---|
| Empirical formula | $C_{22}H_{25}ClO_7$, $C_5H_9NO_2$, $H_2O$ |
| Formula weight | 570.02 |
| Temperature | 298(2) K |
| Wavelength | 1.54178 Å |
| Crystal system | Monoclinic |
| Space group | C2 |
| Unit cell dimensions | a = 32.8399(16) Å   α = 90°. |
| | b = 7.2457(4) Å   β = 101.268(5)°. |
| | c = 11.8023(6) Å   γ = 90°. |
| Volume | 2754.2(2) Å$^3$ |
| Z | 4 |
| Density (calculated) | 1.375 Mg/m$^3$ |
| Absorption coefficient | 1.729 mm$^{-1}$ |
| F(000) | 1208 |
| Crystal size | 0.08 × 0.16 × 0.92 mm$^3$ |
| Theta range for data collection | 2.74 to 65.58°. |
| Index ranges | -38 <= h <= 37, -8 <= k <= 6, -13 <= l <= 13 |
| Reflections collected | 6261 |
| Independent reflections | 2922 [R(int) = 0.0526] |
| Completeness to theta = 65.58° | 74.9% |
| Absorption correction | None |
| Refinement method | Full-matrix least-squares on F$^2$ |
| Data/restraints/parameters | 2922/5/380 |
| Goodness-of-fit on F$^2$ | 0.953 |
| Final R indices [I > 2sigma(I)] | R1 = 0.0515, wR2 = 0.1304 |
| R indices (all data) | R1 = 0.0581, wR2 = 0.1334 |
| Absolute structure parameter | 0.02(3) |
| Extinction coefficient | 0.0027(2) |
| Largest diff. peak and hole | 0.252 and -0.210 e · Å$^{-3}$ |

TABLE 24-2

Atomic coordinates (×10$^4$) and equivalent isotropic displacement parameters (Å$^2$ × 10$^3$) for Example 24. U(eq) is defined as one third of the trace of the orthogonalized U$_{ij}$ tensor.

| | x | y | z | U(eq) |
|---|---|---|---|---|
| Cl(01) | 7251(1) | 14669(2) | 1220(1) | 73(1) |
| N(1) | 5586(1) | 4836(6) | 1285(3) | 52(1) |
| O(1) | 6821(1) | 9986(6) | 5726(3) | 66(1) |
| C(1) | 6691(2) | 13136(9) | 6328(5) | 78(2) |
| O(2) | 6311(1) | 7637(5) | -1948(2) | 50(1) |
| C(2) | 6929(2) | 11374(9) | 6600(4) | 66(1) |
| O(3) | 5936(1) | 10106(4) | -2723(2) | 46(1) |
| C(3) | 6973(1) | 10182(7) | 4725(4) | 55(1) |
| O(4) | 5415(2) | 10596(7) | -4969(4) | 89(1) |
| C(4) | 7278(2) | 11410(8) | 4564(4) | 62(1) |
| C(5) | 7411(2) | 11447(8) | 3506(4) | 59(1) |
| O(5) | 5145(1) | 6652(5) | -3818(3) | 66(1) |
| C(6) | 7237(1) | 10299(7) | 2618(4) | 53(1) |
| O(6) | 5092(1) | 7027(5) | -1397(3) | 63(1) |
| O(7) | 5878(1) | 7968(5) | 33(3) | 54(1) |
| C(7) | 6932(2) | 9079(7) | 2793(4) | 59(1) |
| O(8) | 5009(1) | 2361(6) | 1421(4) | 78(1) |
| C(8) | 6804(2) | 8992(8) | 3838(5) | 59(1) |
| O(9) | 5409(1) | -82(6) | 1265(4) | 76(1) |
| C(9) | 7365(1) | 10429(8) | 1443(4) | 59(1) |
| C(10) | 7014(1) | 11175(7) | 533(4) | 51(1) |
| C(11) | 6926(1) | 13040(7) | 382(4) | 52(1) |
| C(12) | 6592(2) | 13693(7) | -395(4) | 58(1) |
| C(13) | 6331(1) | 12460(7) | -1057(3) | 52(1) |
| C(14) | 6401(1) | 10583(6) | -950(3) | 44(1) |
| C(15) | 6744(1) | 9959(7) | -151(3) | 49(1) |
| C(16) | 6104(1) | 9260(6) | -1659(4) | 47(1) |
| C(17) | 6125(1) | 7179(7) | -3112(4) | 51(1) |
| C(18) | 5775(1) | 8575(6) | -3448(4) | 49(1) |
| C(19) | 5720(2) | 9220(7) | -4695(4) | 59(1) |
| C(20) | 5363(1) | 8012(7) | -3103(4) | 51(1) |
| C(21) | 5455(1) | 7344(7) | -1843(4) | 50(1) |
| C(22) | 5739(2) | 8727(6) | -1085(4) | 46(1) |
| C(23) | 5335(2) | 1609(8) | 1299(4) | 62(1) |
| C(24) | 5698(2) | 2825(8) | 1186(5) | 63(1) |
| C(25) | 6072(2) | 2583(12) | 2141(9) | 105(3) |
| C(26) | 5826(2) | 5594(10) | 2391(5) | 74(2) |
| C(35A) | 6000(5) | 4000(30) | 3036(13) | 126(7) |
| C(35B) | 6229(4) | 4430(20) | 2538(15) | 71(5) |
| O(99A) | 5382(2) | 3257(7) | 6727(5) | 101(2) |

TABLE 24-3

Bond lengths [Å] and angles [°] for Example 24

| | |
|---|---|
| Cl(01)—C(11) | 1.761(4) |
| N(1)—C(26) | 1.492(7) |
| N(1)—C(24) | 1.513(7) |
| N(1)—H(98A) | 0.977(18) |
| N(1)—H(98B) | 1.00(2) |
| O(1)—C(3) | 1.377(5) |
| O(1)—C(2) | 1.434(7) |
| C(1)—C(2) | 1.499(8) |
| C(1)—H(03C) | 0.9600 |
| C(1)—H(03D) | 0.9600 |
| C(1)—H(03E) | 0.9600 |
| O(2)—C(17) | 1.430(5) |
| O(2)—C(16) | 1.434(5) |
| C(2)—H(03F) | 0.9700 |
| C(2)—H(03G) | 0.9700 |
| O(3)—C(16) | 1.409(5) |
| O(3)—C(18) | 1.437(5) |
| C(3)—C(4) | 1.379(7) |
| C(3)—C(8) | 1.386(7) |
| O(4)—C(19) | 1.405(7) |
| O(4)—H(4A) | 0.8200 |
| C(4)—C(5) | 1.401(7) |
| C(4)—H(025) | 0.9300 |
| C(5)—C(6) | 1.371(7) |
| C(5)—H(2) | 0.9300 |
| O(5)—C(20) | 1.400(6) |

TABLE 24-3-continued

Bond lengths [Å] and angles [°] for Example 24

| | |
|---|---|
| O(5)—H(5) | 0.8200 |
| C(6)—C(7) | 1.383(7) |
| C(6)—C(9) | 1.528(6) |
| O(6)—C(21) | 1.413(5) |
| O(6)—H(99A) | 0.95(2) |
| O(7)—C(22) | 1.420(5) |
| O(7)—H(99B) | 0.93(2) |
| C(7)—C(8) | 1.380(7) |
| C(7)—H(026) | 0.9300 |
| O(8)—C(23) | 1.235(7) |
| C(8)—H(033) | 0.9300 |
| O(9)—C(23) | 1.251(7) |
| C(9)—C(10) | 1.513(7) |
| C(9)—H(02A) | 0.9700 |
| C(9)—H(02B) | 0.9700 |
| C(10)—C(11) | 1.386(7) |
| C(10)—C(15) | 1.392(7) |
| C(11)—C(12) | 1.369(7) |
| C(12)—C(13) | 1.373(7) |
| C(12)—H(027) | 0.9300 |
| C(13)—C(14) | 1.381(7) |
| C(13)—H(021) | 0.9300 |
| C(14)—C(15) | 1.394(6) |
| C(14)—C(16) | 1.501(6) |
| C(15)—H(030) | 0.9300 |
| C(16)—C(22) | 1.536(6) |
| C(17)—C(18) | 1.526(6) |
| C(17)—H(02C) | 0.9700 |
| C(17)—H(02D) | 0.9700 |
| C(18)—C(19) | 1.520(6) |
| C(18)—C(20) | 1.540(6) |
| C(19)—H(03H) | 0.9700 |
| C(19)—H(03I) | 0.9700 |
| C(20)—C(21) | 1.537(6) |
| C(20)—H(4) | 0.9800 |
| C(21)—C(22) | 1.533(6) |
| C(21)—H(015) | 0.9800 |
| C(22)—H(013) | 0.9800 |
| C(23)—C(24) | 1.510(7) |
| C(24)—C(25) | 1.506(10) |
| C(24)—H(029) | 0.9800 |
| C(25)—C(35B) | 1.479(17) |
| C(25)—C(35A) | 1.52(2) |
| C(25)—H(34A) | 0.9700 |
| C(25)—H(34B) | 0.9700 |
| C(26)—C(35A) | 1.440(19) |
| C(26)—C(35B) | 1.548(14) |
| C(26)—H(03A) | 0.9700 |
| C(26)—H(03B) | 0.9700 |
| C(35A)—H(35A) | 0.9700 |
| C(35A)—H(35B) | 0.9700 |
| C(35B)—H(35C) | 0.9700 |
| C(35B)—H(35D) | 0.9700 |
| C(26)—N(1)—C(24) | 109.1(4) |
| C(26)—N(1)—H(98A) | 107(2) |
| C(24)—N(1)—H(98A) | 109(3) |
| C(26)—N(1)—H(98B) | 97(3) |
| C(24)—N(1)—H(98B) | 119(3) |
| H(98A)—N(1)—H(98B) | 114(4) |
| C(3)—O(1)—C(2) | 117.7(4) |
| C(2)—C(1)—H(03C) | 109.5 |
| C(2)—C(1)—H(03D) | 109.5 |
| H(03C)—C(1)—H(03D) | 109.5 |
| C(2)—C(1)—H(03E) | 109.5 |
| H(03C)—C(1)—H(03E) | 109.5 |
| H(03D)—C(1)—H(03E) | 109.5 |
| C(17)—O(2)—C(16) | 106.6(3) |
| O(1)—C(2)—C(1) | 113.4(5) |
| O(1)—C(2)—H(03F) | 108.9 |
| C(1)—C(2)—H(03F) | 108.9 |
| O(1)—C(2)—H(03G) | 108.9 |
| C(1)—C(2)—H(03G) | 108.9 |
| H(03F)—C(2)—H(03G) | 107.7 |
| C(16)—O(3)—C(18) | 103.3(3) |
| O(1)—C(3)—C(4) | 125.4(4) |
| O(1)—C(3)—C(8) | 115.1(4) |
| C(4)—C(3)—C(8) | 119.4(4) |
| C(19)—O(4)—H(4A) | 109.5 |
| C(3)—C(4)—C(5) | 119.7(5) |
| C(3)—C(4)—H(025) | 120.2 |
| C(5)—C(4)—H(025) | 120.2 |
| C(6)—C(5)—C(4) | 121.0(5) |
| C(6)—C(5)—H(2) | 119.5 |
| C(4)—C(5)—H(2) | 119.5 |
| C(20)—O(5)—H(5) | 109.5 |
| C(5)—C(6)—C(7) | 118.6(4) |
| C(5)—C(6)—C(9) | 120.7(4) |
| C(7)—C(6)—C(9) | 120.7(4) |
| C(21)—O(6)—H(99A) | 105(3) |
| C(22)—O(7)—H(99B) | 108(3) |
| C(8)—C(7)—C(6) | 121.2(4) |
| C(8)—C(7)—H(026) | 119.4 |
| C(6)—C(7)—H(026) | 119.4 |
| C(7)—C(8)—C(3) | 120.0(4) |
| C(7)—C(8)—H(033) | 120.0 |
| C(3)—C(8)—H(033) | 120.0 |
| C(10)—C(9)—C(6) | 111.2(3) |
| C(10)—C(9)—H(02A) | 109.4 |
| C(6)—C(9)—H(02A) | 109.4 |
| C(10)—C(9)—H(02B) | 109.4 |
| C(6)—C(9)—H(02B) | 109.4 |
| H(02A)—C(9)—H(02B) | 108.0 |
| C(11)—C(10)—C(15) | 116.7(4) |
| C(11)—C(10)—C(9) | 123.4(4) |
| C(15)—C(10)—C(9) | 119.8(4) |
| C(12)—C(11)—C(10) | 122.9(4) |
| C(12)—C(11)—Cl(01) | 117.6(4) |
| C(10)—C(11)—Cl(01) | 119.5(4) |
| C(11)—C(12)—C(13) | 119.1(5) |
| C(11)—C(12)—H(027) | 120.5 |
| C(13)—C(12)—H(027) | 120.5 |
| C(12)—C(13)—C(14) | 121.0(4) |
| C(12)—C(13)—H(021) | 119.5 |
| C(14)—C(13)—H(021) | 119.5 |
| C(13)—C(14)—C(15) | 118.6(4) |
| C(13)—C(14)—C(16) | 119.9(4) |
| C(15)—C(14)—C(16) | 121.4(4) |
| C(10)—C(15)—C(14) | 121.8(5) |
| C(10)—C(15)—H(030) | 119.1 |
| C(14)—C(15)—H(030) | 119.1 |
| O(3)—C(16)—O(2) | 105.4(3) |
| O(3)—C(16)—C(14) | 108.5(4) |
| O(2)—C(16)—C(14) | 111.6(3) |
| O(3)—C(16)—C(22) | 107.4(3) |
| O(2)—C(16)—C(22) | 110.3(4) |
| C(14)—C(16)—C(22) | 113.2(3) |
| O(2)—C(17)—C(18) | 104.8(3) |
| O(2)—C(17)—H(02C) | 110.8 |
| C(18)—C(17)—H(02C) | 110.8 |
| O(2)—C(17)—H(02D) | 110.8 |
| C(18)—C(17)—H(02D) | 110.8 |
| H(02C)—C(17)—H(02D) | 108.9 |
| O(3)—C(18)—C(19) | 107.4(4) |
| O(3)—C(18)—C(17) | 100.7(3) |
| C(19)—C(18)—C(17) | 113.4(4) |
| O(3)—C(18)—C(20) | 106.7(3) |
| C(19)—C(18)—C(20) | 113.1(4) |
| C(17)—C(18)—C(20) | 114.3(4) |
| O(4)—C(19)—C(18) | 112.7(4) |
| O(4)—C(19)—H(03H) | 109.0 |
| C(18)—C(19)—H(03H) | 109.0 |
| O(4)—C(19)—H(03I) | 109.0 |
| C(18)—C(19)—H(03I) | 109.0 |
| H(03H)—C(19)—H(03I) | 107.8 |
| O(5)—C(20)—C(21) | 110.0(4) |
| O(5)—C(20)—C(18) | 113.5(4) |
| C(21)—C(20)—C(18) | 108.9(3) |
| O(5)—C(20)—H(4) | 108.1 |
| C(21)—C(20)—H(4) | 108.1 |
| C(18)—C(20)—H(4) | 108.1 |
| O(6)—C(21)—C(22) | 110.6(3) |
| O(6)—C(21)—C(20) | 113.1(4) |
| C(22)—C(21)—C(20) | 109.9(4) |
| O(6)—C(21)—H(015) | 107.7 |
| C(22)—C(21)—H(015) | 107.7 |
| C(20)—C(21)—H(015) | 107.7 |

TABLE 24-3-continued

Bond lengths [Å] and angles [°] for Example 24

| | |
|---|---|
| O(7)—C(22)—C(21) | 109.7(4) |
| O(7)—C(22)—C(16) | 111.8(3) |
| C(21)—C(22)—C(16) | 110.3(3) |
| O(7)—C(22)—H(013) | 108.3 |
| C(21)—C(22)—H(013) | 108.3 |
| C(16)—C(22)—H(013) | 108.3 |
| O(8)—C(23)—O(9) | 127.9(5) |
| O(8)—C(23)—C(24) | 118.1(5) |
| O(9)—C(23)—C(24) | 114.1(5) |
| C(25)—C(24)—C(23) | 114.1(5) |
| C(25)—C(24)—N(1) | 103.3(5) |
| C(23)—C(24)—N(1) | 110.3(4) |
| C(25)—C(24)—H(029) | 109.6 |
| C(23)—C(24)—H(029) | 109.6 |
| N(1)—C(24)—H(029) | 109.6 |
| C(35B)—C(25)—C(24) | 108.3(8) |
| C(35B)—C(25)—C(35A) | 42.4(8) |
| C(24)—C(25)—C(35A) | 103.1(8) |
| C(35B)—C(25)—H(34A) | 70.3 |
| C(24)—C(25)—H(34A) | 111.2 |
| C(35A)—C(25)—H(34A) | 111.2 |
| C(35B)—C(25)—H(34B) | 137.2 |
| C(24)—C(25)—H(34B) | 111.2 |
| C(35A)—C(25)—H(34B) | 111.1 |
| H(34A)—C(25)—H(34B) | 109.1 |
| C(35A)—C(26)—N(1) | 104.8(9) |
| C(35A)—C(26)—C(35B) | 42.5(9) |
| N(1)—C(26)—C(35B) | 101.1(7) |
| C(35A)—C(26)—H(03A) | 110.8 |
| N(1)—C(26)—H(03A) | 110.8 |
| C(35B)—C(26)—H(03A) | 73.1 |
| C(35A)—C(26)—H(03B) | 110.8 |
| N(1)—C(26)—H(03B) | 110.8 |
| C(35B)—C(26)—H(03B) | 144.0 |
| H(03A)—C(26)—H(03B) | 108.9 |
| C(26)—C(35A)—C(25) | 105.8(10) |
| C(26)—C(35A)—H(35A) | 110.6 |
| C(25)—C(35A)—H(35A) | 110.6 |
| C(26)—C(35A)—H(35B) | 110.6 |
| C(25)—C(35A)—H(35B) | 110.6 |
| H(35A)—C(35A)—H(35B) | 108.7 |
| C(25)—C(35B)—C(26) | 102.7(8) |
| C(25)—C(35B)—H(35C) | 111.2 |
| C(26)—C(35B)—H(35C) | 111.2 |
| C(25)—C(35B)—H(35D) | 111.2 |
| C(26)—C(35B)—H(35D) | 111.2 |
| H(35C)—C(35B)—H(35D) | 109.1 |

TABLE 24-4

Anisotropic displacement parameters (Å² × 10³) for Example 24. The anisotropic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| Cl(01) | 77(1) | 69(1) | 69(1) | −11(1) | 1(1) | −27(1) |
| N(1) | 56(2) | 40(2) | 60(2) | 0(2) | 12(2) | 0(2) |
| O(1) | 70(2) | 70(3) | 62(2) | 2(2) | 23(2) | −3(2) |
| C(1) | 80(3) | 76(4) | 77(3) | −2(3) | 13(3) | 8(3) |
| O(2) | 47(1) | 52(2) | 49(1) | −1(2) | 3(1) | 12(1) |
| C(2) | 63(2) | 84(4) | 52(2) | 1(2) | 13(2) | 7(3) |
| O(3) | 46(1) | 43(2) | 45(2) | 2(1) | 3(1) | −1(1) |
| C(3) | 48(2) | 59(3) | 57(2) | 5(2) | 12(2) | 8(2) |
| O(4) | 111(3) | 83(3) | 62(2) | 8(2) | −10(2) | 23(3) |
| C(4) | 59(3) | 72(4) | 53(2) | −10(2) | 10(2) | −12(2) |
| C(5) | 54(2) | 66(3) | 55(2) | −6(2) | 4(2) | −11(2) |
| O(5) | 69(2) | 59(2) | 59(2) | 2(2) | −12(2) | −8(2) |
| C(6) | 41(2) | 55(3) | 59(2) | −2(2) | 4(2) | 4(2) |
| O(6) | 58(2) | 47(2) | 87(2) | −6(2) | 25(2) | −9(1) |
| O(7) | 62(2) | 49(2) | 51(2) | 2(1) | 12(1) | −1(1) |
| C(7) | 54(2) | 59(3) | 58(2) | −11(2) | −4(2) | −2(2) |
| O(8) | 63(2) | 63(3) | 116(3) | −22(2) | 36(2) | −12(2) |
| C(8) | 52(2) | 57(3) | 69(3) | −1(2) | 12(2) | −7(2) |
| O(9) | 90(2) | 52(3) | 98(2) | −8(2) | 44(2) | −7(2) |

TABLE 24-4-continued

Anisotropic displacement parameters (Å² × 10³) for Example 24. The anisotropic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| C(9) | 45(2) | 72(4) | 58(2) | −12(2) | 5(2) | 1(2) |
| C(10) | 45(2) | 61(3) | 46(2) | −4(2) | 11(2) | −3(2) |
| C(11) | 57(2) | 48(3) | 50(2) | −8(2) | 11(2) | −16(2) |
| C(12) | 75(3) | 43(3) | 57(2) | 2(2) | 12(2) | −1(2) |
| C(13) | 50(2) | 54(3) | 49(2) | 7(2) | 4(2) | −2(2) |
| C(14) | 48(2) | 44(3) | 41(2) | 1(2) | 10(2) | 0(2) |
| C(15) | 47(2) | 54(3) | 45(2) | −5(2) | 8(2) | 5(2) |
| C(16) | 45(2) | 49(3) | 47(2) | −1(2) | 8(2) | 3(2) |
| C(17) | 54(2) | 47(3) | 52(2) | −10(2) | 8(2) | −2(2) |
| C(18) | 52(2) | 44(3) | 47(2) | −6(2) | 1(2) | 0(2) |
| C(19) | 63(3) | 60(3) | 50(2) | −7(2) | 1(2) | −3(2) |
| C(20) | 45(2) | 45(3) | 56(2) | −3(2) | −3(2) | 4(2) |
| C(21) | 51(2) | 37(2) | 60(2) | −1(2) | 11(2) | 3(2) |
| C(22) | 48(2) | 40(2) | 50(2) | −2(2) | 10(2) | 5(2) |
| C(23) | 79(3) | 46(3) | 65(3) | −12(2) | 24(2) | −3(2) |
| C(24) | 63(3) | 49(3) | 84(3) | 3(2) | 30(2) | 4(2) |
| C(25) | 70(4) | 63(5) | 176(8) | 13(5) | 8(4) | 14(3) |
| C(26) | 68(3) | 79(4) | 68(3) | −3(3) | −3(3) | 8(3) |
| C(35A) | 104(11) | 178(19) | 79(8) | 29(10) | −26(8) | −30(11) |
| C(35B) | 43(6) | 73(10) | 90(9) | −3(7) | −1(6) | 4(6) |
| O(99A) | 130(4) | 76(4) | 95(3) | 14(2) | 18(3) | 9(3) |

TABLE 24-5

Hydrogen coordinates (×10⁴) and isotropic displacement parameters (Å² × 10³) for Example 24

| | x | y | z | U(eq) |
|---|---|---|---|---|
| H(98A) | 5291(6) | 4930(60) | 1320(30) | 33(9) |
| H(98B) | 5680(13) | 5750(50) | 760(30) | 51(12) |
| H(03C) | 6764 | 13698 | 5659 | 117 |
| H(03D) | 6757 | 13962 | 6973 | 117 |
| H(03E) | 6398 | 12877 | 6176 | 117 |
| H(03F) | 7223 | 11637 | 6698 | 80 |
| H(03G) | 6878 | 10893 | 7327 | 80 |
| H(4A) | 5481 | 11497 | −4553 | 134 |
| H(025) | 7394 | 12210 | 5155 | 74 |
| H(2) | 7619 | 12262 | 3404 | 71 |
| H(5) | 5097 | 7017 | −4489 | 98 |
| H(99A) | 4974(16) | 8220(40) | −1350(50) | 64(15) |
| H(99B) | 5744(13) | 8610(60) | 540(30) | 54(13) |
| H(026) | 6810 | 8302 | 2195 | 71 |
| H(033) | 6604 | 8136 | 3947 | 71 |
| H(02A) | 7604 | 11232 | 1504 | 71 |
| H(02B) | 7443 | 9215 | 1214 | 71 |
| H(027) | 6544 | 14955 | −474 | 70 |
| H(021) | 6103 | 12894 | −1584 | 62 |
| H(030) | 6793 | 8697 | −74 | 59 |
| H(02C) | 6017 | 5929 | −3159 | 61 |
| H(02D) | 6325 | 7285 | −3614 | 61 |
| H(03H) | 5982 | 9696 | −4830 | 71 |
| H(03I) | 5643 | 8173 | −5204 | 71 |
| H(4) | 5187 | 9111 | −3149 | 61 |
| H(015) | 5605 | 6171 | −1818 | 59 |
| H(013) | 5578 | 9843 | −1009 | 55 |
| H(029) | 5776 | 2606 | 438 | 76 |
| H(34A) | 6327 | 2839 | 1870 | 126 |
| H(34B) | 6084 | 1342 | 2453 | 126 |
| H(03A) | 6044 | 6414 | 2248 | 89 |
| H(03B) | 5645 | 6267 | 2805 | 89 |
| H(35A) | 5809 | 3518 | 3496 | 152 |
| H(35B) | 6259 | 4310 | 3548 | 152 |
| H(35C) | 6415 | 4913 | 2066 | 85 |
| H(35D) | 6372 | 4404 | 3339 | 85 |

Example 25

Cocrystal From Example 20 of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-pyroglutamic acid Single Crystal X-Ray Analysis. A representative crystal of a sample from Example 20 was surveyed and a 0.90 Å data set (maximum sin $\Theta/\lambda$=0.56) was collected on a Bruker APEX diffractometer. Friedel pairs were collected in order to facilitate the determination of the absolute configuration. Stereochemistry determined from the flack parameter and also from the known chirality of the coformer (L-pyroglutamic acid). Atomic scattering factors were taken from the International Tables for Crystallography, Vol. C, pp. 219, 500, Kluwer Academic Publishers, 1992. All crystallographic calculations were facilitated by the SHELXTL Version 5.1, Bruker AXS, 1997 system. All diffractometer data were collected at room temperature. Pertinent crystal, data collection, and refinement are summarized in Table 25-1.

Figure 8:
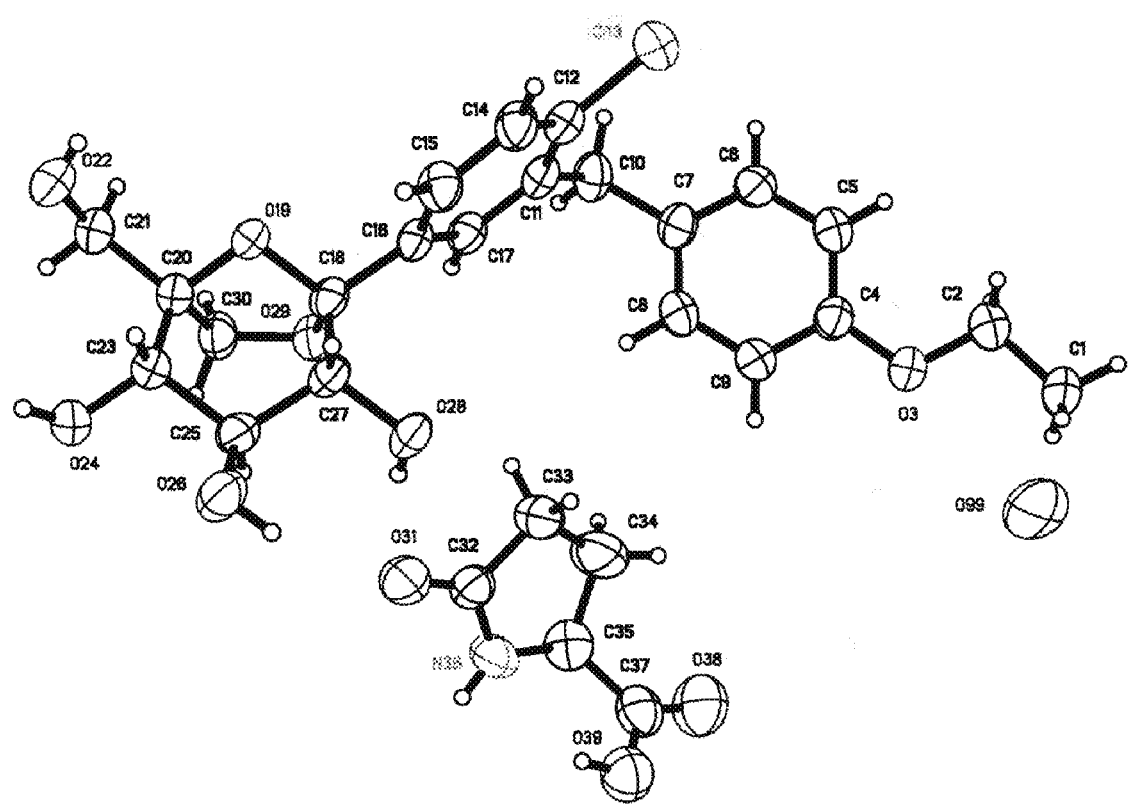
FIG. 8 represents the refined crystal structure for the Example 25: Cocrystal of Example 4A compound and L-pyroglutamic acid which was plotted using the SHELXTL plotting package.
Figure 9:
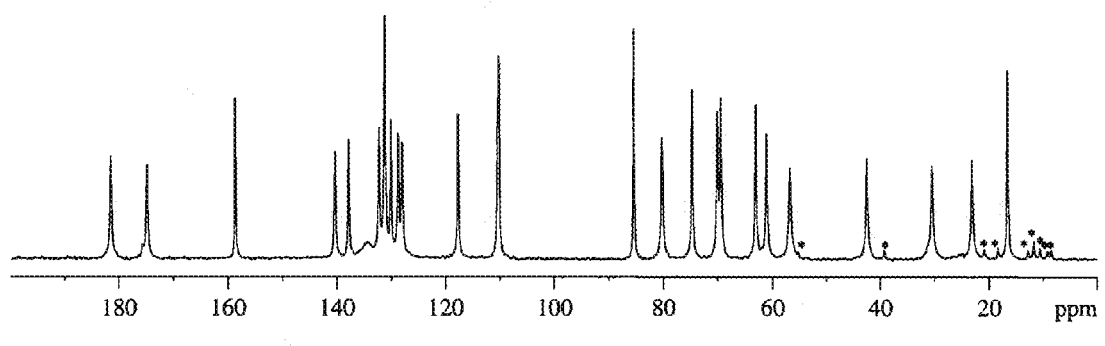
FIG. 9 represents an observed $^{13}C$ solid state nuclear magnetic resonance spectrum for Example 26: Cocrystal of Example 4A compound and L-pyroglutamic acid. The peaks marked by asterisks are spinning sidebands.

A trial structure was obtained by direct methods. This trial structure refined routinely, except for a low residual peak that was refined as 0.1 stoichiometric water. The stoichiometry of water was found by first deleting a hydroxyl group on the molecule, refining and measuring the resulting q peak; then comparing this peak to the residual peak from the water molecule. Using this method, a ratio of 1 to 0.1 (molecule to water) was estimated. Additionally, removing the water molecule from the solution and searching for void spaces in the crystal with Material Studio, Platon, and Mercury revealed a plausible volume of 33 cubic angstroms for a water molecule (water typically has about 40 cubic angstroms of space). The hydrogen atoms on nitrogen and oxygen were located by difference Fourier techniques and allowed to refine freely with no restraints. A few of the protons bonded to heteroatoms (H97a, H97b, H97c, and H97c) exhibited somewhat short bond lengths (~0.8 angstroms found vs. ~0.96 expected), yet the distances were left unrestrained. The hydrogen atoms on O99 (water) were not found from the difference map and left out of the structure solution. The hydrogen parameters were added to the structure factor calculations but were not refined. The shifts calculated in the final cycles of least squares refinement were all less than 0.2 of the corresponding standard deviations. The final R-index was 3.58%. A final difference Fourier revealed no missing or misplaced electron density. Of the residuals left, one is in a reasonable position for a proton bonded to O39 (carboxylic acid). This residual could be an additional occupancy position for the H98a proton (proton bonded to O39), but was not refined as such The refined structure was plotted using the SHELXTL plotting package (FIG. 8). The absolute configuration was determined by the method of Flack (H. D. Flack, *Acta Crystallogr.*, A39, 876, 1983). Coordinates, anisotropic temperature factors, distances and angles are available as supplementary material (Tables 25-2 through 25-5).

TABLE 25-1

Crystal data and structure refinement for Example 25.

| | |
|---|---|
| Empirical formula | $C_{22}H_{25}Cl_1O_7 * C_5H_7N_1O_3 * 0.1(H_2O)$ |
| Formula weight | 567.79 |
| Temperature | 570(2) K |
| Wavelength | 1.54178 Å |
| Crystal system | Orthorhombic |
| Space group | P2(1)2(1)2(1) |

TABLE 25-1-continued

Crystal data and structure refinement for Example 25.

| | |
|---|---|
| Unit cell dimensions | a = 7.4907(10) Å   $\alpha$ = 90°. |
| | b = 12.8626(15) Å   $\beta$ = 90°. |
| | c = 28.029(4) Å   $\gamma$ = 90°. |
| Volume | 2700.6(6) Å$^3$ |
| Z | 4 |
| Density (calculated) | 1.396 Mg/m$^3$ |
| Absorption coefficient | 1.767 mm$^{-1}$ |
| F(000) | 1196 |
| Crystal size | 0.03 × 0.2 × 0.2 mm$^3$ |
| Theta range for data collection | 3.15 to 59.28°. |
| Index ranges | −6 <= h <= 7, −13 <= k <= 14, −31 <= l <= 29 |
| Reflections collected | 9116 |
| Independent reflections | 3759 [R(int) = 0.0275] |
| Completeness to theta = 59.28° | 96.5% |
| Absorption correction | Empirical |
| Refinement method | Full-matrix least-squares on F$^2$ |
| Data/restraints/parameters | 3759/0/387 |
| Goodness-of-fit on F$^2$ | 1.032 |
| Final R indices [I > 2sigma(I)] | R1 = 0.0358, wR2 = 0.0885 |
| R indices (all data) | R1 = 0.0418, wR2 = 0.0920 |
| Absolute structure parameter | 0.010(18) |
| Extinction coefficient | 0.00067(17) |
| Largest diff. peak and hole | 0.171 and −0.136 e · Å$^{-3}$ |

TABLE 25-2

Atomic coordinates (×10$^4$) and equivalent isotropic displacement parameters (Å$^2$ × 10$^3$) for Example 25. U(eq) is defined as one third of the trace of the orthogonalized U$_{ij}$ tensor.

| | x | y | z | U(eq) |
|---|---|---|---|---|
| C(1) | 1385(7) | 9812(3) | 634(2) | 89(1) |
| C(2) | 1302(6) | 8776(3) | 399(2) | 81(1) |
| O(3) | 2546(3) | 8104(1) | 625(1) | 55(1) |
| C(4) | 2553(4) | 7080(2) | 489(1) | 43(1) |
| C(5) | 1555(5) | 6676(2) | 117(1) | 54(1) |
| C(6) | 1669(4) | 5630(2) | 13(1) | 50(1) |
| C(7) | 2745(4) | 4966(2) | 268(1) | 42(1) |
| C(8) | 3723(4) | 5385(2) | 639(1) | 50(1) |
| C(9) | 3643(4) | 6423(2) | 749(1) | 49(1) |
| C(10) | 2839(5) | 3807(2) | 157(1) | 49(1) |
| C(11) | 2248(4) | 3159(2) | 577(1) | 40(1) |
| C(12) | 467(4) | 3074(2) | 708(1) | 44(1) |
| Cl(13) | −1197(1) | 3652(1) | 362(1) | 59(1) |
| C(14) | −56(4) | 2535(2) | 1112(1) | 46(1) |
| C(15) | 1219(4) | 2055(2) | 1391(1) | 44(1) |
| C(16) | 3014(4) | 2095(2) | 1265(1) | 36(1) |
| C(17) | 3502(4) | 2652(2) | 864(1) | 38(1) |
| C(18) | 4335(3) | 1493(2) | 1560(1) | 36(1) |
| O(19) | 3862(2) | 420(1) | 1544(1) | 38(1) |
| C(20) | 5478(4) | −95(2) | 1690(1) | 39(1) |
| C(21) | 5397(4) | −1208(2) | 1525(1) | 50(1) |
| O(22) | 4012(4) | −1782(2) | 1739(1) | 62(1) |
| C(23) | 5592(4) | 18(2) | 2233(1) | 40(1) |
| O(24) | 7085(3) | −534(2) | 2419(1) | 52(1) |
| C(25) | 5750(4) | 1168(2) | 2361(1) | 43(1) |
| O(26) | 5536(3) | 1267(2) | 2861(1) | 61(1) |
| C(27) | 4393(4) | 1816(2) | 2086(1) | 39(1) |
| C(28) | 4750(3) | 2904(2) | 2136(1) | 50(1) |
| O(29) | 6093(3) | 1545(1) | 1363(1) | 44(1) |
| C(30) | 6903(4) | 529(2) | 1425(1) | 47(1) |
| O(31) | 8289(3) | 3646(2) | 2167(1) | 62(1) |
| C(32) | 8567(4) | 4451(3) | 1935(1) | 50(1) |
| C(33) | 7407(5) | 4857(3) | 1544(1) | 60(1) |
| C(34) | 8309(7) | 5813(3) | 1364(2) | 100(2) |
| C(35) | 10008(5) | 5962(3) | 1666(1) | 60(1) |
| N(36) | 9939(4) | 5092(2) | 1990(1) | 62(1) |
| C(37) | 10097(5) | 7035(3) | 1889(1) | 62(1) |
| O(38) | 10174(4) | 7793(2) | 1636(1) | 94(1) |
| O(39) | 10136(4) | 7059(2) | 2353(1) | 72(1) |
| O(99) | 470(40) | 9300(20) | 1968(10) | 97(10) |

TABLE 25-3

Bond lengths [Å] and angles [°] for Example 25.

| | |
|---|---|
| C(1)—C(2) | 1.486(5) |
| C(2)—O(3) | 1.419(4) |
| O(3)—C(4) | 1.371(3) |
| C(4)—C(9) | 1.382(4) |
| C(4)—C(5) | 1.385(4) |
| C(5)—C(6) | 1.379(4) |
| C(6)—C(7) | 1.375(4) |
| C(7)—C(8) | 1.381(4) |
| C(7)—C(10) | 1.525(4) |
| C(8)—C(9) | 1.371(4) |
| C(10)—C(11) | 1.509(4) |
| C(11)—C(12) | 1.388(4) |
| C(11)—C(17) | 1.398(4) |
| C(12)—C(14) | 1.382(4) |
| C(12)—Cl(13) | 1.746(3) |
| C(14)—C(15) | 1.381(4) |
| C(15)—C(16) | 1.391(4) |
| C(16)—C(17) | 1.381(4) |
| C(16)—C(18) | 1.504(4) |
| C(18)—O(19) | 1.426(3) |
| C(18)—O(29) | 1.430(3) |
| C(18)—C(27) | 1.532(4) |
| O(19)—C(20) | 1.440(3) |
| C(20)—C(21) | 1.507(4) |
| C(20)—C(23) | 1.529(4) |
| C(20)—C(30) | 1.529(4) |
| C(21)—O(22) | 1.408(4) |
| C(23)—O(24) | 1.424(3) |
| C(23)—C(25) | 1.527(4) |
| C(25)—O(26) | 1.418(3) |
| C(25)—C(27) | 1.523(4) |
| C(27)—O(28) | 1.430(3) |
| O(29)—C(30) | 1.452(3) |
| O(31)—C(32) | 1.239(4) |
| C(32)—N(36) | 1.327(4) |
| C(32)—C(33) | 1.494(4) |
| C(33)—C(34) | 1.491(5) |
| C(34)—C(35) | 1.539(5) |
| C(35)—N(36) | 1.443(4) |
| C(35)—C(37) | 1.517(5) |
| C(37)—O(38) | 1.206(4) |
| C(37)—O(39) | 1.301(4) |
| O(3)—C(2)—C(1) | 108.8(3) |
| C(4)—O(3)—C(2) | 117.8(2) |
| O(3)—C(4)—C(9) | 116.4(3) |
| O(3)—C(4)—C(5) | 124.5(2) |
| C(9)—C(4)—C(5) | 119.1(3) |
| C(6)—C(5)—C(4) | 119.5(3) |
| C(7)—C(6)—C(5) | 122.1(3) |
| C(6)—C(7)—C(8) | 117.4(3) |
| C(6)—C(7)—C(10) | 121.9(3) |
| C(8)—C(7)—C(10) | 120.7(3) |
| C(9)—C(8)—C(7) | 121.8(3) |
| C(8)—C(9)—C(4) | 120.1(3) |
| C(11)—C(10)—C(7) | 111.6(2) |
| C(12)—C(11)—C(17) | 117.2(2) |
| C(12)—C(11)—C(10) | 122.1(3) |
| C(17)—C(11)—C(10) | 120.6(3) |
| C(14)—C(12)—C(11) | 121.9(3) |
| C(14)—C(12)—Cl(13) | 117.8(2) |
| C(11)—C(12)—Cl(13) | 120.4(2) |
| C(15)—C(14)—C(12) | 119.3(3) |
| C(14)—C(15)—C(16) | 120.5(3) |
| C(17)—C(16)—C(15) | 118.8(3) |
| C(17)—C(16)—C(18) | 122.7(2) |
| C(15)—C(16)—C(18) | 118.4(2) |
| C(16)—C(17)—C(11) | 122.2(3) |
| O(19)—C(18)—O(29) | 105.1(2) |
| O(19)—C(18)—C(16) | 108.5(2) |
| O(29)—C(18)—C(16) | 111.6(2) |
| O(19)—C(18)—C(27) | 107.5(2) |
| O(29)—C(18)—C(27) | 109.5(2) |
| C(16)—C(18)—C(27) | 114.1(2) |
| C(18)—O(19)—C(20) | 103.16(19) |
| O(19)—C(20)—C(21) | 108.4(2) |
| O(19)—C(20)—C(23) | 106.7(2) |
| C(21)—C(20)—C(23) | 113.5(2) |
| O(19)—C(20)—C(30) | 101.9(2) |
| C(21)—C(20)—C(30) | 112.1(2) |
| C(23)—C(20)—C(30) | 113.3(2) |
| O(22)—C(21)—C(20) | 113.3(3) |
| O(24)—C(23)—C(25) | 109.6(2) |
| O(24)—C(23)—C(20) | 111.2(2) |
| C(25)—C(23)—C(20) | 109.3(2) |
| O(26)—C(25)—C(27) | 112.1(2) |
| O(26)—C(25)—C(23) | 108.1(2) |
| C(27)—C(25)—C(23) | 111.1(2) |
| O(28)—C(27)—C(25) | 111.2(2) |
| O(28)—C(27)—C(18) | 111.4(2) |
| C(25)—C(27)—C(18) | 110.9(2) |
| C(18)—O(29)—C(30) | 107.28(19) |
| O(29)—C(30)—C(20) | 103.8(2) |
| O(31)—C(32)—N(36) | 126.0(3) |
| O(31)—C(32)—C(33) | 125.4(3) |
| N(36)—C(32)—C(33) | 108.6(3) |
| C(34)—C(33)—C(32) | 105.9(3) |
| C(33)—C(34)—C(35) | 106.9(3) |
| N(36)—C(35)—C(37) | 116.5(3) |
| N(36)—C(35)—C(34) | 102.8(3) |
| C(37)—C(35)—C(34) | 112.1(3) |
| C(32)—N(36)—C(35) | 115.8(3) |
| O(38)—C(37)—O(39) | 124.4(4) |
| O(38)—C(37)—C(35) | 119.8(3) |
| O(39)—C(37)—C(35) | 115.8(3) |

TABLE 25-4

Anisotropic displacement parameters (Å² × 10³) for Example 25. The anisotropic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| C(1) | 115(4) | 49(2) | 104(3) | −20(2) | −54(3) | 31(2) |
| C(2) | 95(3) | 52(2) | 95(3) | −12(2) | −47(2) | 23(2) |
| O(3) | 62(1) | 36(1) | 68(1) | −3(1) | −17(1) | 6(1) |
| C(4) | 45(2) | 35(2) | 49(2) | 1(1) | 1(1) | 0(1) |
| C(5) | 61(2) | 43(2) | 59(2) | 4(2) | −16(2) | 9(2) |
| C(6) | 61(2) | 43(2) | 47(2) | 2(1) | −13(1) | 0(2) |
| C(7) | 50(2) | 36(2) | 41(1) | 6(1) | 7(1) | −2(1) |
| C(8) | 58(2) | 44(2) | 49(2) | 9(1) | −9(2) | 7(2) |
| C(9) | 54(2) | 43(2) | 50(2) | 2(1) | −12(1) | 3(1) |
| C(10) | 63(2) | 40(2) | 43(2) | 6(1) | 5(1) | 6(1) |
| C(11) | 52(2) | 27(1) | 41(1) | 0(1) | 4(1) | −2(1) |
| C(12) | 50(2) | 29(2) | 52(2) | 0(1) | −4(1) | −4(1) |
| Cl(13) | 59(1) | 51(1) | 66(1) | 7(1) | −16(1) | 4(1) |
| C(14) | 40(2) | 35(2) | 64(2) | 7(1) | 4(1) | −2(1) |
| C(15) | 44(2) | 39(2) | 50(2) | 11(1) | 7(1) | −4(1) |
| C(16) | 41(2) | 25(1) | 42(1) | 3(1) | 2(1) | −3(1) |
| C(17) | 36(2) | 31(2) | 45(2) | 0(1) | 5(1) | −3(1) |
| C(18) | 36(2) | 28(1) | 43(1) | 3(1) | 4(1) | −7(1) |
| O(19) | 40(1) | 28(1) | 45(1) | 2(1) | −5(1) | −5(1) |
| C(20) | 40(2) | 30(2) | 47(2) | 1(1) | −6(1) | 2(1) |
| C(21) | 57(2) | 33(2) | 60(2) | −3(2) | −12(2) | 6(1) |
| O(22) | 77(2) | 37(1) | 73(2) | 6(1) | −21(1) | −14(1) |
| C(23) | 42(2) | 32(2) | 47(2) | 2(1) | −8(1) | −2(1) |
| O(24) | 58(1) | 37(1) | 62(1) | 8(1) | −18(1) | −3(1) |
| C(25) | 52(2) | 36(2) | 42(2) | 0(1) | −7(1) | −8(1) |
| O(26) | 100(2) | 40(1) | 43(1) | −1(1) | −9(1) | −9(1) |
| C(27) | 45(2) | 28(1) | 43(1) | −2(1) | 0(1) | −6(1) |
| O(28) | 55(2) | 28(1) | 69(1) | −6(1) | −7(1) | −3(1) |
| O(29) | 36(1) | 39(1) | 56(1) | 8(1) | 7(1) | −4(1) |
| C(30) | 48(2) | 38(2) | 56(2) | 2(1) | −1(1) | 8(1) |
| O(31) | 62(2) | 56(1) | 70(1) | 7(1) | −9(1) | −12(1) |
| C(32) | 48(2) | 45(2) | 57(2) | −9(2) | −3(2) | 1(2) |
| C(33) | 57(2) | 64(2) | 58(2) | −7(2) | −12(2) | 2(2) |
| C(34) | 135(4) | 78(3) | 87(3) | 18(2) | −58(3) | −19(3) |
| C(35) | 55(2) | 61(2) | 64(2) | 5(2) | 7(2) | −3(2) |
| N(36) | 53(2) | 61(2) | 72(2) | 11(2) | −22(2) | −9(2) |
| C(37) | 49(2) | 65(2) | 72(2) | 5(2) | −1(2) | 6(2) |

TABLE 25-4-continued

Anisotropic displacement parameters (Å$^2$ × 10$^3$) for Example 25. The anisotropic displacement factor exponent takes the form: $-2\pi^2[h^2 a^{*2} U_{11} + \ldots + 2 h k a^* b^* U_{12}]$

| | $U_{11}$ | $U_{22}$ | $U_{33}$ | $U_{23}$ | $U_{13}$ | $U_{12}$ |
|---|---|---|---|---|---|---|
| O(38) | 116(2) | 70(2) | 95(2) | 19(2) | −2(2) | −11(2) |
| O(39) | 79(2) | 69(2) | 70(2) | 2(1) | 0(1) | 3(1) |
| O(99) | 90(20) | 110(20) | 89(19) | −60(18) | −2(15) | 29(17) |

TABLE 25-5

Hydrogen coordinates (×10$^4$) and isotropic displacement parameters (Å$^2$ × 10$^3$) for Example 25.

| | x | y | z | U(eq) |
|---|---|---|---|---|
| H(1A) | 1080 | 9742 | 965 | 134 |
| H(1B) | 557 | 10275 | 482 | 134 |
| H(1C) | 2571 | 10087 | 606 | 134 |
| H(2A) | 107 | 8492 | 427 | 97 |
| H(2B) | 1587 | 8843 | 63 | 97 |
| H(5) | 813 | 7106 | −61 | 65 |
| H(6) | 998 | 5365 | −239 | 60 |
| H(8) | 4455 | 4952 | 819 | 60 |
| H(9) | 4323 | 6685 | 999 | 59 |
| H(10A) | 2083 | 3655 | −115 | 58 |
| H(10B) | 4055 | 3623 | 73 | 58 |
| H(14) | −1256 | 2497 | 1194 | 56 |
| H(15) | 875 | 1701 | 1665 | 53 |
| H(17) | 4703 | 2691 | 782 | 45 |
| H(21A) | 5235 | −1219 | 1181 | 60 |
| H(21B) | 6528 | −1543 | 1595 | 60 |
| H(97D) | 3240(80) | −1700(40) | 1620(20) | 120(20) |
| H(23) | 4498 | −261 | 2375 | 48 |
| H(97C) | 6720(50) | −1040(30) | 2557(13) | 78(14) |
| H(25) | 6950 | 1407 | 2275 | 52 |
| H(97B) | 5570(50) | 1910(30) | 2942(14) | 79(13) |
| H(27) | 3214 | 1680 | 2224 | 46 |
| H(97A) | 5800(50) | 2990(30) | 2137(12) | 60(12) |
| H(30A) | 7992 | 577 | 1611 | 57 |
| H(30B) | 7175 | 214 | 1119 | 57 |
| H(33A) | 7294 | 4347 | 1291 | 71 |
| H(33B) | 6226 | 5021 | 1664 | 71 |
| H(34A) | 7528 | 6411 | 1397 | 120 |
| H(34B) | 8616 | 5735 | 1030 | 120 |
| H(35) | 11047 | 5874 | 1457 | 72 |
| H(99) | 10740(50) | 4950(20) | 2171(11) | 49(10) |
| H(98A) | 9670(60) | 6410(30) | 2507(15) | 95(14) |

Example 26

Cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-pyroglutamic acid Solid State NMR:

Approximately 80 mg of cocrystal of (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol (Example 4A compound) and L-pyroglutamic acid prepared using the process described in Scheme 2 was tightly packed into a 4 mm ZrO$_2$ rotor. Spectra were collected at room temperature and pressure on a Bruker-Biospin 4 mm BL CPMAS probe positioned into a wide-bore Bruker-Biospin DSX 500 MHz ($^1$H frequency) NMR spectrometer. The packed rotor was oriented at the magic angle and spun at 15.0 kHz. The $^{13}$C solid state spectrum was collected using a proton decoupled cross-polarization magic angle spinning experiment (CPMAS). The cross-polarization contact time was set to 2.0 ms. A proton decoupling field of approximately 85 kHz was applied. 1448 scans were collected with recycle delay of 14 seconds. The carbon spectrum was referenced using an external standard of crystalline adamantane, setting its upfield resonance to 29.5 ppm. The chemical shift data is dependent on the testing conditions (i.e. spinning speed and sample holder), reference material, and data processing parameters, among other factors. Typically, the ss-NMR results are accurate to within about ±0.2 ppm.

Carbon Chemical Shifts Observed

Characteristic Peaks are Starred

All Peaks are (±0.2 ppm)

| $^{13}$C Chemical Shifts [ppm]$^a$ | Intensity$^b$ |
|---|---|
| 16.5* | 9.3 |
| 23.1 | 4.8 |
| 30.5 | 4.5 |
| 42.5 | 4.9 |
| 56.7 | 4.5 |
| 61.0 | 6.2 |
| 63.0 | 7.6 |
| 69.4 | 8.0 |
| 70.0 | 7.2 |
| 74.7 | 8.4 |
| 80.2 | 6.0 |
| 85.3 | 11.4 |
| 110.1 | 10.0 |
| 110.4 | 7.9 |
| 117.7 | 7.1 |
| 127.9 | 5.7 |
| 128.7 | 6.2 |
| 130.0 | 6.9 |
| 131.1* | 12.0 |
| 132.2 | 6.5 |
| 134.4 | 0.8 |
| 137.8 | 5.9 |
| 140.3 | 5.3 |
| 158.7* | 7.9 |
| 174.7 | 4.5 |
| 181.5* | 5.0 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Pharmacological Testing

The practice of the instant invention for the treatment of diseases modulated by the inhibition of SGLT2 can be evidenced by activity in at least one of the protocols described hereinbelow.

Biological Assays

In-Vitro Assay

The SGLT2 functional assay was designed to detect the inhibition of methyl-alpha-D glucopyranoside (AMG—a non-metabolizable form of glucose) uptake via the SGLT2 transporter. The SGLT2 transporter recovers glucose from the proximal tubules of the kidney; its inhibition results in sugar wasted in the urine. The positive control compound, Phlorizin, is a known inhibitor of glucose uptake for SGLT2 and was used for comparing the high percent effect of SGLT2 inhibition of the test compounds.

CHO-FlpIn (Invitrogen, Carlsbad, Calif.) cells stably expressing human SGLT2 (pcDNA5/FRT) were plated in Iso-TC 96 well plates (Perkin Elmer, Waltham, Mass.) at a density of 100,000 cells/well in 100 microL of growth media (1:1 F-12/DMEM media (Gibco, Carlsbad, Calif.), 10% FBS (Sigma, St. Louis Mo.), 1× Pen/Strep (Gibco, Carlsbad, Calif.), 600 microg/mL Hygromycin (Invitrogen, Carlsbad, Calif.)). Prior to treating with test compound, confluent cells were serum starved for 2 hours at 37° C. in 1:1 F-12/DMEM media, replacing with fresh F-12/DMEM media after 1 hour. Test compounds in dimethylsulfoxide (Sigma, St. Louis, Mo.) were diluted 100 fold in uptake buffer (140 mM NaCl (Promega, Madison, Wis.), 2 mM KCl (Teknova, Hollister, Calif.), 1 mM $CaCl_2$ (Teknova, Hollister, Calif.), 1 mM $MgCl_2$ (Teknova, Hollister, Calif.), and 10 mM HEPES (Gibco, Carlsbad, Calif.) to cell plates pre-rinsed with uptake buffer. Cells were pre-incubated with test compound for 15 minutes prior to the addition of 50 microL AMG (40 nCi AMG [U-$^{14}$C] (Perkin Elmer, Waltham, Mass.) in unlabelled AMG (Aldrich, St. Louis, Mo.)) per well yielding a final concentration of 11.3.3 microM AMG. Cell plates were then incubated for 3 hours at 37° C. for AMG uptake. After incubation, cells were washed twice with ice cold wash buffer (uptake buffer containing 200 microM Phlorizin (Sigma), air dried and lysed in 30 microL of 200 mM NaOH and 1% SDS buffer on an orbital shaker. Microscint 40 (Perkin Elmer, Waltham, Mass.) was added to the lysed cells (giving a final volume of 200 microL) and mixed by orbital shaking for 30 minutes. Plates were stored in the dark overnight and quantitated in the 1540 Microbeta Trilux (Wallac, Waltham, Mass.) using a normalized protocol for $^{14}$C detection. The percent effect of test compounds to inhibit AMG uptake was calculated using the following calculation:

[% Effect=((ZPE−T)/(ZPE−HPE))×100%]

where "ZPE" is the corrected counts per minute (CCPM) in control wells containing 0.5% DMSO, T is the CCPM in wells containing test compound at various concentrations of the standard curve, and HPE is the high percent effect referring to the CCPM in control wells containing 10 microM Phlorizin. The $IC_{50}$ values were calculated using a dose response equation and are summarized for the compounds tested in Table 3.

Abbreviations used in the in vitro testing description include:

| | |
|---|---|
| SGLT2 | type 2 sodium/glucose co-transporter |
| AMG | methyl-α-D Glucopyranoside |
| DMEM | Dulbecco's Modified Eagle's Medium |
| IC50 | 50% Inhibition Concentration |
| FBS | Fetal Bovine Serum |
| DMSO | Dimethylsulfoxide |
| SDS | Sodium Dodecyl Sulfate |
| CHO-FlpIn | Chinese Hamster Ovary cell containing the FRT site |

TABLE 3

| Test Compound | Run No. | hSGLT1 $IC_{50}$ nM | hSGLT2 $IC_{50}$ nM |
|---|---|---|---|
| 1A | 1 | 1080 | 1.55 |
| | 2 | 454 | 1.15 |
| | 3 | 327 | 0.779 |
| | 4 | 562 | 0.715 |
| | 5 | 262 | 0.654 |
| | 6 | 359 | 1.61 |

TABLE 3-continued

| Test Compound | Run No. | hSGLT1 $IC_{50}$ nM | hSGLT2 $IC_{50}$ nM |
|---|---|---|---|
| 2A | 1 | 1240 | 0.827 |
| | 2 | >1000 | 1.53 |
| | 3 | >1000 | 0.942 |
| | 4 | >1000 | 0.741 |
| | 5 | 679 | 1.58 |
| | 6 | undetermined | 1.05 |
| 3A | 1 | 543 | 0.479 |
| | 2 | 397 | 0.972 |
| | 3 | 550 | 1.39 |
| | 4 | 757 | 0.811 |
| | 5 | 523 | 0.602 |
| | 6 | 672 | 0.588 |
| | 7 | 380 | 1.35 |
| 3B | 1 | >10000 | 41.6 |
| | 2 | >10000 | 40.8 |
| | 3 | >10000 | 27.9 |
| | 4 | undetermined | 62.2 |
| 4A | 1 | 1590 | 1.27 |
| | 2 | 1010 | 0.816 |
| | 3 | 1750 | 0.57 |
| | 4 | >1000 | 0.922 |
| | 5 | >1000 | 1.85 |
| | 6 | 2090 | 0.812 |
| | 7 | 1810 | 0.7 |
| | 8 | 2860 | 0.737 |
| | 9 | 2480 | 0.846 |
| | 10 | 2840 | 0.768 |
| 4B | 1 | >1000 | 122 |
| | 2 | >10000 | 66.8 |
| | 3 | undetermined | 81.7 |
| 5A | 1 | >10000 | 4.5 |
| | 2 | >1000 | 81.7 |
| | 3 | 5790 | 2.42 |
| | 4 | undetermined | 1.77 |
| 5B | 1 | >10000 | 186 |
| 6A | 1 | >10000 | 18.7 |
| | 2 | >1000 | 9.99 |
| | 3 | >1000 | 13.5 |
| | 4 | >1000 | 13.4 |
| | 5 | 8930 | 5.71 |
| | 6 | undetermined | 7.67 |
| 7A | 1 | >1000 | 10.6 |
| | 2 | >10000 | 6.38 |
| | 3 | >1000 | 5.88 |
| | 4 | undetermined | 6.11 |
| 10A | 1 | >10,000 | 4.08 |
| | 2 | >3330 | 33.4 |
| | 3 | >3160 | 2.54 |
| 10B | 1 | >10,000 | 127 |
| | 2 | >10,000 | 103 |
| 11A | 1 | >10,000 | 9.6 |
| | 2 | >10,000 | 11.9 |
| | 3 | >10,000 | 19.8 |
| | 4 | >10,000 | 7.13 |
| 12A | 1 | >10,000 | 11.1 |
| | 2 | 5780 | 7.41 |
| | 3 | >10,000 | 8.85 |
| | 4 | >10,000 | 0.802 |
| | 5 | >10,000 | 10.7 |
| | 6 | >10,000 | 14.1 |
| 12B | 1 | >3160 | 32.3 |
| 13A | 1 | >10,000 | 14.9 |
| | 2 | >10,000 | 17.8 |
| 14A | 1 | >10,000 | 2.28 |
| | 2 | >10,000 | 3.12 |
| | 3 | >10,000 | 2.39 |
| | 4 | >10,000 | 2.87 |

In-Vivo Assay

Examples 1A and 4A were tested in rats to assess inhibition of glucose transport via urinary glucose excretion. Male Sprague Dawley rats (~300 g) were singly housed in metabolic cages for urine collection. Rats had access to standard laboratory chow and water ad libitum. Rats (n=2 to 5/group)

received vehicle or compound by oral gavage. Dosing solutions were 0.03 mg/mL, 0.3 mg/mL, 0.9 mg/mL, 3 mg/mL, 9 mg/mL and 18 mg/mL for the 0.1 mg/kg, 1 mg/kg, 3 mg/kg, 10 mg/kg, 30 mg/kg and 60 mg/kg doses respectively. Dosing volume was 1 mL/300 g of body weight for all doses. One group received a 10 mg/kg dose of Example 1A and others received 0.1, 1, 3, 10, 30 or 60 mg/kg dose of Example 4A. The vehicle was 20% v/v PEG400 and 24% v/v hydroxypropyl beta cyclodextrin; HPBCD. Following oral administration, urine was collected for 24 hours. Glucose concentration was measured in urine by UV absorbance spectrophotometry at 340 nm using a Roche Hitachi 917 spectrophotometer (Diamond Diagnostics, Holliston, Mass.). The total amount of glucose excreted in the urine was calculated as the product of urine concentration and urine volume using the formula below:

urinary glucose excreted (mg)/200 g body weight=urinary glucose concentration (mg/dL)× urine volume (dL)×200/rat body weight (g).

Amounts of urinary glucose excreted (UGE) were obtained from rats for Example 1A and Example 4A by the method described above and are shown in Table 4. Blood (0.1 mL) was collected from the PK satellite group animals at 1, 2, 4, 7, 24 hours postdose to obtain plasma and analyzed by LC-MS/MS. Mean PK parameters at the various doses tested are shown in Table 4.

TABLE 4

| Compound | Dose (mg/kg) | Mean UGE (mg/200 g of body weight) ± SEM (n = 5) | Mean PK Parameters (n = 2) | | |
|---|---|---|---|---|---|
| | | | Cmax (ng/mL) | tmax (h) | AUC(0-24) (ng * h/mL) |
| Example 1A | 10 | 2049 ± 382.2 | 1260 | 1.00 | 6630 |
| Example 4A | 0.1 | 389.0 ± 62.54 | 43.4 | 1.50 | 188 |
| Example 4A | 1 | 1519 ± 52.02 | 372 | 1.00 | 2000 |
| Example 4A | 3 | 1937 ± 101.1 | 1320 | 1.00 | 7080 |
| Example 4A | 10 | 2145 ± 132.3 | 3100 | 2.50 | 26400 |
| Example 4A | 30 | 2554 ± 141.1 | 10500 | 1.00 | 10700 |
| Example 4A | 60 | 2437 ± 116.7 | 25300 | 2.00 | 233000 |

SEM: Standard error of the mean.

Pharmacokinetic Testing in Rats

Examples 1A, 2A, 4A, 12A, and 14A were tested in rats to assess pharmacokinetic parameters including maximum concentration (Cmax), area under the plasma concentration time curve (AUC), clearance (CL), steady state volume of distribution (Vss), half life ($t_{1/2}$), and bioavailability (F). Male Sprague Dawley rats (~300 g) were used. Rats received compound by intravenous (IV) or oral gavage (PO) administration and the doses tested including vehicle to formulate dosing solutions are listed in Table 5.

Following IV or PO administration, 0.2 mL blood was sampled from the jugular vein at various timepoints (Table 5). Twenty microL aliquots of plasma samples and standards were subjected to protein precipitation with acetonitrile containing an internal standard. Samples were vortexed and centrifuged to obtain supernatant which was analyzed by LC-MS/MS. Analyst (Version 1.4.1) was used to measure peak areas and peak area ratios of analyte to internal standard were calculated. LC-MS/MS conditions are as follows: Mass Spectrometer+Source Type was Sciex API 4000–Turbo Spray; HPLC pump was Shimadzu; Autosampler was CTC PAL Autosampler; Injection volume was 3.0 to 10 microL; A gradient was used with mobile phase A: 10 mM ammonium acetate and 1% Isopropyl alcohol in water; B: Acetonitrile; Flowrate 0.300 mL per minute (Column 2.0×30 mm 5 microm LUNA C18 column (phenomenex)). Detection mode was negative.

A calibration curve was constructed from the peak area ratios of the standards to the internal standard by applying a weighted linear (1/x or 1/x2) regression. The dynamic range of the standard curve was 5.00 ng/mL to 5000 ng/mL.

Pharmacokinetic parameters were determined from individual animal data using non-compartmental analysis in Watson (version 7.2). Concentrations below the limit of quantitation (BLQ) were recorded as 0 ng/mL for use in calculations.

The following calculations were used:

AUC(0-τ)=Determined using the linear trapezoidal method

AUC(0-□)=AUC(0-τ) plus extrapolated area determined by dividing plasma concentration at τ by the slope of the terminal log-linear phase $CL$=Dose/AUC(0-∞)

$Vdss$=$CL$×$MRT$

Cmax=Recorded directly from plasma concentration time curve

Tmax=Recorded directly from plasma concentration time curve $t^{1/2}$=ln(0.5)/slope of the terminal log-linear phase $F$ %=AUC(0-∞)$PO$ per dose/AUC(0-∞)$IV$ per dose C(0)=Extrapolated by linear regression from the apparent distribution phase following IV administration $MRT$=$AUMC$(AUC(0-∞)/AUC(0-∞)

TABLE 5

| Example | Dose (mg/kg) | Route/n | Formulation | Time points (h) | Cmax (µg/mL) | $AUC_{inf}$ (µg * h/mL) | CL (mL/min/kg) | $V_{ss}$ (L/kg) | $t_{1/2}$ (h) | F (%) |
|---|---|---|---|---|---|---|---|---|---|---|
| 4A | 2 | IV/ (n = 2) | DMSO/ PEG400/ 30% SBECD (10/30/60 v/v/v) | 0.083, 0.25, 0.5, 1, 2, 4, 6, 8, 20 | — | 8.48 | 4.04 | 1.1 | 4.1 | — |
| | 2 | PO/ (n = 3) | Tween 80/ 0.5% MC (0.1/99.9 v/v) | 0.5, 1, 2, 4, 7, 20 | 0.772 | 5.65 | — | — | 3.7 | 67 |

TABLE 5-continued

| Example | Dose (mg/kg) | Route/n | Formulation | Time points (h) | Cmax (µg/mL) | AUC$_{inf}$ (µg * h/mL) | CL (mL/min/kg) | V$_{ss}$ (L/kg) | t$_{1/2}$ (h) | F (%) |
|---|---|---|---|---|---|---|---|---|---|---|
|  | 5 | PO/ (n = 5) | 20% PEG/ 24% HBCD | 1, 4, 7, 24 | 1.19 | 16.8 | — | — | — | 79 |
| 12A | 2 | IV/ (n = 2) | DMSO/ PEG400/ 30% SBECD (5/10/85 v/v/v) | 0.083, 0.25, 0.5, 1, 2, 4, 5, 6, 7, 20 | — | 2.20 | 15.9 | 3.68 | 3.90 | — |
| 1A | 2 | IV/ (n = 2) | DMA/PG/ 50 mM Tris Base (5/10/85 v/v/v) | 0.083, 0.25, 0.5, 1, 2, 4, 6, 8, 20 | — | 0.947 | 37.1 | 1.71 | 0.962 | — |
|  | 10 | PO/ (n = 2) | PEG200/ 0.5% MC (5/ 95 v/v) | 0.25, 0.5, 0.75, 1, 2, 4, 6, 8, 20 | 1.65 | 2.68 | — | — | 2.82 | 56.5 |
| 14A | 2 | IV/ (n = 2) | DMSO/ PEG400/ 30% SBECD (5/10/85 v/v/v) | 0.25, 0.5, 1, 2, 4, 7, 20, 22 | — | 1.06 | 31.7 | 1.69 | 1.36 | — |
|  | 10 | PO/ (n = 2) | PEG200/ 0.5% MC (5/ 95 v/v) | 0.5, 1, 2, 4, 7, 20, 22 | 0.551 | 2.29 | — | — | 1.71 | 43.5 |
| 2A | 2 | IV/ (n = 2) | DMA/PG/ 50 mM Tris Base (5/10/85 v/v/v) | 0.083, 0.25, 0.5, 1, 2, 4, 6, 8, 20 | — | 1.34 | 27.7 | 1.03 | 0.94 | — |
| 3A | 2 | IV/ (n = 2) | DMA/PG/ 50 mM Tris Base (5/10/85 v/v/v) | 0.083, 0.25, 0.5, 1, 2, 4, 6, 8, 20 | — | 1.41 | 23.8 | 1.82 | 1.58 | — |

— = Data not available or not applicable;
DMSO = Dimethyl Sulfoxide;
HBCD = Hydroxypropyl beta cyclodextrin;
PEG = Polyetheylene Glycol;
PG = Propylene Glycol;
SBECD = Sulfobutylester beta cyclodextrin;
MC = Methylcellulose;
DMA = Dimethylaniline Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification including the examples be considered as exemplary only, with a true scope and spirit of the invention being indicated by the following claims.

What is claimed is:

1. A compound of Formula (A) or Formula (B)

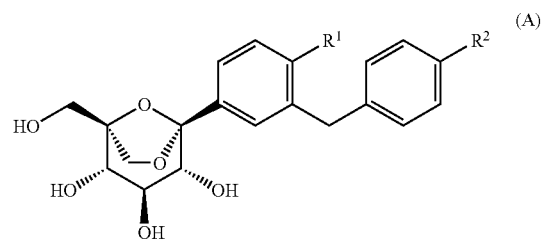

(A)

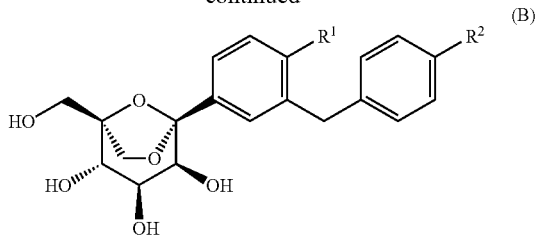

wherein
R¹ is H, ($C_1$-$C_4$)alkyl, ($C_1$-$C_4$)alkoxy, Cl, F, cyano, fluoro-substituted ($C_1$-$C_2$)alkyl, ($C_1$-$C_4$)alkyl-$SO_2$—, or ($C_3$-$C_6$)cycloalkyl; and
R² is ($C_1$-$C_4$)alkyl, ($C_1$-$C_4$)alkoxy, ($C_2$-$C_4$)alkynyl, 3-oxetanyloxy, 3-tetrahydrofuranyloxy, Cl, F, cyano, fluoro-substituted ($C_1$-$C_2$)alkyl, ($C_1$-$C_4$)alkyl-$SO_2$—, ($C_3$-$C_6$)cycloalkyl, or a ($C_5$-$C_6$)heterocycle having 1 or 2 heteroatoms each independently selected from N, O, or S.

2. The compound of claim 1 wherein said compound is a compound of Formula (A).

3. The compound of claims 1 or 2 wherein
R¹ is H, methyl, ethyl, propyl, isopropyl, methoxy, ethoxy, F, Cl, cyano, —$CF_3$, cyclopropyl, or cyclobutyl; and
R² is methyl, ethyl, propyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl.

4. The compound of claim 3 wherein
R¹ is H, methyl, ethyl, isopropyl, methoxy, ethoxy, F, Cl, cyano, —$CF_3$, or cyclopropyl; and
R² is methyl, ethyl, isopropyl, methoxy, ethoxy, F, Cl, cyano, —$CF_3$, —$CF_2CH_3$, ethynyl, 3-oxetanyloxy, 3-tetrahydrofuranyloxy, or cyclopropyl.

5. The compound of claim 4 wherein
R¹ is H, methyl, ethyl, methoxy, ethoxy, F, Cl, cyano, —$CF_3$, or cyclopropyl; and
R² is methyl, ethyl, methoxy, ethoxy, F, Cl, cyano, —$CF_3$, —$CF_2CH_3$, ethynyl, 3-oxetanyloxy, 3-tetrahydrofuranyloxy, or cyclopropyl.

6. The compound of claim 5 wherein
R¹ is methyl, ethyl, F, Cl, cyano, $CF_3$, or cyclopropyl; and
R² is methoxy, or ethoxy.

7. A compound selected from the group consisting of:
(1S,2S,3S,4R,5S)-1-hydroxymethyl-5-[3-(4-methoxy-benzyl)-4-methyl-phenyl]-6,8-dioxa-bicyclo[3.2.1]octane-2,3,4-triol;
(1S,2S,3S,4R,5S)-5-[3-(4-ethoxy-benzyl)-4-methyl-phenyl]-1-hydroxymethyl-6,8-dioxa-bicyclo[3.2.1]octane-2,3,4-triol;
(1S,2S,3S,4R,5S)-5-[4-chloro-3-(4-methoxy-benzyl)-phenyl]-1-hydroxymethyl-6,8-dioxa-bicyclo[3.2.1]octane-2,3,4-triol;
(1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol;
(1S,2S,3S,4R,5S)-5-[4-fluoro-3-(4-methoxy-benzyl)-phenyl]-1-hydroxymethyl-6,8-dioxa-bicyclo[3.2.1]octane-2,3,4-triol;
2-(4-methoxybenzyl)-4-((1S,2S,3S,4R,5S)-2,3,4-trihydroxy-1-(hydroxymethyl)-6,8-dioxa-bicyclo[3,2,1]oct-5-yl)benzonitrile;
2-(4-ethoxybenzyl)-4-((1S,2S,3S,4R,5S)-2,3,4-trihydroxy-1-(hydroxymethyl)-6,8-dioxa-bicyclo[3,2,1]oct-5-yl)benzonitrile;
(1S,2S,3S,4R,5S)-5-[3-(4-ethoxy-benzyl)-4-fluoro-phenyl]-1-hydroxymethyl-6,8-dioxa-bicyclo[3.2.1]octane-2,3,4-triol;
(1S,2S,3S,4R,5S)-5-{4-fluoro-3-[4-(tetrahydro-furan-3-yloxy)-benzyl]-phenyl}-1-hydroxymethyl-6,8-dioxa-bicyclo[3.2.1]octane-2,3,4-triol;
(1S,2S,3S,4R,5S)-5-[3-(4-chlorobenzyl)-4-fluorophenyl]-1-hydroxymethyl-6,8-dioxabicyclo[3.2.1]octane-2,3,4-triol;
(1S,2S,3S,4R,5S)-5-{4-fluoro-3-[4-(oxetan-3-yloxy)-benzyl]-phenyl}-1-hydroxymethyl-6,8-dioxa-bicyclo[3.2.1]octane-2,3,4-triol; and
(1S,2S,3S,4R,5S)-5-{4-chloro-3-[4-(oxetan-3-yloxy)-benzyl]-phenyl}-1-hydroxymethyl-6,8-dioxa-bicyclo[3.2.1]octane-2,3,4-triol.

8. A compound which is (1S,2S,3S,4R,5S)-5-[4-chloro-3-(4-ethoxy-benzyl)-phenyl]-1-hydroxymethyl-6,8-dioxa-bicyclo[3.2.1]octane-2,3,4-triol.

9. A compound selected from the group consisting of:
(1S,2S,3S,4S,5S)-1-hydroxymethyl-5-[3-(4-methoxy-benzyl)-4-methyl-phenyl]-6,8-dioxa-bicyclo[3.2.1]octane-2,3,4-triol;
(1S,2S,3S,4S,5S)-5-[3-(4-ethoxy-benzyl)-4-methyl-phenyl]-1-hydroxymethyl-6,8-dioxa-bicyclo[3.2.1]octane-2,3,4-triol;
(1S,2S,3S,4S,5S)-5-[4-chloro-3-(4-methoxy-benzyl)-phenyl]-1-hydroxymethyl-6,8-dioxa-bicyclo[3.2.1]octane-2,3,4-triol;
(1S,2S,3S,4S,5S)-5-[4-chloro-3-(4-ethoxy-benzyl)-phenyl]-1-hydroxymethyl-6,8-dioxa-bicyclo[3.2.1]octane-2,3,4-triol;
(1S,2S,3S,4S,5S)-5-[4-fluoro-3-(4-methoxy-benzyl)-phenyl]-1-hydroxymethyl-6,8-dioxa-bicyclo[3.2.1]octane-2,3,4-triol;
(1S,2S,3S,4S,5S)-5-[3-(4-ethoxy-benzyl)-4-fluoro-phenyl]-1-hydroxymethyl-6,8-dioxa-bicyclo[3.2.1]octane-2,3,4-triol; and
(1S,2S,3S,4S,5S)-5-[3-(4-chlorobenzyl)-4-fluorophenyl]-1-hydroxymethyl-6,8-dioxabicyclo[3.2.1]octane-2,3,4-triol.

10. A crystal comprising a compound having the formula (4A):

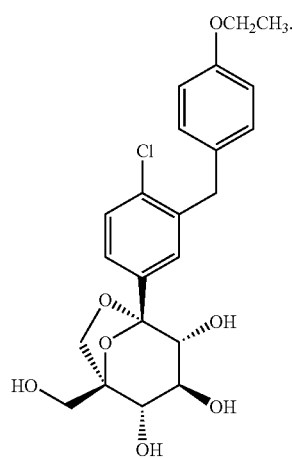

11. The crystal of claim 10 further comprising L-proline or L-pyroglutamic acid.

12. The crystal of claim 10 further comprising L-pyroglutamic acid and having one or more of the following:

a) space group of P2(1)2(1)2(1) and unit cell parameters substantially equal to the following:
a=7.4907(10) Å α=90°
b=12.8626(15) Å β=90°
c=28.029(4) Å γ90°;
b) a powder x-ray diffraction pattern comprising 2-theta values of (CuKα radiation, wavelength of 1.54056 Å) 6.4±0.2, 16.7±0.2, 17.4±0.2 and 21.1±0.2; or
c) a solid state $^{13}$C NMR spectrum comprising peak positions at 16.5±0.2, 131.1±0.2, 158.7±0.2, and 181.5±0.2 ppm as determined on a 500 MHz spectrometer relative to crystalline adamantine of 29.5 ppm.

13. The crystal of claim 10 further comprising L-pyroglutamic acid wherein the crystal is a co-crystal comprising the compound of formula (4A) and L-pyroglutamic acid in a 1:1 stoichiometric ratio.

14. The crystal of claim 10 further comprising L-pyroglutamic acid and having
a) a powder x-ray diffraction pattern comprising a 2-theta value of (CuKα radiation, wavelength of 1.54056 Å) 6.4±0.2; and
b) a solid state $^{13}$C NMR spectrum comprising peak positions at 16.5±0.2, 158.7±0.2, and 181.5±0.2 ppm as determined on a 500 MHz spectrometer relative to crystalline adamantine of 29.5 ppm.

15. The crystal of claim 10 further comprising L-proline and having one or more of the following:
a) space group of C2 and unit cell parameters substantially equal to the following:
a=32.8399(16) Å α=90°
b=7.2457(4) Å β=101.268(5)°
c=11.8023(6) Å γ=90°; or
b) a powder x-ray diffraction pattern comprising 2-theta values of (CuKα radiation, wavelength of 1.54056 Å) 7.6±0.2, 12.1±0.2, 20.3±0.2 and 28.8±0.2.

16. A pharmaceutical composition comprising (i) a compound of any of claims 1 through 9 or a crystal of any of claims 10-15; and (ii) a pharmaceutically acceptable excipient, diluent, or carrier.

17. A method for treating obesity and obesity-related disorders in animals comprising the step of administering to an animal in need of such treatment a therapeutically effective amount of a compound of any one of claims 1 through 9 or a therapeutically effective amount of a crystal of any one of claims 10 through 15.

18. A method for treating or delaying the progression or onset of Type 2 diabetes and diabetes-related disorders in animals comprising the step of administering to an animal in need of such treatment a therapeutically effective amount of a compound of any one of claims 1 through 9 or a therapeutically effective amount of a crystal of any one of claims 10 through 15.

19. A method for treating obesity and obesity-related disorders in animals comprising the step of administering to an animal in need of such treatment a pharmaceutical composition of claim 16.

20. A method for treating or delaying the progression or onset of Type 2 diabetes and diabetes-related disorders in animals comprising the step of administering to an animal in need of such treatment a pharmaceutical composition of claim 16.

* * * * *